(12) United States Patent
Kugler et al.

(10) Patent No.: US 7,445,010 B2
(45) Date of Patent: Nov. 4, 2008

(54) USE OF MAGNETIC IMPLANTS TO TREAT ISSUE STRUCTURES

(75) Inventors: Chad J Kugler, Andover, MN (US); Jerome K Grudem, Jr., Rogers, MN (US)

(73) Assignee: Torax Medical, Inc., Maple Grove, MN (US)

( * ) Notice: Subject to any disclaimer, the term of this patent is extended or adjusted under 35 U.S.C. 154(b) by 857 days.

(21) Appl. No.: 10/612,496

(22) Filed: Jul. 1, 2003

(65) Prior Publication Data

US 2004/0147801 A1  Jul. 29, 2004

Related U.S. Application Data

(60) Provisional application No. 60/465,283, filed on Apr. 23, 2003, provisional application No. 60/457,959, filed on Mar. 25, 2003, provisional application No. 60/444,065, filed on Jan. 29, 2003.

(51) Int. Cl.
*A61F 2/00* (2006.01)
*A61B 19/00* (2006.01)

(52) U.S. Cl. .................................... 128/897; 600/37

(58) Field of Classification Search .......... 128/DIG. 25; 600/9–15, 29–32, 37
See application file for complete search history.

(56) References Cited

U.S. PATENT DOCUMENTS

| | | | |
|---|---|---|---|
| 3,495,620 A * | 2/1970 | Bazell et al. ............... 137/529 |
| 3,952,726 A * | 4/1976 | Hennig et al. .............. 600/30 |
| 4,154,226 A * | 5/1979 | Hennig et al. .............. 600/30 |
| 4,197,840 A | 4/1980 | Beck et al. |
| 4,271,827 A | 6/1981 | Angelchik |
| 5,176,618 A | 1/1993 | Freedman .................. 600/12 |
| 5,234,447 A | 8/1993 | Kaster et al. |
| 5,234,448 A | 8/1993 | Wholey et al. |
| 5,387,235 A | 2/1995 | Chuter |
| 5,509,888 A | 4/1996 | Miller et al. |
| 5,695,504 A | 12/1997 | Gifford, III et al. |
| 5,843,164 A | 12/1998 | Frantzen et al. |
| 5,876,448 A | 3/1999 | Thompson et al. |

(Continued)

FOREIGN PATENT DOCUMENTS

DE  30 11 742  10/1981

(Continued)

OTHER PUBLICATIONS

Shigley et al., *Mechanical Engineering Design*, Fifth Edition, 1989, McGraw-Hill, Inc., New York, pp. 58-60.

*Primary Examiner*—Samuel G Gilbert
(74) *Attorney, Agent, or Firm*—Ropes & Gray LLP; Robert R. Jackson

(57) ABSTRACT

Plural (at least two) magnetic devices are implanted in a patient so that magnetic interaction between those devices modifies the patient's body in one or more respects (e.g., by modifying the shape and/or performance of some part of the body) Prior to implantation, a location in the body may be marked for later reference during the implantation. The magnetism of one or more of the magnetic devices may be changed in vivo after implantation. One or more of the implanted devices may be subsequently removed from the patient if desired. Use of the magnetic devices inside tissue conduits (e.g., as a treatment for GERD) is especially considered by way of illustration.

7 Claims, 61 Drawing Sheets

U.S. PATENT DOCUMENTS

| | | | |
|---|---|---|---|
| 5,954,506 A * | 9/1999 | Tanaka | 433/214 |
| 5,957,949 A | 9/1999 | Leonhardt et al. | |
| 6,056,744 A | 5/2000 | Edwards | |
| 6,074,341 A | 6/2000 | Anderson et al. | |
| 6,136,006 A | 10/2000 | Johnson et al. | |
| 6,146,416 A | 11/2000 | Andersen et al. | |
| 6,173,715 B1 * | 1/2001 | Sinanan et al. | 128/899 |
| 6,302,917 B1 | 10/2001 | Dua et al. | |
| 6,409,656 B1 * | 6/2002 | Sangouard et al. | 600/30 |
| 6,497,647 B1 * | 12/2002 | Tucker | 600/8 |
| 6,604,529 B2 * | 8/2003 | Kim | 128/899 |
| 2002/0091295 A1 | 7/2002 | Wilk | |
| 2003/0153806 A1 | 8/2003 | Miller | |
| 2004/0260393 A1 * | 12/2004 | Rahdert et al. | 623/2.36 |

FOREIGN PATENT DOCUMENTS

| | | |
|---|---|---|
| WO | WO 00/59398 | 10/2000 |
| WO | WO 01/47431 | 7/2001 |
| WO | WO 2004/004544 A2 | 1/2004 |

* cited by examiner

NEGATIVE POLARITY   POSITIVE POLARITY

EQUIVALENT POLARITY ON
ALL MAGNETS

USE OF MAGNETIC IMPLANTS TO TREAT ISSUE STRUCTURES

This application claims the benefit of U.S. provisional patent applications Nos. 60/444,065 (filed Jan. 29, 2003), 60/457,959 (filed Mar. 25, 2003), and 60/465,283 (filed Apr. 23, 2003), all of which are hereby incorporated by reference herein in their entireties.

BACKGROUND OF THE INVENTION

This invention relates to medical apparatus and procedures, and more particularly to apparatus and methods for treating tubular or similar body organ tissue structures for such purposes as strengthening some of their functions, reducing their size or otherwise modifying their geometry, changing wall tension, restricting flow, affecting or effecting tissue movement, and/or the like.

This invention has many possible applications. More examples of such applications will be mentioned later in this specification. Initially, however, it will suffice to discuss the problem of gastro-esophageal reflux disorder or disease ("GERD") as background for the invention.

GERD is a condition in which the sphincter and/or other body structures at or near the transition between the lower end of the esophagus and the upper end of the stomach does or do not keep that passageway closed in the normal way. This can allow material in the stomach to re-enter the esophagus, which can be uncomfortable for the patient and, in the long term, can endanger the patient (e.g., by causing damage to and/or disease of the esophagus).

A common cause of GERD is weakness or relaxation of the sphincter that normally keeps the lower end of the esophagus closed (the lower esophageal sphincter or LES). Alternatively or in addition, there may be displacement of other tissue structures relative to the LES that may make the esophagus-closing mechanism less effective than it should be.

Many other similar conditions can exist elsewhere in the body. For example, a sphincter in the urinary tract can become weak, resulting in urinary incontinence. The tissue surrounding or adjacent to any lumen in the body may be in need of an improvement in tone (i.e., an improvement in muscle tone or analogous to an improvement in muscle tone). Such an improvement in tone may help to reduce the size of the lumen or otherwise modify the shape or geometry of the lumen, strengthen or assist a sphincter associated with the lumen, and/or otherwise improve the performance of the lumen. In addition to the improvements in tone described above other body lumen improvements may also be desirable. For example, such improvements may include closure or restriction of a body lumen to limit or stop the passage of gas, liquid, or solids in the body lumen (such as the urethra or bladder for incontinence control) or in a body cavity such as in the stomach or lungs. The term "passage" may be used herein as a generic term for tubular tissue structures or lumens and for body cavities.

In view of the foregoing, it is an object of this invention to provide apparatus and methods for such purposes as improving the tone of, strengthening, reinforcing, and/or reducing the size or otherwise changing the geometry of any of various lumens, organs, cavities, or similar structures in a patient's body.

SUMMARY OF THE INVENTION

This and other objects of the invention are accomplished in accordance with the principles of the invention by apparatus and methods whereby multiple (at least two) magnetic devices are implanted in a patient so that magnetic attraction (or repulsion) between those devices modifies adjacent tissue structures. The magnetic devices employed in accordance with the invention can be all actively magnetic devices, or one or more passively magnetic devices can be used with one or more actively magnetic devices. An actively magnetic device is a source of a magnetic field. Examples of actively magnetic devices are permanent magnets and electromagnets. A passively magnetic device is not itself a magnetic field source, but it is magnetically responsive to a magnetic field (e.g., it is magnetically attracted to an actively magnetic device). An example of a passively magnetic device is a body of initially unmagnetized ferro-magnetic material. As used herein, the phrase "magnetic device" generally refers to both actively and passively magnetic devices. However, it should be understood that in any system of multiple magnetic devices there will generally need to be at least one actively magnetic device.

Another aspect of the invention relates to methods and apparatus for marking a location in a patient for use as a reference during subsequent implanting of magnetic devices.

Still another aspect of the invention relates to methods and apparatus for removing a magnetic device that has been implanted in a patient.

Yet another aspect of the invention relates to methods and apparatus for changing the magnetism, in vivo, of at least one magnetic device that has been implanted in a patient.

Further features of the invention, its nature and various advantages will be more apparent from the accompanying drawings and the following detailed description of the preferred embodiments.

BRIEF DESCRIPTION OF THE DRAWINGS

(FIG. 52 is taken generally along the line 52-52 in FIG. 53.)

(FIG. 54 is taken generally along the line 54-54 in FIG. 55.)

(FIG. 56 is taken generally along the line 56-56 in FIG. 57.)

(FIG. 61 is taken generally along the line 61-61 in FIG. 62; FIG. 62 is taken generally along the line 62-62 in FIG. 61; FIG. 63 is taken generally along the line 63-63 in FIG. 64; and FIG. 64 is taken generally along the line 64-64 in FIG. 63.

(FIG. 78 is taken generally along the line 78-78 in FIG. 79).

DETAILED DESCRIPTION

As in the case of the above background section, this detailed description will illustrate the invention initially by discussing application of the invention to the treatment of GERD. Later, some of the invention's other possible uses will be discussed.

Figure 1:
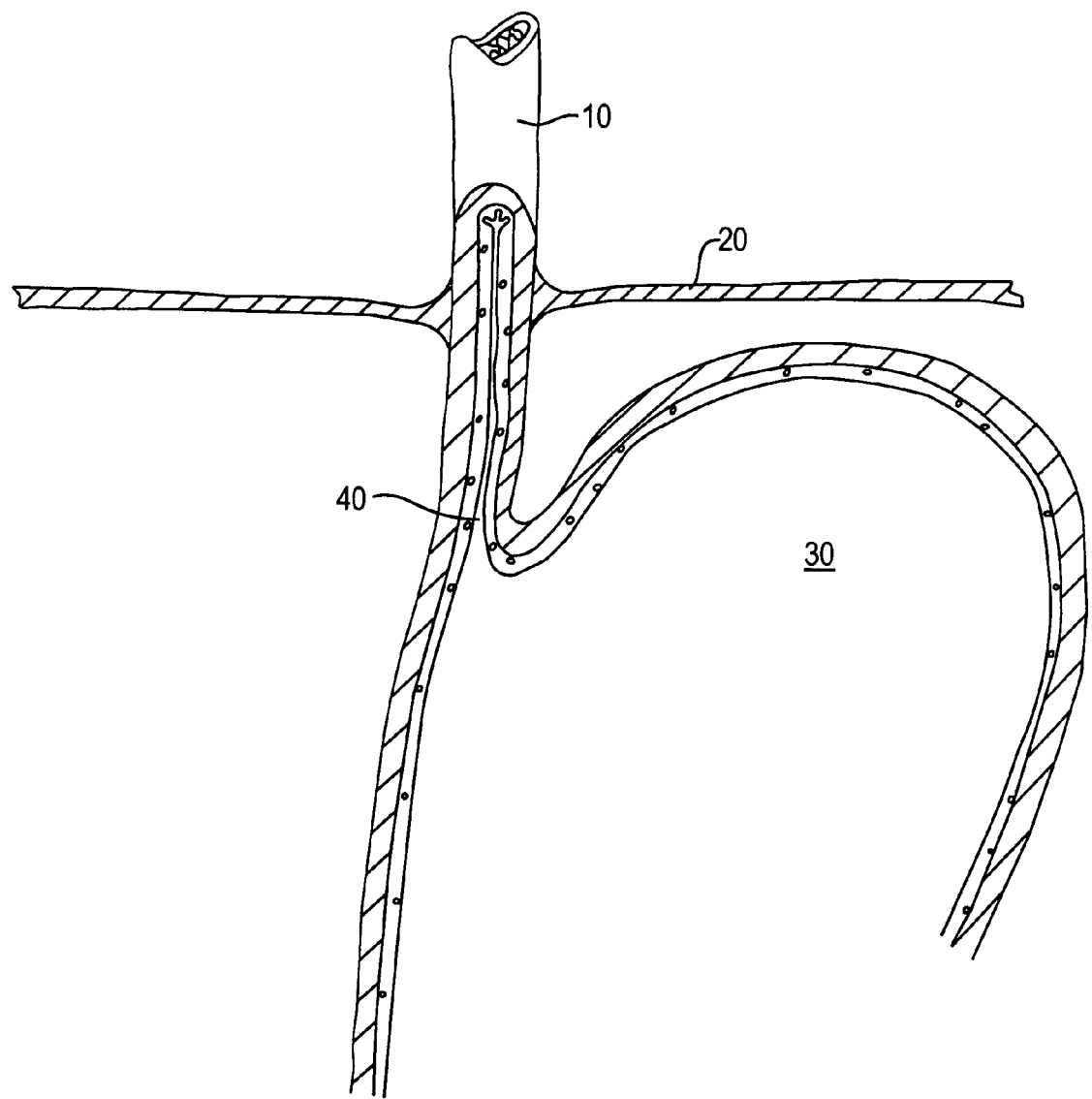
FIG. 1 is a simplified sectional view of a portion of a patient's internal anatomy.

The lower part of a patient's esophagus 10 and adjacent tissue structures are shown in FIG. 1. It will be understood that this and other anatomical depictions herein are generally greatly simplified. The same is true for the anatomical descriptions herein, both before and after treatments in accordance with this invention. Many anatomical structures and functions are in fact quite complex, to the point where they may not even be fully understood. For example, it may be convenient herein to say that the esophagus is "open" or "closed" under certain conditions (either before or after treatment in accordance with the invention), when in fact the esophagus may be only partly open when said to be "open", only partly closed (or still partly openable without separating the magnetic devices as described below) when said to be "closed", etc. It will therefore be understood that words like "open" and "close" and other terms and descriptions employed herein are used in a simplified (sometimes relative) sense to provide a general indication of how various anatomical structures operate, both before and after treatment in accordance with the invention.

In addition to esophagus 10, FIG. 1 shows a portion of the patient's diaphragm 20 (through which the esophagus passes), the upper part of the stomach 30, and the lower esophageal sphincter 40, which is just above the opening into the stomach and normally close to the diaphragm. The lower part of the esophagus is normally closed by sphincter 40, perhaps with some help from the adjacent diaphragm structure 20. Anything swallowed passes down esophagus 10, opening sphincter 40, and entering stomach 30. The esophagus then normally closes again. Normal pressures in stomach 30 should not cause sphincter 40 to open. But higher than normal pressures in the stomach do cause sphincter 40 to open and allow material (e.g., gas) to escape from the stomach and exit via the esophagus. In a patient with GERD, however, sphincter 40 and/or adjacent structures do not resist normal pressure in the stomach, and so material (e.g., gas or liquids) from the stomach can enter the esophagus and cause discomfort and potentially serious disease.

Figure 2:
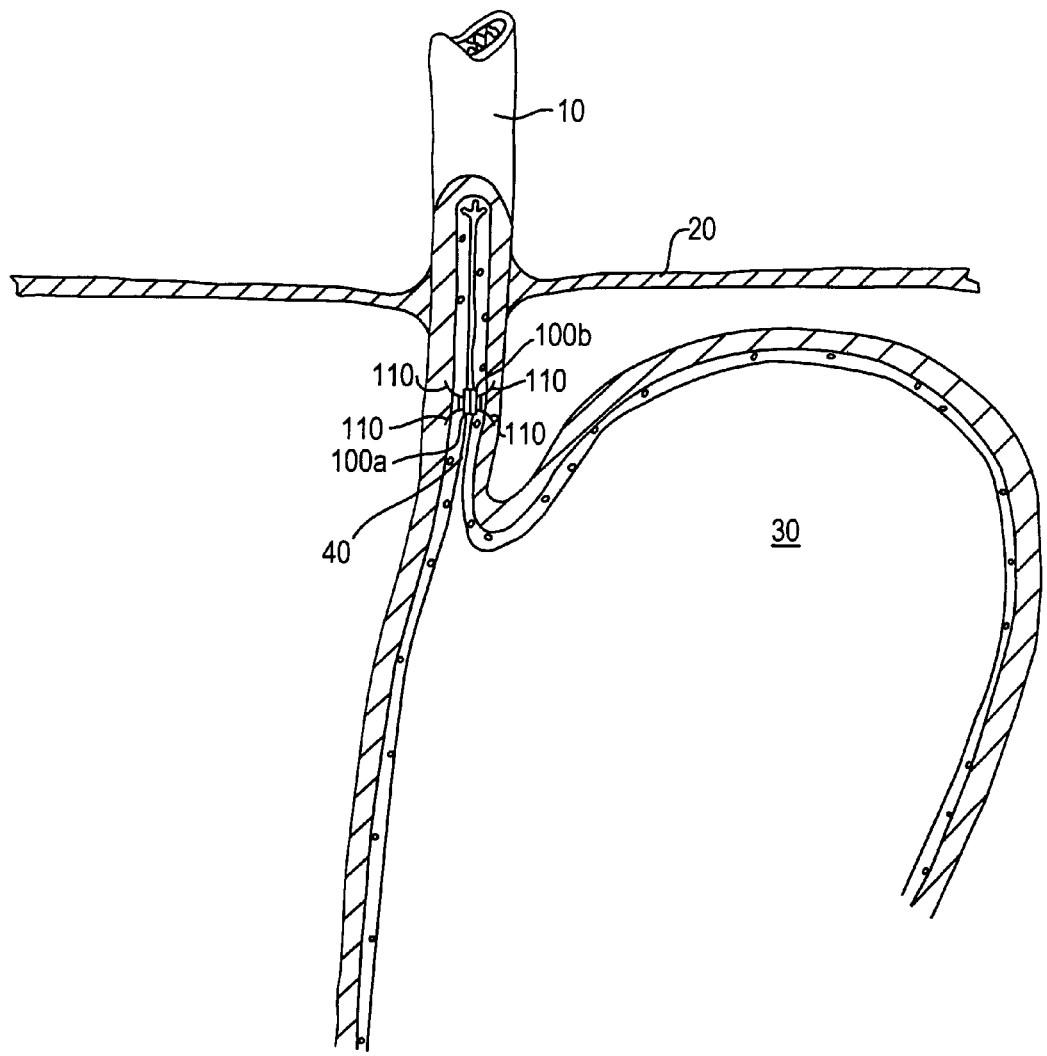
FIG. 2 is similar to FIG. 1, but with the addition of illustrative structures in accordance with the invention.

FIG. 2 shows the end result of treatment of a patient for GERD in accordance with an illustrative embodiment of the invention. As shown in FIG. 2, two magnetic devices 100a and 100b have been implanted in the patient's esophagus in the vicinity of esophageal sphincter 40. At least one of devices 100 is actively magnetic. As mentioned earlier, an actively magnetic device (e.g., a permanent magnet or an electromagnet) is a source of a magnetic field. The other of devices 100 may be either actively magnetic or passively magnetic (e.g., a body of initially unmagnetized ferro-magnetic material). Thus the phrase "magnetic device" generally refers to both actively and passively magnetic devices. However, it will be understood that in any system of multiple magnetic devices there should be at least one actively magnetic device.

In the particular embodiment shown in FIG. 2 magnetic devices 100a and 100b are implanted in esophagus 10 so that they magnetically attract one another and help to hold the esophagus closed in their vicinity. There are many ways that devices 100 can be implanted, as will be illustrated later in this specification. The primary purpose of the present discussion is to consider various preferred aspects of the end result.

In the illustrative embodiment shown in FIG. 2 each of devices 100a and 100b is implanted on a respective diametrically opposite side of the esophageal lumen. (As will be considered in greater detail in connection with later FIGS., there may be more than one such "set" of magnetic devices 100 implanted in the patient. For example, such other "sets" may be implanted at some longitudinal distance along the esophagus from the first set. Many other arrangements of multiple sets of implanted magnetic devices 100 are also possible, as will be further illustrated later in this specification.) The preferred axial location for devices 100 along the longitudinal axis of the esophagus is adjacent lower esophageal sphincter 40. Devices 100 are implanted on or in the inner wall surface of the esophageal lumen in this embodiment. A possible advantage of this type of surface-implanting is that there is then no tissue between magnetic devices 100a and 100b when those devices are able to be pulled together (as shown in FIG. 2) by the magnetic attraction between them. This tends to give better fore-knowledge of the end-point magnetic attraction between devices 100. Magnetic attraction drops off rapidly as the distance between devices 100 increases. Tissue thicknesses can vary. If one or more tissue thicknesses are between devices 100 when they are closest together, it can be more difficult to predict how strong the end-point magnetic attraction will be. But if there is no tissue between devices 100 when they are closest together in the patient, the magnitude of the end-point magnetic attraction should be the same as when the devices are outside the patient prior to being implanted. In other words, the in vivo end-point magnetic attraction can be more easily designed into the devices if no variable tissue thickness comes between those devices when they are closest together in vivo.

The strength of the magnetic attraction between devices 100a and 100b can be any amount that is helpful to keep esophagus 10 at least partly closed in the absence of material (e.g., food or liquid) moving down the esophagus or in the absence of higher than normal stomach pressure that should produce some escape of material (e.g., gas) up the esophagus. For example, the end-point magnetic attraction between devices 100a and 100b may be in the range from about 10 g to about 500 g of force. The amount of force thus employed may depend on the clinical application of the technology, various clinical applications being mentioned throughout this specification.

Many different securing techniques can be used for magnetic devices 100a and 100b. Alternatives will be discussed later in this specification. But for present purposes it will suffice to note that FIG. 2 shows that each of devices 100a and 100b has two sharply pointed prongs 110 that extend out from the rear of the associated device in directions that diverge from one another away from the remaining, main body of the associated device. In the illustrative embodiment shown in FIG. 2 each of prongs 110 is made of metal, preferably a highly elastic, resilient metal such as nitinol. In this embodiment prongs 110 are resiliently biased to assume the positions shown in FIG. 2. The prongs 110 of each device 10 preferably penetrate the tissue of the esophagus, perhaps first entering that tissue relatively parallel to one another, and then spreading apart in or beyond the tissue to secure the device to the tissue and resist removal of the device from the tissue. The free ends of prongs 110 are preferably sharpened to facilitate this penetration of the tissue by the prongs. FIG. 2 shows the tissue as essentially a two-layer structure. But the tissue structure may in fact have even more layers than this, depending to some extent on how closely one analyzes the structure. Prongs 110 may penetrate this tissue structure to any desired degree. In the embodiment shown in FIG. 2 prongs 110 are shown passing through a superficial inner layer of the tissue structure and entering a more muscular (and therefore stronger) outer layer of the tissue. It is desirable for the attachment structure to engage some relatively strong tissue structure to ensure good retention of devices 100. An alternative to what is shown in FIG. 2 (discussed in more detail later in this specification) is to have the retention structure such as prongs 110 pass almost all the way through the associated tissue structure.

Devices 100 are designed so that they will be tolerated by the patient after they have been implanted. For example, devices 100 are designed so that they will be basically inert in the patient. In this context "inert" just means that devices 100 should not be destructively attacked by anything in the patient's body that they will come in contact with. Inert also means that devices 100 should not stimulate a rejection mechanism by the patient's body. Moreover, devices 100 do not release anything that would be harmful to the patient (although they may be medicated to release one or more drugs into the patient). Thus at least the material or materials of all external surfaces of devices 100 are preferably biocompatible. Some of the materials used inside of devices may not be biocompatible, but any such materials are enclosed or encapsulated using materials that are biocompatible.

Reverting again to the operation of the illustrative embodiment shown in FIG. 2, after devices. 100a and 100b have been installed in the patient as shown in FIG. 2, these devices magnetically attract one another across the esophagus and help sphincter 40 and/or the esophagus remain substantially closed at the location of sphincter 40 or adjacent esophagus. When the patient swallows something relatively solid, devices 100a and 100b may move apart from one another and thereby allow the swallowed material to pass down the esophagus, through the opened sphincter 40, and into stomach 30. Thereafter, the magnetic attraction between devices 100 pulls them toward one another again, thus helping to hold the esophagus at least partly closed at or adjacent to sphincter 40. Swallowing liquid may not cause devices 100 to separate. Instead, the tissue around the magnets may open sufficiently to allow the swallowed liquid to pass without devices 100 separating. Normal pressure in the stomach is not high enough to completely open sphincter 40, reinforced by the mutual magnetic attraction of devices 100. Higher than normal pressure in the stomach, however, is able to open sphincter 40 and separate devices 100 from one another. This allows such higher than normal stomach pressure to be relieved by a flow of material up the esophagus. Again, after such a pressure-relieving back-flow of material, the magnetic attraction between devices 100 helps to reclose sphincter 40. It is also possible that magnets 100a and 100b will remain closed, but surrounding tissue may open to allow gas in the stomach to pass back through the esophagus under certain higher pressure conditions in the stomach.

In connection with what is said above about implanted magnetic devices 100 being beneficial even when they remain together but allow adjacent portions of the esophagus to open under certain conditions, the following discussion may be helpful. Positioning magnets within the esophagus can increase lower esophageal sphincter ("LES") tone by a factor directly related to the geometry obtained. In the case of two magnets positioned 180° apart, the normally round cross section of the LES is pinched in the middle, creating two separate lobes that approximate two separate cylinders. Each of these lobes comprises approximately half the original esophagus circumference and half the original esophagus diameter. This reduction in circumference and diameter results in an increase in LES tone. This increase in tone (and the effect of stomach pressure on these lobes) may be described in general, theoretical terms in equations found in the textbook, Shigley et al., *Mechanical Engineering Design*, Fifth Edition, 1989, McGraw-Hill, Inc., New York, pp. 58-60. This text suggests that a reduction of a thin-walled conduit diameter by a factor of two will double the strength of the conduit wall to resist an internally applied pressure. In the case of the LES, this duplication in strength may result in an increase in tone and an increase in the pressure barrier to stomach acid reflux.

Although not expressly mentioned earlier, it should be apparent from what has been said that any actively magnetic material in either of devices 100 is magnetically polarized relative to the physical structure of the device so that when the devices are implanted in the patient as shown in FIG. 2, devices 100 will magnetically attract one another across the lumen of the esophagus. (In other embodiments and/or applications of the invention the magnetic polarization may be such as to cause devices like 100a and 100b to magnetically repel one another.)

Figure 3:
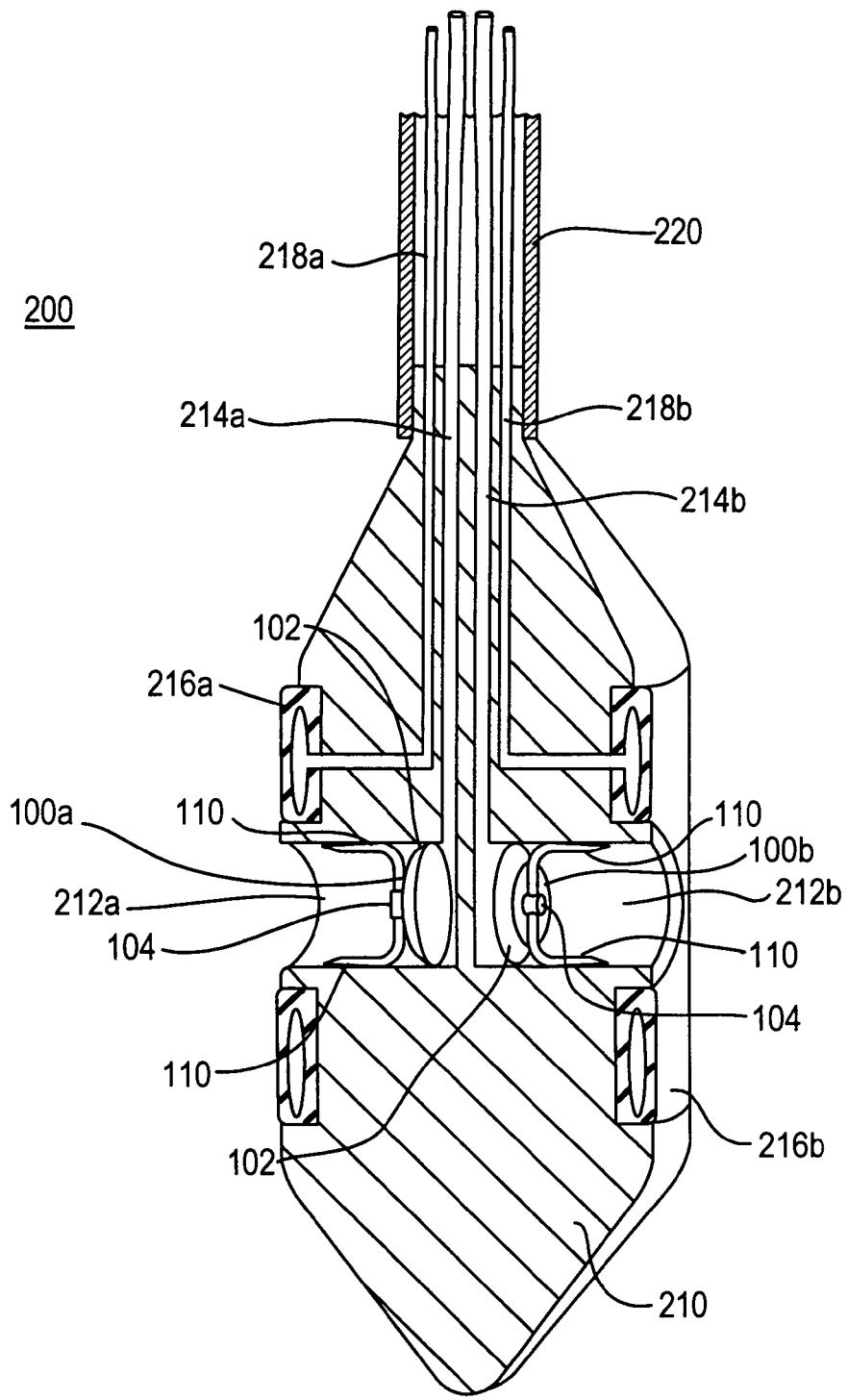
FIG. 3 is a simplified, partial, sectional view of illustrative apparatus in accordance with the invention.

FIG. 3 shows a portion of illustrative apparatus in accordance with the invention for implanting devices like 100 in a patient's esophagus as shown in FIG. 2. Again, many variations of and alternatives to what is shown in FIG. 3 are possible. Some of these variations and alternatives will be discussed later in this specification. But what is shown in FIG. 3 will serve as a useful starting point.

FIG. 3 shows that each of devices 100a and 100b may include a disc-like main body 102. A short post or stud 104 may project substantially perpendicularly out from the center of one of the major, approximately planar surfaces of main body 102. Prongs 110 extend from opposite sides of each stud 104. For example, the prongs 110 of each device 100 may be respective opposite end portions of a single wire or wire-like member that passes through the stud 104 of that device transverse to the longitudinal axis of the stud. The magnetic material of each device 100 is preferably at least primarily the main body 102 of that device (or is contained or encapsulated within the main body 102 of that device). Again, any actively magnetic material in either device 100 is magnetically polarized so that at least after the devices have been implanted in a patient, they will magnetically attract one another.

Figure 4:
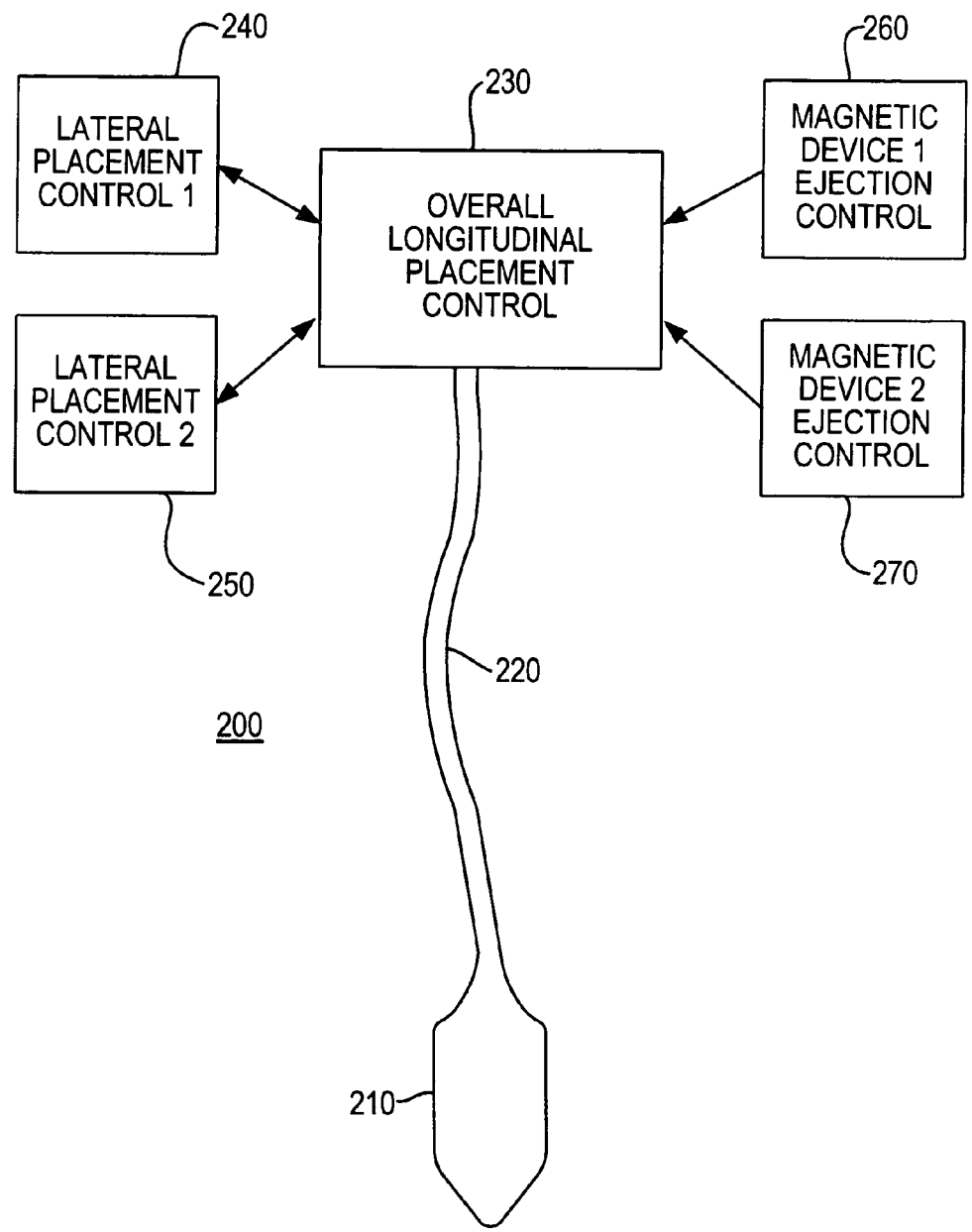
FIG. 4 is a simplified, partly elevational and partly block diagram depiction of illustrative apparatus in accordance with the invention.

In addition to showing illustrative devices 100 in a bit more detail, FIG. 3 shows a relatively distal portion of delivery system apparatus 200 for use in implanting devices 10 into a patient's esophagus as shown in FIG. 2. More of delivery system 200 is shown in FIG. 4. The portion of delivery system 200 that is shown in FIG. 3 includes a body structure 210 secured to a distal portion of an elongated catheter or catheter-like structure 220. At or adjacent its proximal end catheter 220 is attached to a system of control elements 230, 240, 250, 260, and 270 (see FIG. 4). Catheter structure 220 is preferably at least long enough so that distal portion 210 can be introduced into the patient through the patient's mouth and passed down esophagus 10 to the vicinity of sphincter 40, while elements 230, 240, 250, 260, and 270 remain outside the patient. Overall longitudinal placement of distal portion 210 in the patient (i.e., adjacent sphincter 40) is controlled by control element 230 acting through catheter 220. For example, distal portion 210 may be pushed distally into the patient or pulled proximally out of the patient by moving control element 230 toward or away from the patient's mouth. Catheter structure 220 (although somewhat transversely flexible) acts as a longitudinally extending mechanical connection between elements 210 and 230.

Returning to FIG. 3, each of devices 100a and 100b is initially loaded in a respective one of recesses 212a and 212b in the side wall of distal portion 210. Each of recesses 212 extends substantially radially with respect to a longitudinal axis of distal portion 210. Recesses 212 are on diametrically opposite sides of distal portion 210. The cross sectional shape and size of each recess 212 are approximately the same as the outer perimeter shape and size of the main body 102 of the device 100 initially loaded in that recess. These shapes and sizes are chosen so that each device 100 will have a relatively tight, but still slidable fit within the associated recess 212.

At one of its ends, each recess 212 opens to the outer surface of distal portion 210. At its other end, each recess 212 communicates with an associated lumen 214a or 214b for liquid or gas (generically fluid).

While each device 100 is disposed in its associated recess 212, the prongs 110 of that device are resiliently deflected inwardly by the side wall of the recess. This deflection makes the prongs 110 of each device 100 substantially parallel to one another and pointing radially outwardly relative to a central longitudinal axis of distal portion 210.

On the side surface of distal portion. 210, the opening of each recess 212 is surrounded by an inflatable balloon structure 216a or 216b. Balloon structures 216 do not have to completely surround each recess 212, but it is desirable for each balloon structure 216 to be relatively symmetrical about the associated recess 212 opening. The interior of each balloon structure 216 is in fluid communication with a respective one of inflation lumens 218a and 218b. Each balloon structure 216 can be inflated by supplying pressurized fluid to that balloon structure via the associated inflation lumen 218. After such inflation, a balloon structure 216 can be deflated by allowing the inflation fluid to flow back out of the balloon via the associated lumen 218.

The purpose of each balloon structure 216 is to press distal portion 210 against the opposite side of the esophagus, and also to somewhat temporarily enlarge or distend the esophagus and annularly stretch its tissue adjacent distal portion 210. For example, by inflating balloon structure 216b when distal portion 210 is at the desired location longitudinally along the esophagus, the radially outer opening of recess 212a is pushed against the side of the inner surface of the esophagus diametrically opposite inflated balloon structure 216b. As a result, the tissue of the esophagus is somewhat stretched across the opening of recess 212a. Pressurized fluid is then applied to lumen 214a, which drives device 100a out of recess 212a and into the immediately adjacent portion of the wall of the esophagus. In particular, the prongs 110 of device 100a first begin to exit recess 212a and enter the esophagus wall tissue substantially parallel to one another. As more of the length of prongs 110 extends from recess 212a, the prongs are gradually less constrained by the wall of the recess. Prongs 110 are therefore increasingly able to deflect away from one another as they penetrate farther into the esophagus wall tissue. Ultimately device 100a is pushed completely out of recess 212a and the prongs 110 of that device are fully embedded in the wall of the esophagus in the spread-apart condition shown in FIG. 2. (Of course, at this point the condition of the patient differs from what is shown in FIG. 2 because the distal portion of delivery apparatus 200 is still in the patient's esophagus with balloon structure 216b still inflated and device 100b not yet driven out of the delivery apparatus.)

The next steps are to deflate balloon structure 216b via lumen 218b and to then inflate balloon structure 216a via lumen 218a. This pushes distal portion 210 toward the opposite side of the patient's esophagus, causing the tissue of that side of the esophagus to be somewhat stretched over the opening of recess 212b. Device 100b is then driven out of recess 212b by the application of pressurized fluid to lumen 214b. Device 100b deploys from recess 212b in the same way that has been described above for the deployment of device 100a from recess 212a.

After device 100b has been deployed, balloon structure 216a is deflated via lumen 218a and the distal portion of delivery system 200 is pulled out of the patient via the patient's mouth. The condition of the patient is now as shown in FIG. 2.

Returning to FIG. 4, lateral placement control 1 (element 240) controls the inflation and deflation of balloon structure 216a, lateral placement control 2 (element 250) controls the inflation and deflation of balloon structure 216b, magnetic device 1 ejection control 260 controls the ejection of device 100a from recess 212a (in this embodiment, via pressurized fluid supplied to recess 212a behind device 100a), and magnetic device 2 ejection control 270 similarly controls ejection of device 100b from recess 212b. Because in this embodiment pressurized fluid is used to effect the various functions controlled by elements 240, 250, 260, and 270, lumens for such fluid may extend from each of these elements, through catheter structure 220, to the relevant parts of distal portion 210. For example, inflation lumen 218a may extend between element 240 and balloon structure 216a, and pressurized fluid lumen 214a may extend between recess 212a and element 260. One or more sources of pressurized fluid may be in or connected to control elements 240, 250, 260, and 270, and each of these elements typically includes a controllable valve for allowing pressurized fluid to selectively pass into (or out of) the appropriate portion of the remainder of the apparatus.

Although shown separately in FIG. 4, all or various ones of elements 230, 240, 250, 260, and 270 may be integrated together. Also, some or all of the various control elements may be operationally interlocked and/or sequenced to make sure that they are operable only in a certain sequence. For example, such interlocking may prevent simultaneous operation of elements 240 and 250. Similarly, such interlocking may prevent element 270 from being operated before element 240 has been operated, and may further prevent element 260 from being operated before element 250 has been operated. Some or all of the operating sequence of delivery device 200 may be automated, if desired.

Figure 5:
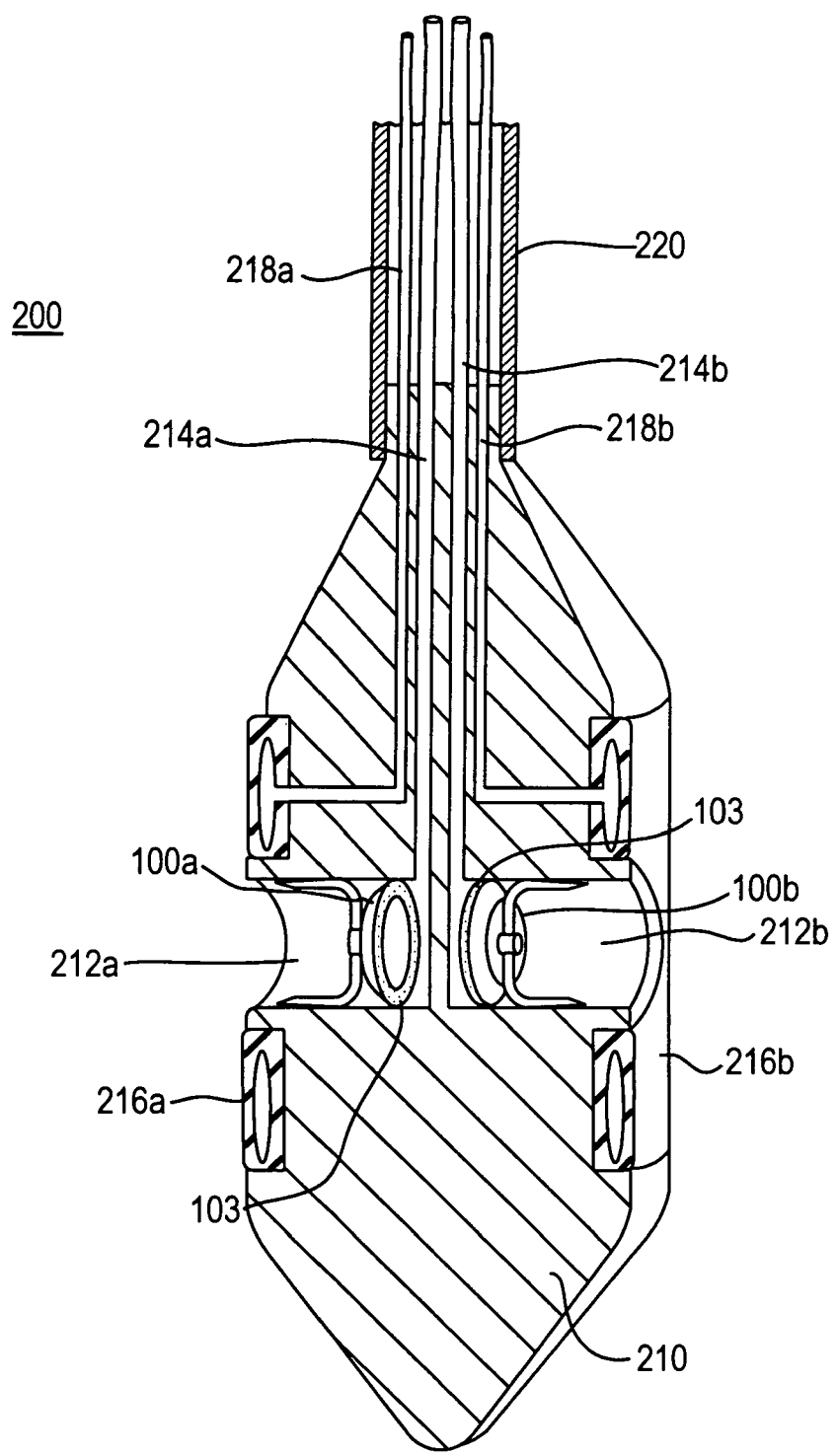
FIG. 5 is similar to FIG. 3 for another illustrative embodiment of the invention.

FIG. 5 shows an alternative embodiment of the portion of delivery apparatus 200 that is shown in FIG. 3. The only significant difference between what is shown in FIG. 5 and what is shown in FIG. 3 is the following. In FIG. 3 the main body 102 of each of devices 100 fits sufficiently closely in the associated recess 212 that pressurized fluid in the recess behind the device can be used to eject the device from the recess. In FIG. 5 rubber or rubber-like O-ring or a disk 103 is positioned behind each device 100 in the associated recess 212 to help provide a seal for pressurized fluid that will be injected into the recess. This helps ensure sufficient fluid pressure build-up in each recess 212 to drive the associated device 100 from that recess. In other respects the FIG. 5 alternative can be constructed and operated as described above for FIG. 3, and what is shown in FIG. 5 can be the distal portion 210 of the more complete delivery system 200 shown in FIG. 4.

Figure 6:
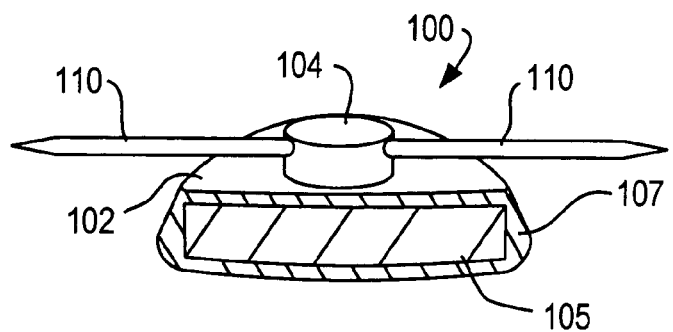
FIG. 6 is a simplified perspective view, partly in section, of an illustrative embodiment of an implantable magnetic device in accordance with the invention.

FIG. 6 shows some more details about one illustrative construction of a representative magnetic device 100 of the type described above. This embodiment includes disk-shaped permanent magnet. 105 embedded in an external structural shell 107. The magnet can be made of any material capable of producing a magnetic field. Because of their superior field strength, rare earth magnets are particularly preferred. Examples include Alnico (aluminum/nickel/cobalt), SmCo (samarium/cobalt), and NdFeB (neodymium/iron/boron). The force exerted by the magnet depends on such factors as the material of the magnet, the amount of magnetic material, the dimensions of the magnet, etc. As noted earlier in this specification, the required magnet strength will depend on the intended application. For example, for treating the esophagus as described above, the magnetic force should be sufficient to help keep the esophagus closed except when material is being swallowed or when there is higher than normal pressure in the stomach. Magnet 105 may be encapsulated in the structural shell 107 by welding, potting, injection molding, press fitting, or any other means of surrounding the magnet with a suitable material.

Suitable materials for external shell 107 are preferably non-porous, biocompatible, biostable, corrosion resistant, and strong enough to withstand in vivo loads. Examples of suitable materials include (but are not limited to) known implantable metals such as stainless steel or titanium, high-density polymers such as parylene or ultra-high molecular weight polyethylene, or materials made from non-metallic minerals such as ceramic or glass.

Figure 7:
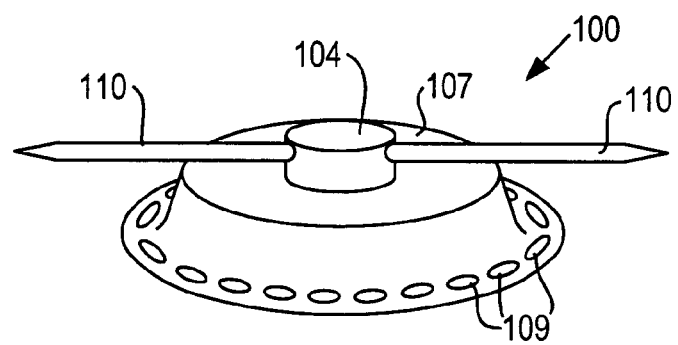
FIG. 7 is a simplified perspective view of another illustrative embodiment of an implantable magnetic device in accordance with the invention.

FIG. 7 shows an embodiment of the magnet housing 107 with an added feature that includes through-holes 109 located around the circumference that are designed to facilitate more permanent attachment to the esophagus wall via tissue in-growth.

Figure 8:
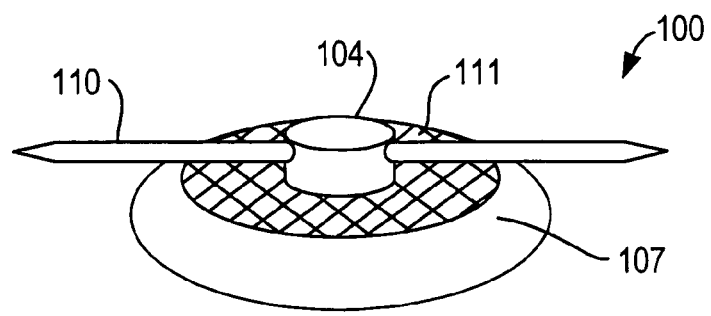
FIGS. 8-10 are similar to FIG. 7 for other illustrative embodiments of implantable devices in accordance with the invention.

FIG. 8 is similar to FIG. 7, but shows an alternative embodiment of the magnet housing 100 with a mesh 111 fixed to or formed as part of the surface that will be in closest and most extensive contact with the wall of the esophagus in a patient. Mesh 111 can be made from any known implantable metallic or polymeric material. Preferred materials include titanium, stainless steel, nitinol, polyester, Dacron, and Teflon. Tissue in-growth into mesh 111 increases the permanence with which device 100 is implanted in the patient.

Figure 9:
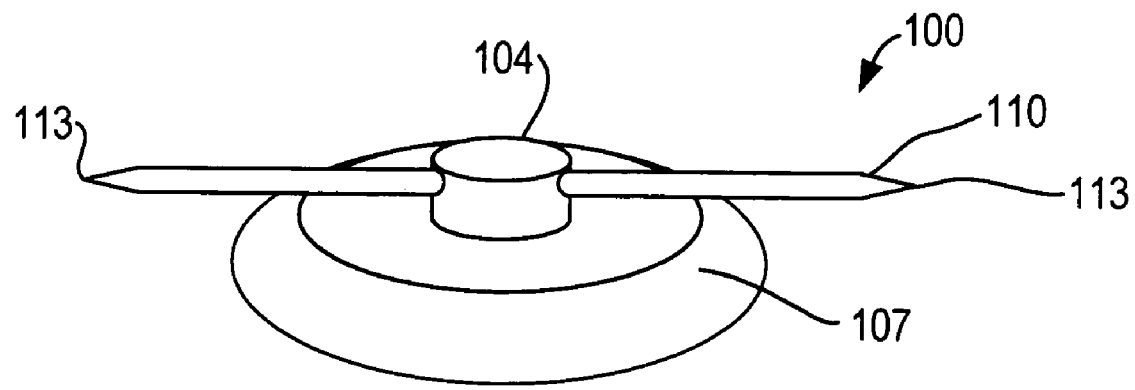

FIG. 9 shows magnet housing 107 with permanently fixed retentive prongs or struts 110. Wire-like struts 110 have free ends 113 that are mechanically, chemically, or electro-chemically sharpened. Struts 110 are designed to secure magnetic device 100 to the esophageal wall. Struts 110 can be made of any implantable structural material. Preferred materials include super-elastic metallic alloys such as nitinol. Struts 110 may be fixed to magnet housing 107 via methods that include (but are not limited to) interference fit, adhesive, solder, or braze between components. FIG. 9 shows two oppositely extending struts 110, but additional struts may be included if desired.

Figure 10:
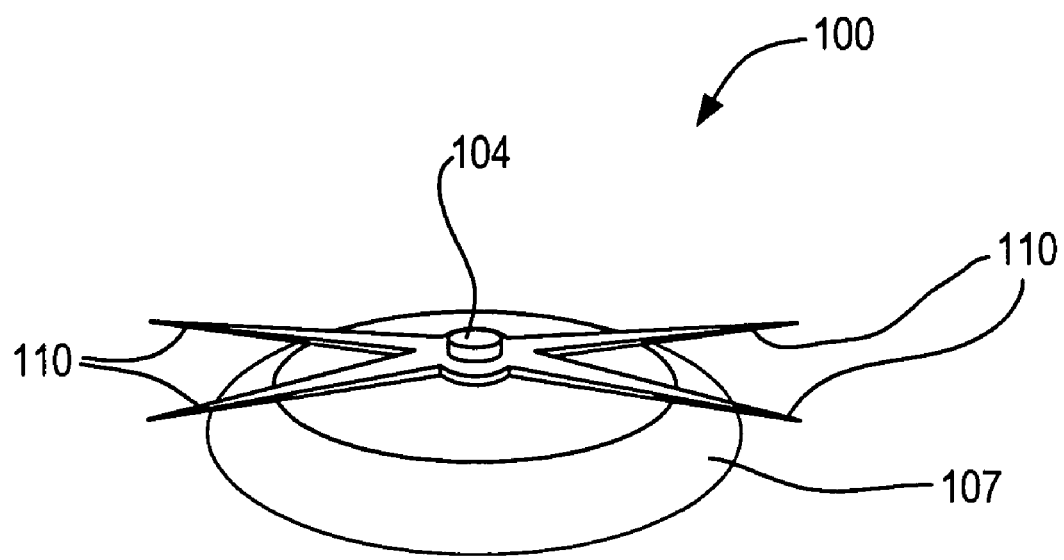

FIG. 10 is similar to FIG. 9, but shows an alternative embodiment of magnet housing 107 with retention struts 110 that are laser cut, electro-discharge machined, water jet cut, or photochemically etched from a sheet of metallic material. The retention struts are fixed to magnet housing 107 via interference fit, adhesive, solder, or braze between components.

Figure 11:
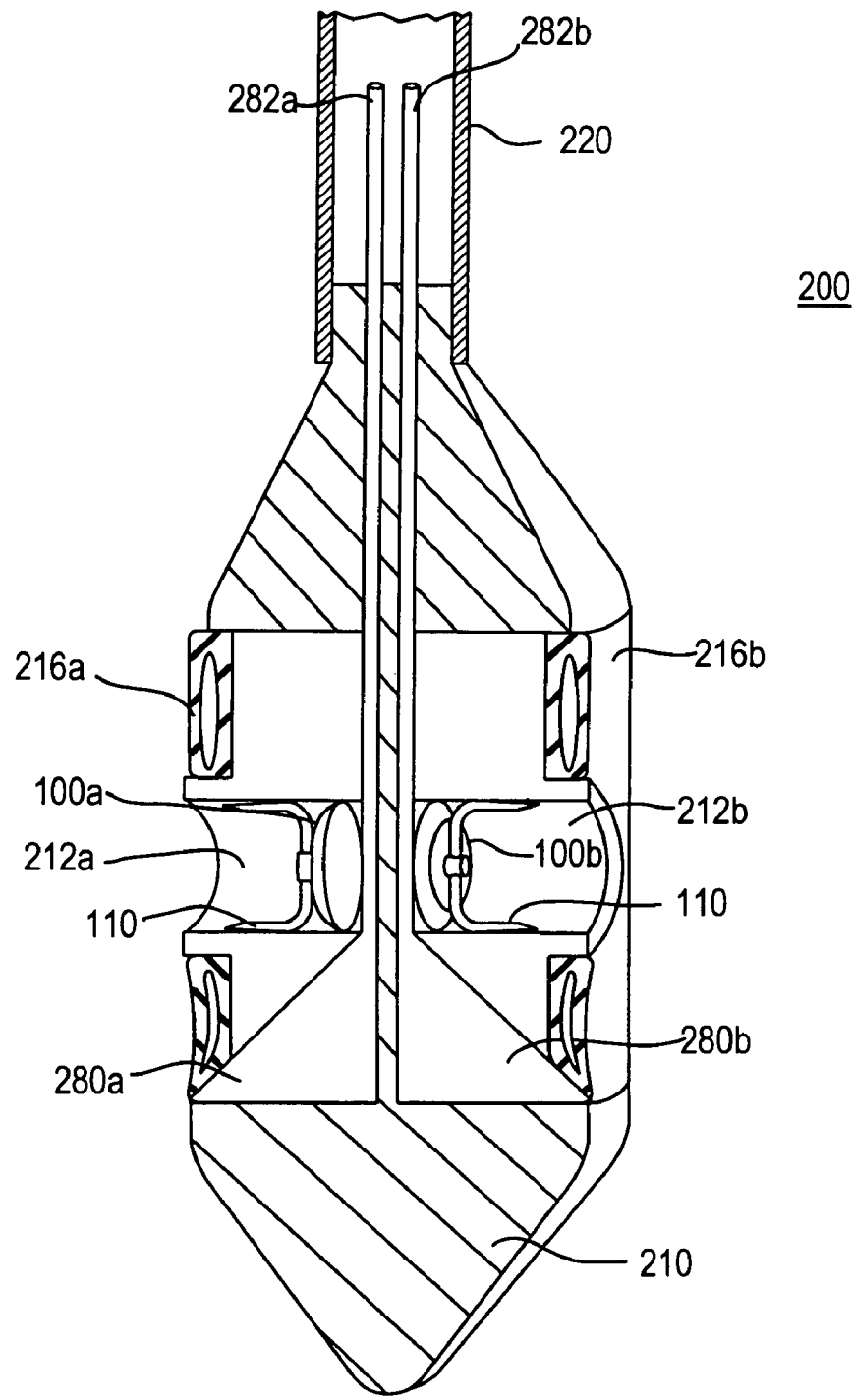
FIG. 11 is similar to FIG. 5 for yet another illustrative embodiment of the invention.

FIG. 11 shows an alternative embodiment of the distal portion 210 of deployment apparatus generally similar to that shown in FIGS. 3-5 and described above. The major difference between distal portion 210 in FIG. 11 and distal portion 210 in FIGS. 3 and 5 is that in FIG. 11 magnetic devices 100*a* and 100*b* are ejected from recesses 212*a* and 212*b* by mechanical means rather than by pressurized fluid as in FIGS. 3 and 5. In other respects the structure shown in FIG. 11 can be the same as the structure shown in FIGS. 3 and 5, and the structure shown in FIG. 11 can be used as the distal portion of a delivery system like that shown in FIG. 4. In order to adapt the FIG. 4 system for a distal portion as shown in FIG. 11, control elements 260 and 270 may be made mechanical actuators rather than pressurized fluid actuators. The lumens 218*a* and 218*b* that supply pressurized fluid to balloon structures 216*a* and 216*b* are not shown in FIG. 11 to simplify the drawing. The construction and operation of the FIG. 11 embodiment will now be described with reference to FIG. 11 and related FIGS. 12-19. It will not be necessary to exhaustively describe all details of these FIGS. because some of those details have already been described in connection with other embodiments.

FIG. 11 shows the initial condition of this embodiment of distal portion 210. Magnetic devices 210*a* and 210*b* are loaded in recesses 212*a* and 212*b*, respectively; balloon structures 216*a* and 216*b* are both deflated; and deployment wedges 280*a* and 280*b* are both below the level of recesses 212. Each of wedges 280 is a relatively thin triangular plate that can be pulled upwardly by an associated wedge pull wire 282*a* or 282*b*. When thus pulled upward, each wedge 280 can travel across the associated recess 212 because the side wall of each recess is open on both sides where the wedge will pass through. These slot-like openings in the side walls of each recess are either too narrow to permit escape of prongs 110 or prongs 110 are not aligned with those openings in order to prevent escape of the prongs.

Figure 12:
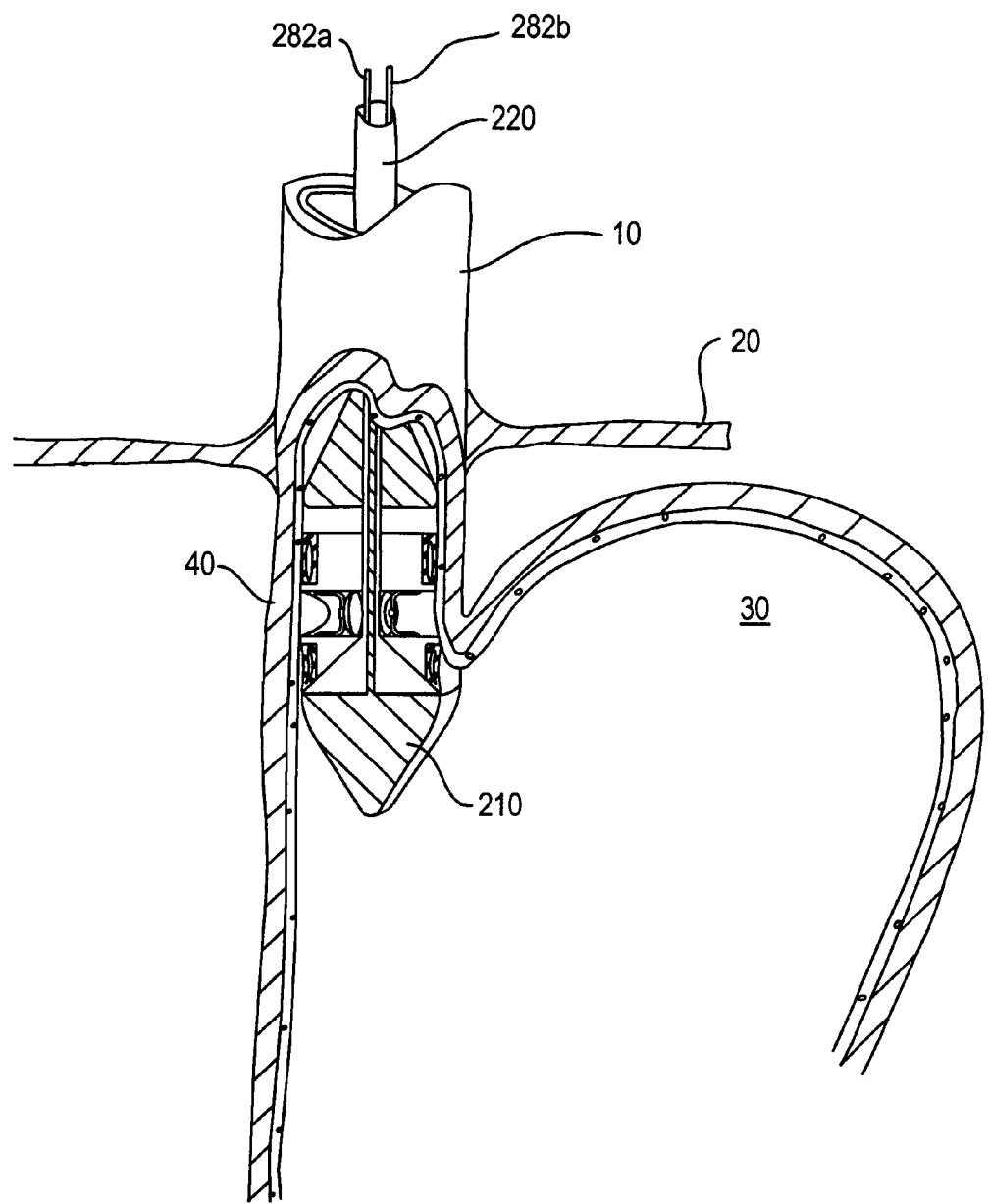
FIG. 12 shows a relatively early stage in use of the FIG. 11 apparatus in a patient's anatomy like that shown in FIG. 1 in accordance with the invention.

FIG. 12 shows positioning of distal portion 210 (of the type shown in FIG. 11) in a patient's esophagus 10 adjacent lower esophageal sphincter 40. The apparatus is now ready for further operation to implant magnetic devices 100*a* and 100*b* into the esophageal wall. The succession of operations performed to achieve this result are illustrated by the next several FIGS. and described below (although the presence of the esophageal tissue around the apparatus is not shown in all of these next FIGS.).

Figure 13:
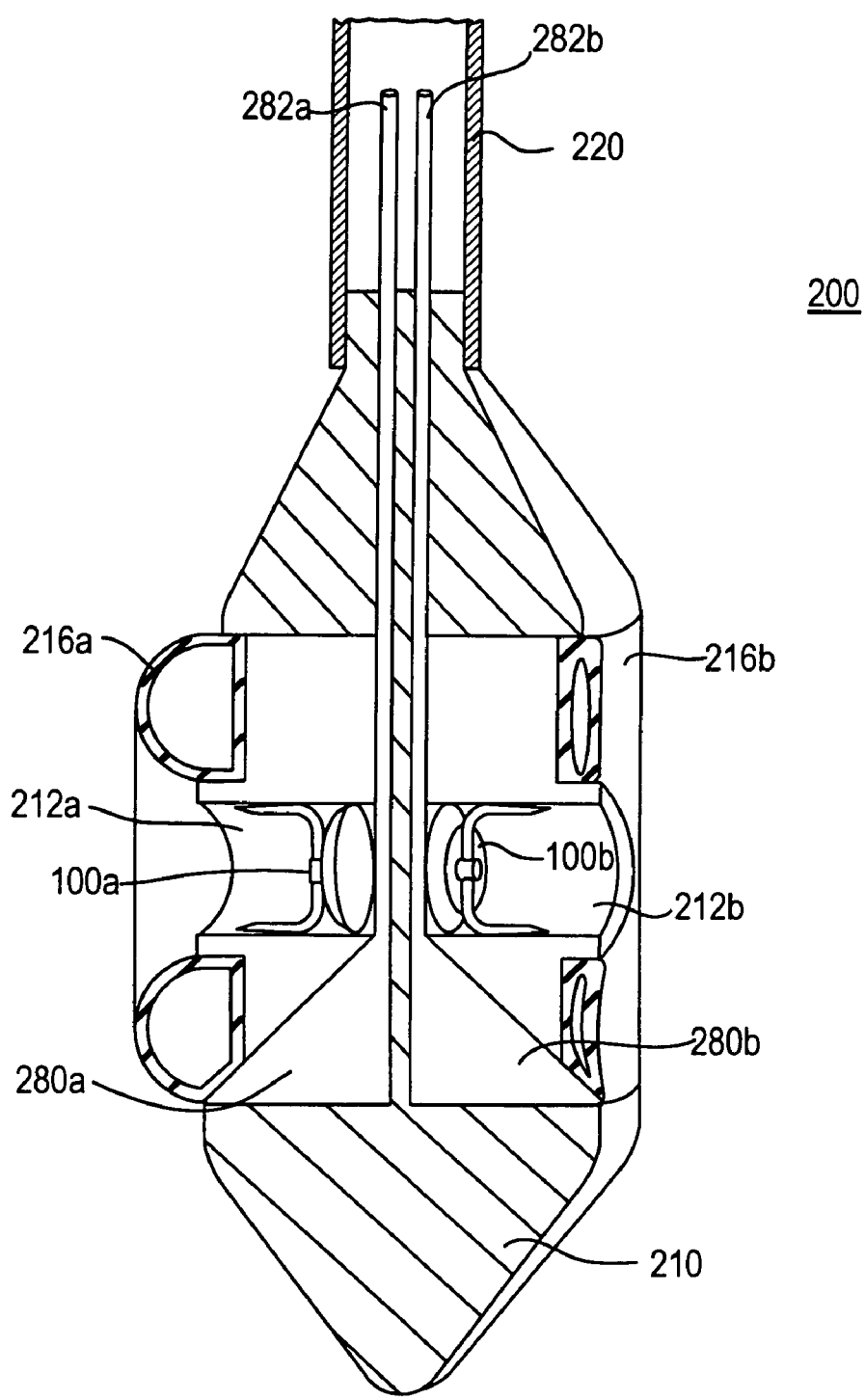
FIGS. 13, 14, 17, 18, and 19 are each similar to FIG. 11, but show successive stages in operation of the FIG. 11 apparatus in accordance with the invention.

FIG. 13 shows inflation of left side esophagus distention balloon structure 216*a*. This pushes the opposite (right) side of distal portion 210 more firmly against the opposite (right) side of the esophagus and ensures that the tissue on that opposite (right) side of the esophagus is stretched over the open end of right side recess 212*b*.

Figure 14:
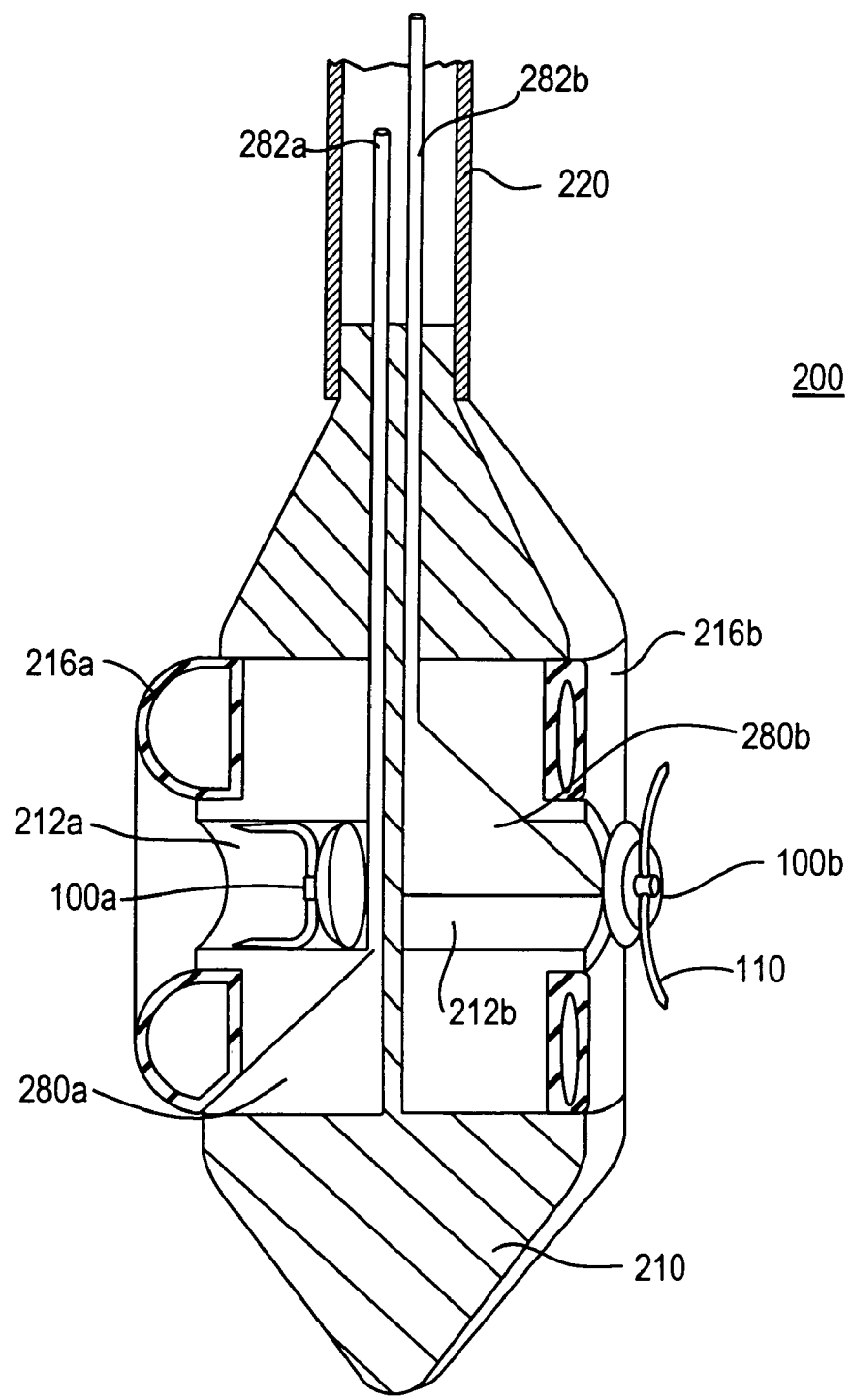
Figure 15:
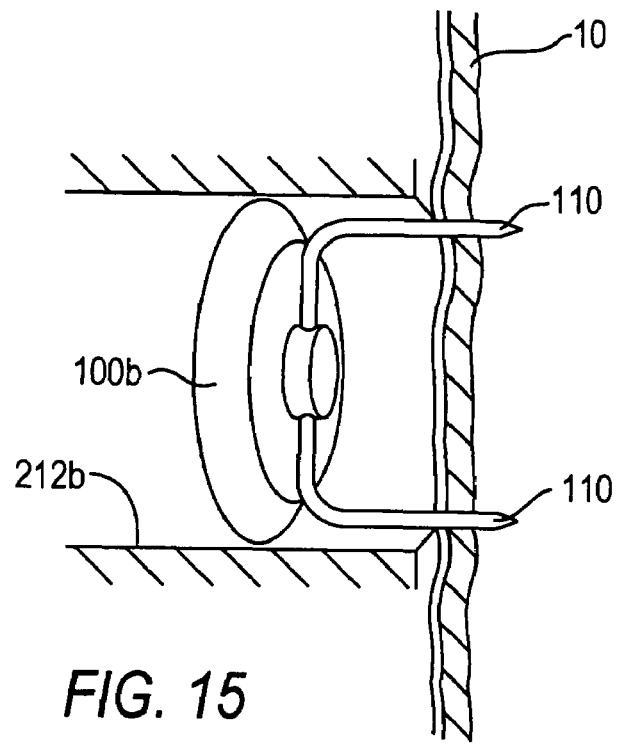
FIG. 15 is a simplified, partly sectional, perspective view showing a relatively early stage in implanting an illustrative magnetic device in a patient's tissue in accordance with the invention.
Figure 16:
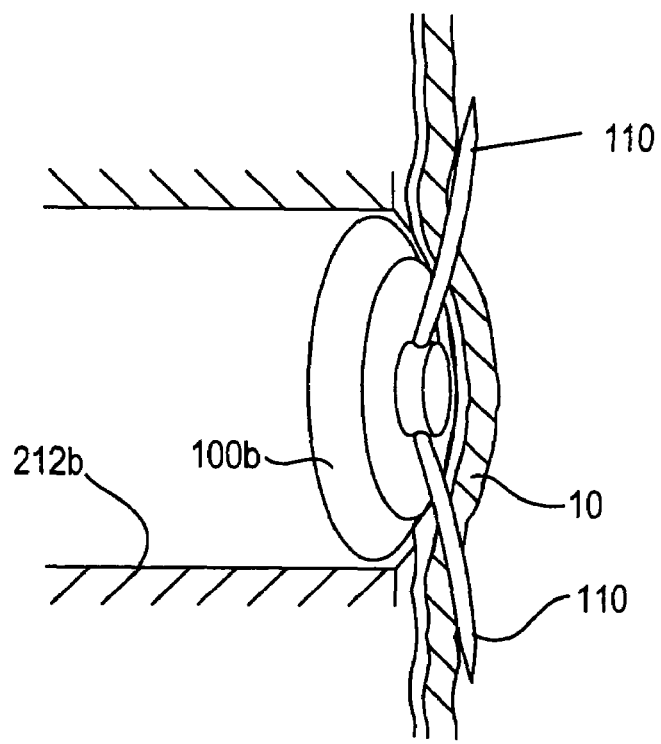
FIG. 16 is similar to FIG. 15 for a later stage in implanting the magnetic device in accordance with the invention.

In FIG. 14 balloon structure 216*a* is still inflated and right side deployment wedge 280*b* has been pulled up into recess 212*b* by proximal retraction of the associated right wedge pull wire 282*b*. Movement of deployment wedge 280*b* into recess 212*b* causes the inclined surface of the wedge to cam or wedge right side magnetic device 100*b* out of recess 212*b* and into the adjacent wall of the esophagus. Initial outward movement of magnetic device 100*b* in response to the above-described movement of deployment wedge 280*b* is shown in FIG. 15. During this initial movement, the free end portions of prongs 110 remain relatively parallel to one another (still constrained by recess 212*b*). Prongs 110 therefore at least begin to penetrate esophageal tissue 10 relatively parallel to one another. Final outward movement of magnetic device 100b in response to the above-described movement of deployment wedge 280b is illustrated by FIG. 16. Now prongs 110 are no longer constrained by recess 212b. Prongs 110 are therefore free to resiliently deflect toward their relatively relaxed positions in which they extend in opposite directions from one another into (and possibly even through) esophageal tissue 10. This "splayed apart" condition of prongs 110 in (and possibly through) tissue 10 secures magnetic device 100b to esophageal tissue 10.

Figure 17:
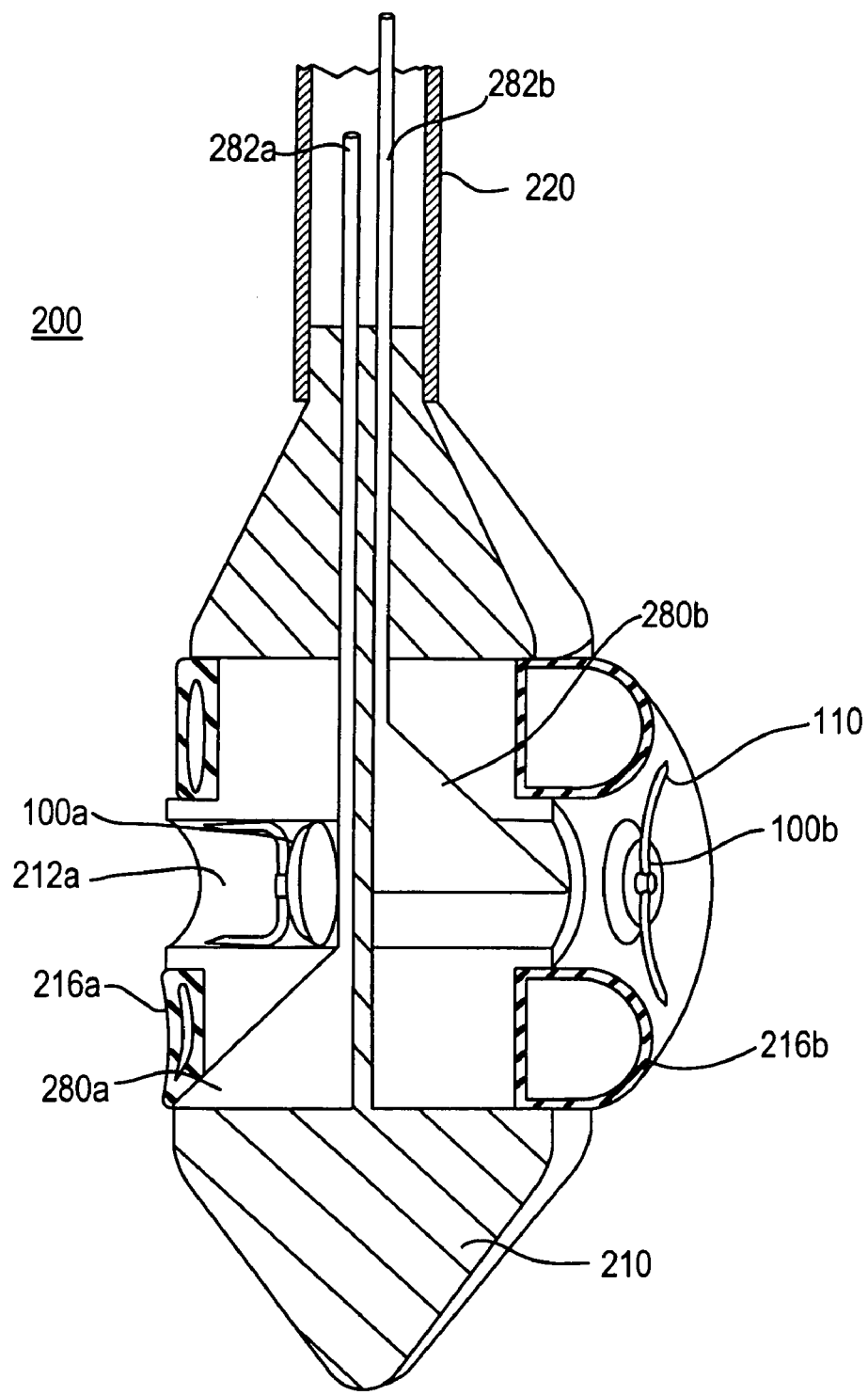

After right side magnetic device 100b has been deployed as described above, left side esophagus distention balloon structure 216a is deflated and right side esophagus distention balloon structure 216b is inflated as shown in FIG. 17. This pushes distal portion 210 more firmly against the left side of the esophagus and ensures that the tissue of the esophagus is stretched across the entrance to left side recess 212a.

Figure 18:
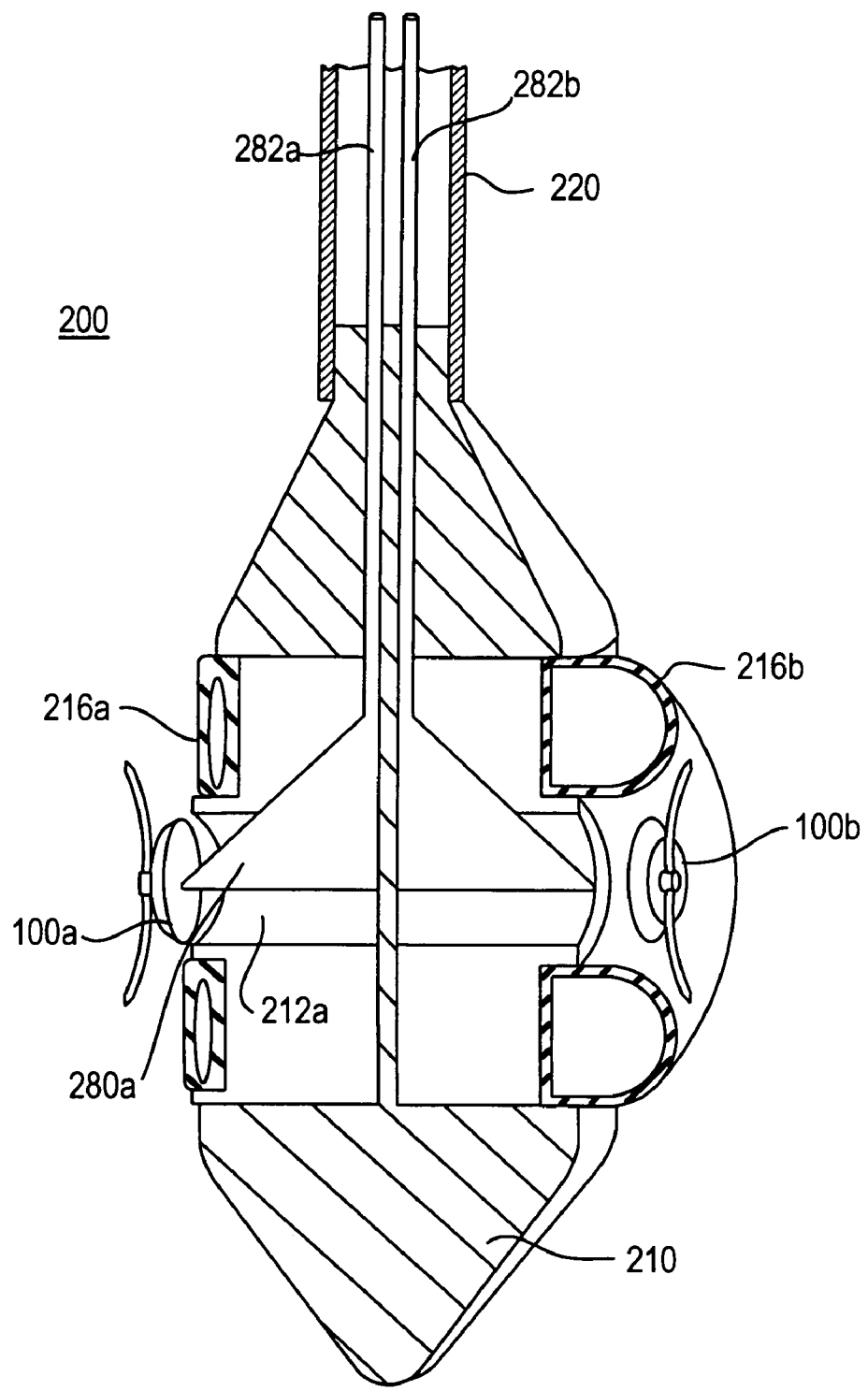

As shown in FIG. 18, the next step is to raise left side deployment wedge 280a by pulling, proximally on left side wedge pull wire 282a. This causes left side deployment wedge 280a to enter recess 212a, thereby driving left side magnetic device 100a out of that recess and into the adjacent wall of the esophagus (in the same way that right side deployment wedge 280b earlier drove right side magnetic device 212b out of recess 212b and into the tissue on the opposite side of the esophagus).

Figure 19:
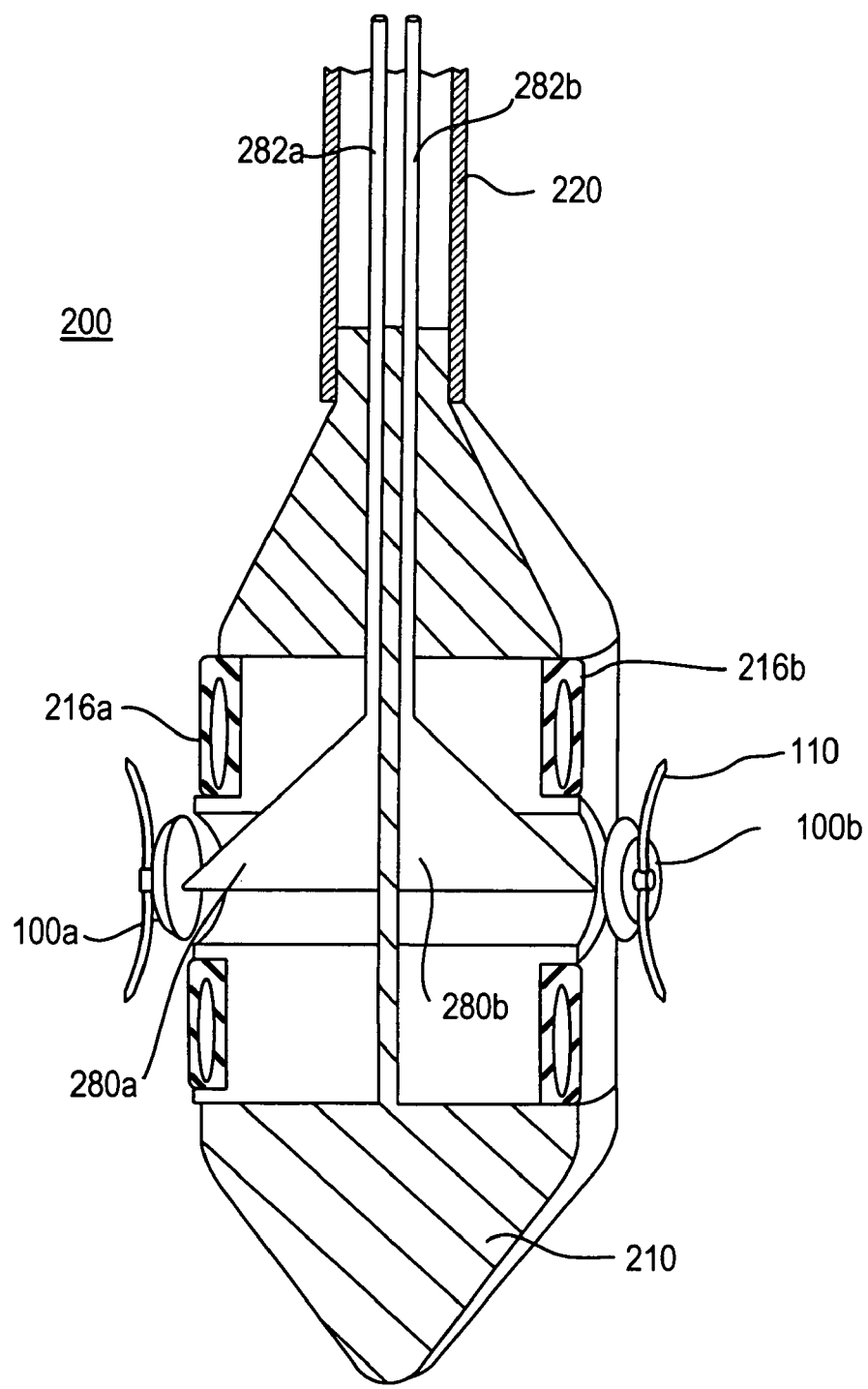

After left side magnetic device 100a has been deployed, balloon structure 216b is deflated as shown in FIG. 19. The entire apparatus 200 (exclusive of magnetic devices 100) can now be removed from the patient, and the final condition of the patient's esophagus will be as shown in FIG. 2.

It will be understood that the order in which devices 100a and 100b are deployed is entirely a matter of choice. The particular order shown and described above is merely exemplary.

Figure 20:
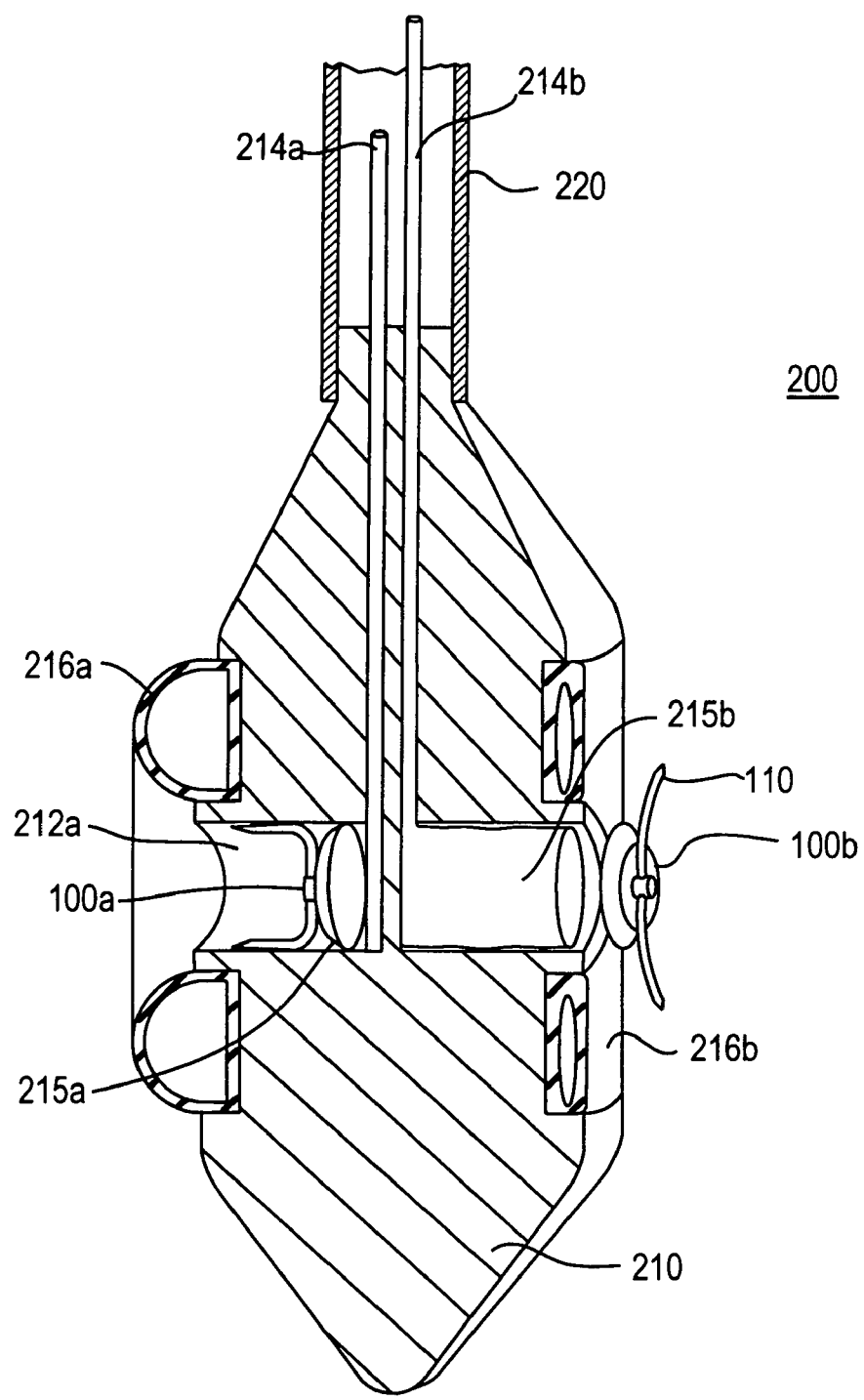
FIGS. 20-22 are views similar to FIG. 14 for still more illustrative embodiments of apparatus in accordance with the invention.

FIG. 20 shows another illustrative embodiment of the distal portion 210 of illustrative deployment system 200. In this embodiment each of recesses 212a and 212b contains an inflatable structure 215a or 215b behind the magnetic device 100 in that recess. Each inflatable structure 215 is in fluid communication with a respective one of inflation lumens 214a and 214b (like the similarly numbered lumens 214a and 214b in FIG. 3 or FIG. 5). When it is desired to eject one of magnetic devices '100 from the associated recess 212, the inflatable structure 215 behind that device is inflated by supplying pressurized fluid to the lumen 214 connected to that inflatable structure. This causes the inflatable structure 215 to inflate, thereby forcing the associated magnetic structure 100 out of the associated recess 212. For example, FIG. 20 shows balloon structure 216a inflated, as is appropriate in preparation for ejection of magnetic device 100b. And FIG. 20 shows inflation of inflatable structure 215b and resulting ejection of magnetic device 100b. It will be understood that what is shown in FIG. 20 can be used as the distal portion of a more complete deployment system like that shown in FIG. 4. It will also be understood that FIG. 20 omits (to avoid complicating the drawing) the lumens 218 (e.g., FIG. 3 or FIG. 5) that are typically provided for inflation of balloon structures 216. Examples of suitable materials for inflatable members 215 include (but are not limited to) silicone, PET, Pebax, nylon, latex, and polyurethane.

Figure 21:
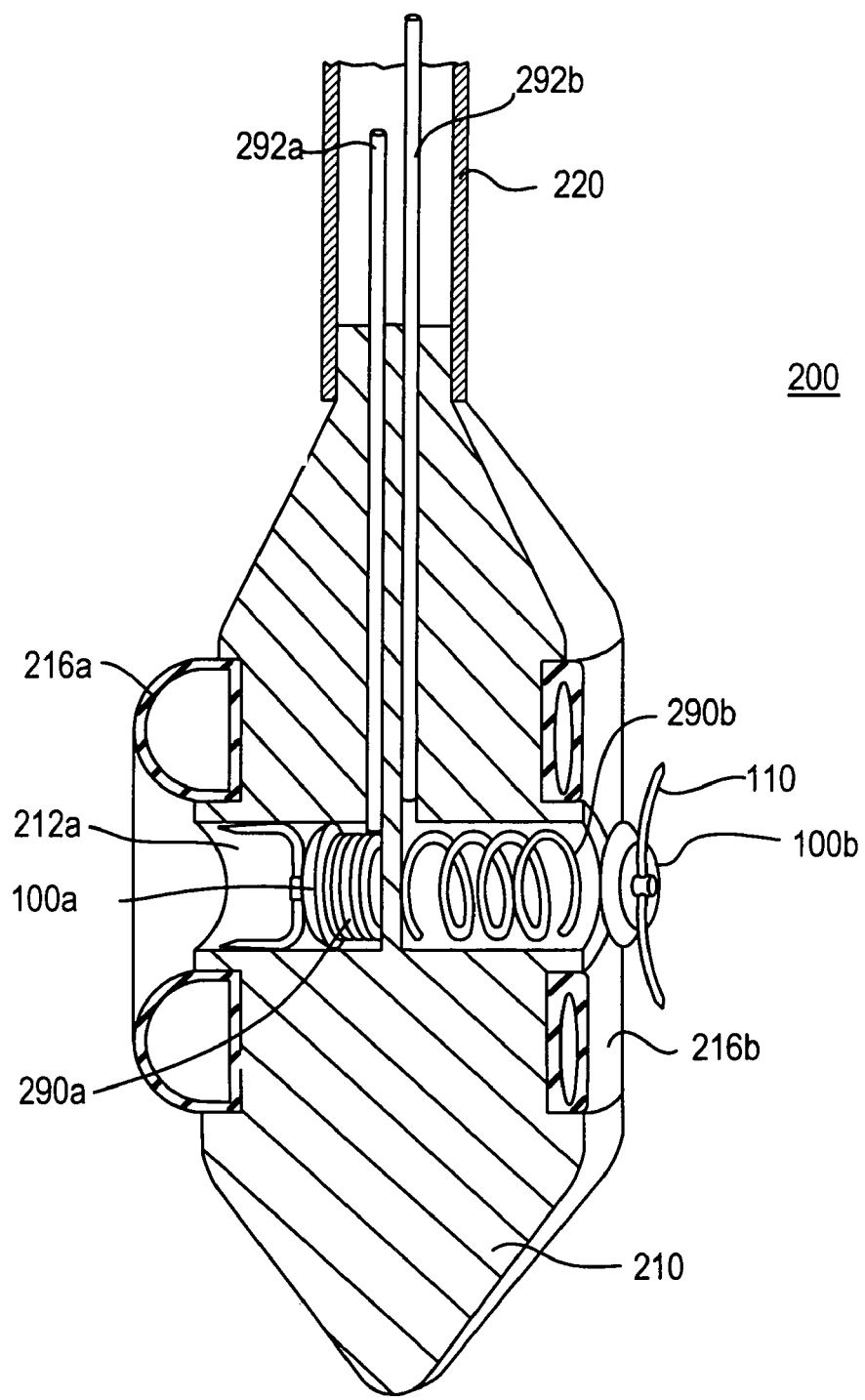

FIG. 21 shows another illustrative embodiment of distal portion 210 of illustrative deployment system 200. In this embodiment, a pre-stressed compression coil spring 290a or 290b is disposed behind each magnetic device 100a or 100b, respectively. Each spring 290 is releasably held in its compressed condition by a structure that includes release wire 292a or 292b. When it is desired to release a spring 290 so that it can eject the associated magnetic device, the release wire 292 for that spring is pulled in the proximal direction. For example, FIG. 21 shows the elements 290a and 292a (on the left) prior to proximal retraction of release wire 292a. Magnetic device 100a is therefore undisturbed in recess 212a. On the right, however, release wire 292b has been proximally retracted. Spring 290b has therefore been released to expand and drive magnetic device 100b out of recess 212b. Any of a wide range of spring and release mechanisms can be used in embodiments of the general type illustrated by FIG. 21. Again, the lumens for inflating balloon structures 216 have not been shown in FIG. 21 to simplify the drawing. Also, it will again be understood that the distal portion 210 shown in FIG. 21 can be the distal portion of the deployment system 200 shown more completely in FIG. 4. This is simply a matter of configuring ejection control elements 260 and 270 in FIG. 4 appropriately to proximally retract release wires 292 when it is desired to eject magnetic devices 100.

Figure 22:
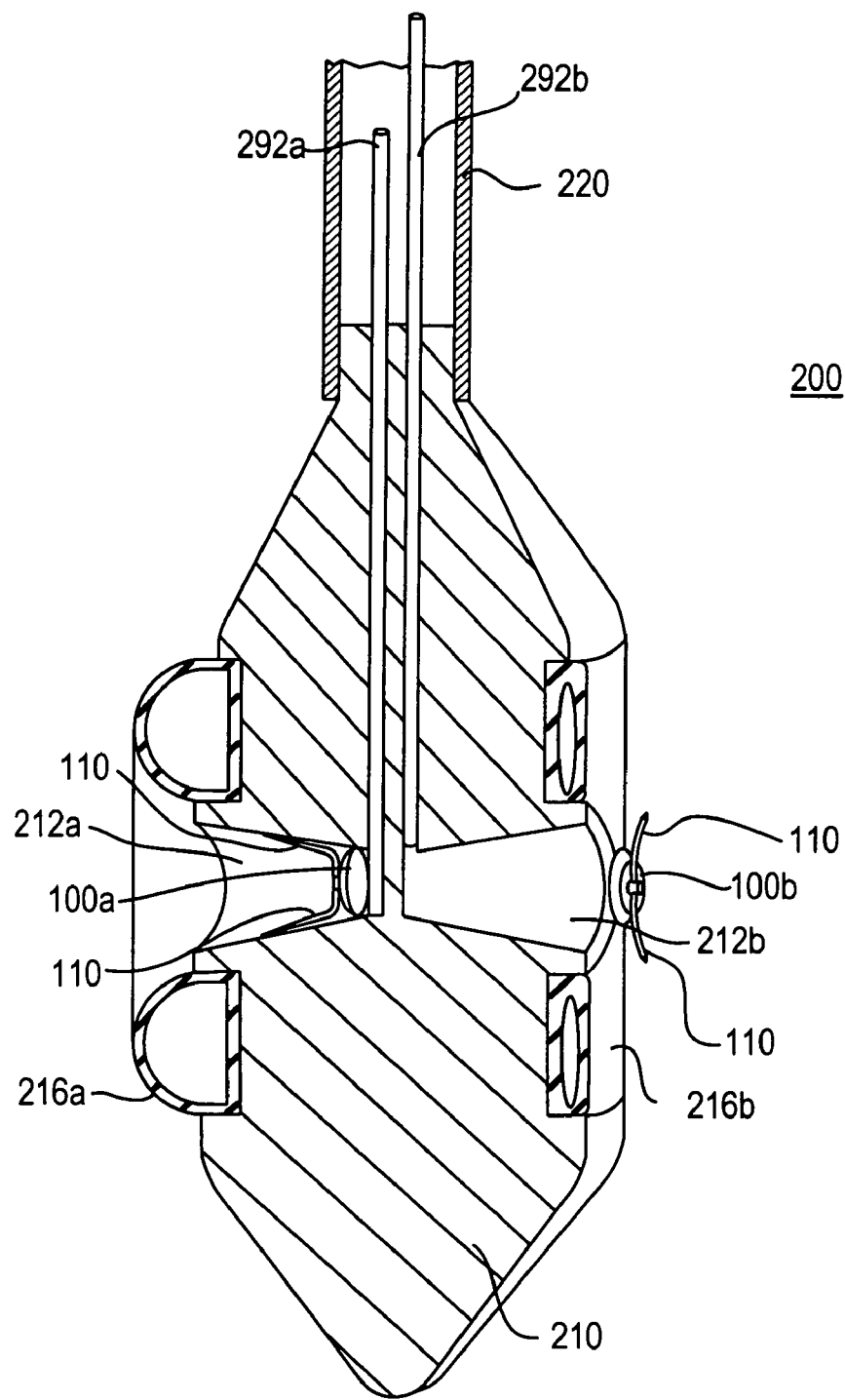

FIG. 22 shows another alternative embodiment of distal portion 210 in which at least portions of the side wall of each recess 212 are inclined away from one another in the direction from the bottom of the recess toward the open end of the recess. The resilient prongs 110 of the magnetic device 100 in each recess engage these anticlinal recess wall surfaces in such a way that the spring force of the prongs tends to eject the magnetic device from the recess. Initially, however, each magnetic device 100 is held in its recess 212 by an associated release wire 292a or 292b, which releasably engages the magnetic device. This releasable engagement can be mechanical (e.g., release wire extending into or through a recess or hole in magnetic device), magnetic (e.g., magnetic device magnetically attracted to ferromagnetic release wire), or the like. When it is desired to eject a magnetic device 100 from its recess, the release wire 292 for that magnetic device is pulled proximally (as shown on the right in FIG. 22). The spring force of prongs 110 acting on the anticlinal recess wall surfaces ejects the associated magnetic device from the recess and implants the magnetic device in the esophageal wall tissue. Once again, what is shown in FIG. 22 can be the distal portion 210 of a more complete delivery system like that shown in FIG. 4. Also, the lumens for use in inflating balloon structures 216 are omitted from FIG. 22 to simplify the drawing.

Figure 23:
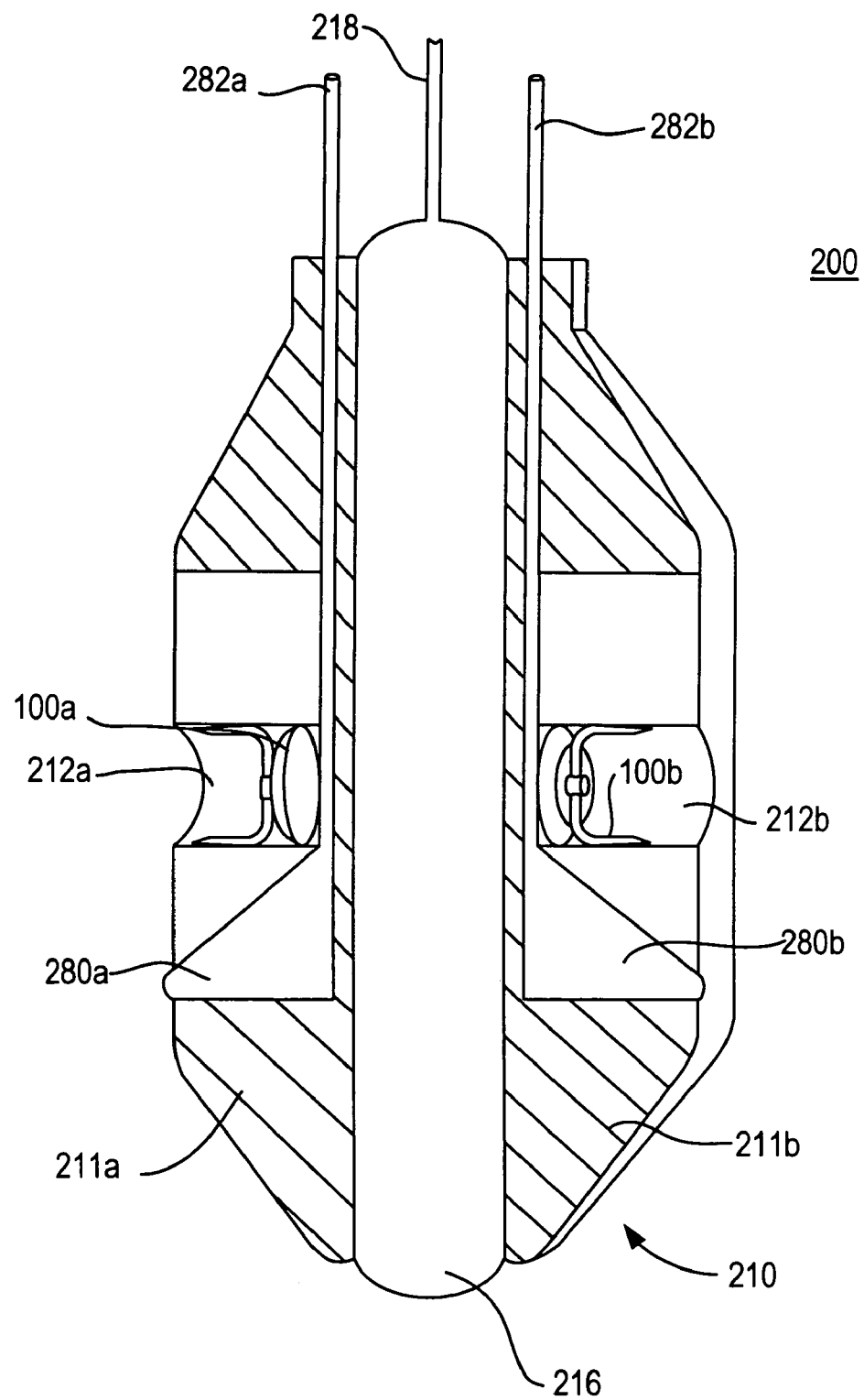
FIG. 23 is a view similar to FIG. 11 for yet another illustrative embodiment of apparatus in accordance with the invention.

FIG. 23 shows another alternative embodiment of distal portion 210 of a deployment system which produces distention of the esophagus prior to ejection of magnetic devices 100 in another way. In this embodiment the left (211a) and right (211b) parts of the main body of distal portion 210 are separated from one another by an inflatable (e.g., balloon or balloon-like) structure 216. For example, left and right parts 211a and 211b may be secured to respective opposite sides of inflatable structure 216. Distal portion 210 is initially positioned in the patient with structure 216 deflated and with parts 211a and 211b relatively close to one another. When it is time to eject magnetic devices 100 from recesses 212, structure 216 is inflated as shown in FIG. 23 by supplying pressurized fluid to structure 216 via inflation lumen 218. This distends the patient's esophagus, pressing both sides of distal portion 210 more firmly against the esophagus and stretching the esophageal tissue over the entrances to recesses 212a and 212b. Magnetic devices 100 are then ejected and implanted by proximally retracting wedge pull wires 282 in order to raise deployment wedges 280 (similar to what is shown in FIGS. 11-19 and described above). In this embodiment both of magnetic devices 100 can be driven at the same time, or they can be driven one after the other as in the earlier described embodiments. If the distal portion 210 of FIG. 23 is used in a system like that shown in FIG. 4, only one element like 240/250 is needed because one inflatable structure 216 does all the final lateral positioning of the distal components. Similarly, if both of magnetic devices 100 are driven at the same time, it may be possible to include only one element like 260/270 in a system of the FIG. 4 type because both of deployment wedges 280 are going to be operated at the same time by what can be a common control.

Although FIG. 23 shows, wedge, deployment of magnetic devices 100, any of the other types of magnetic device deployment taught herein can instead be used in a system that is otherwise like what is shown in FIG. 23 if desired. For example, pressured fluid deployment as shown in any of FIGS. 3, 5, or 20 can be used. Or spring-powered deployment like that shown in FIG. 21 or 22 can be used.

Figure 24:
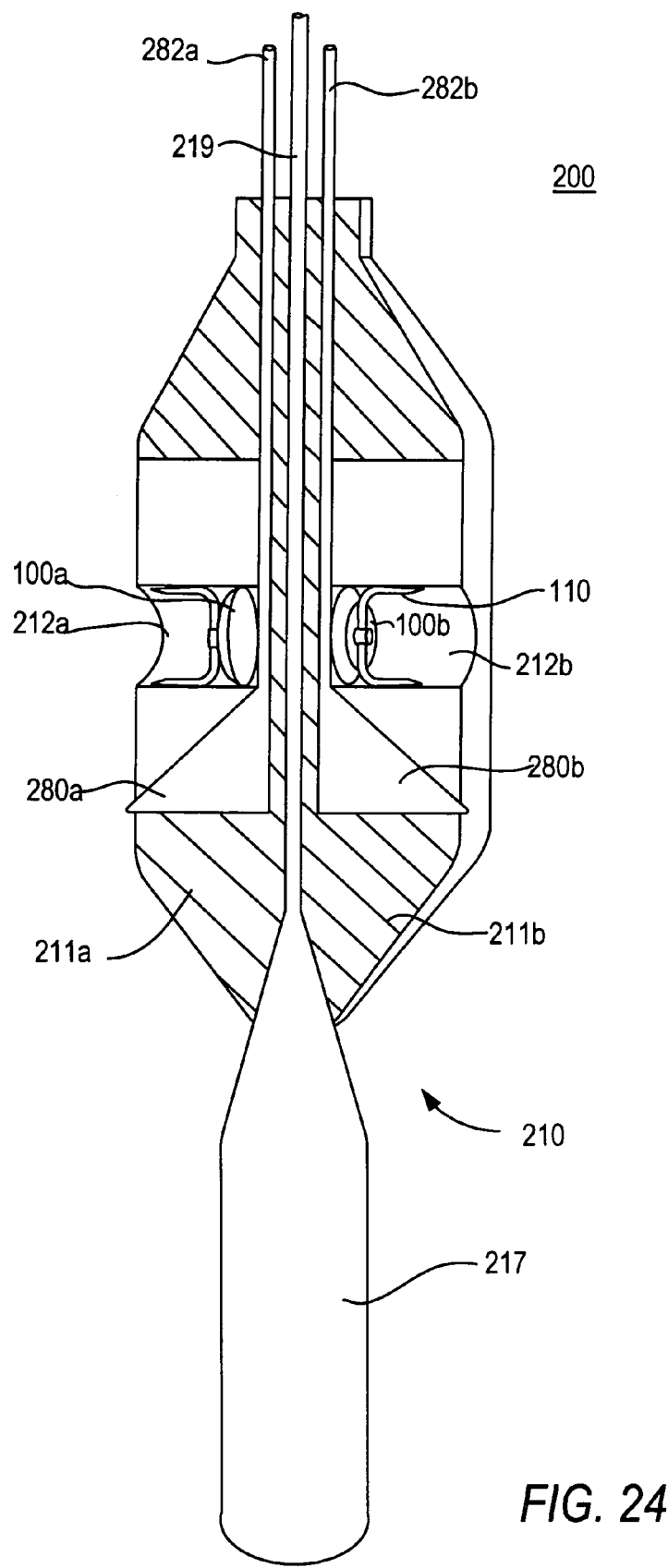
FIG. 24 is a view similar to FIG. 23 for still another illustrative embodiment of apparatus in accordance with the invention.
Figure 25:
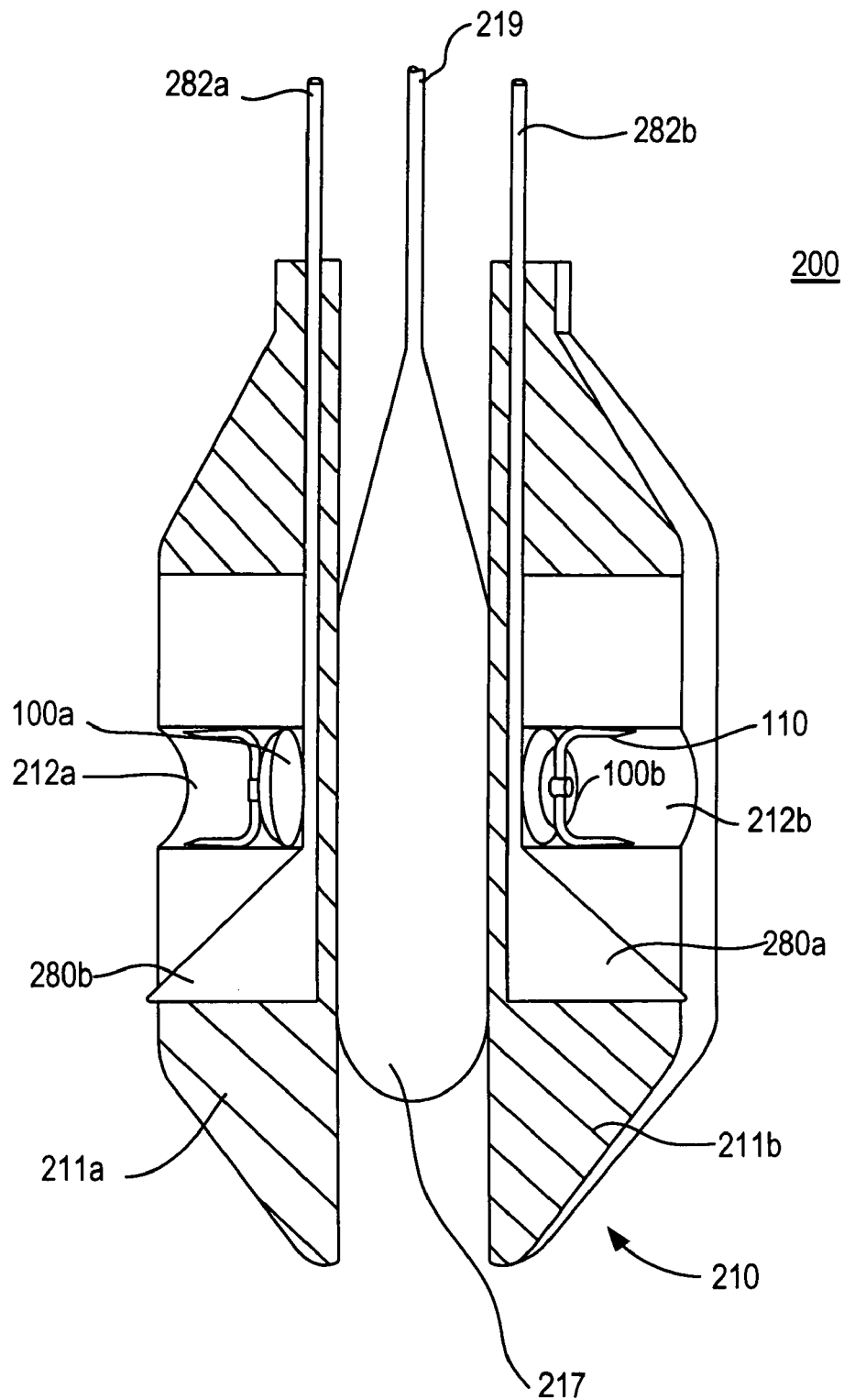
FIG. 25 shows a later stage in use of the FIG. 24 apparatus.

Still another illustrative embodiment of distal portion 210 is shown in FIGS. 24 and 25. This embodiment is somewhat like the FIG. 23 embodiment, except that in this case the left (211a) and right (211b) parts of distal portion 210 are separated (when desired) by pulling shim structure 217 proximally back between them as shown in FIG. 25. In other words, the structure is first positioned in the patient in a condition like that shown in FIG. 24 with shim structure 217 distal of separable parts 211a and 211b. Then to finally prepare for deployment of magnetic devices 100, shim structure 217 is pulled proximally back between those parts as shown in FIG. 25 by pulling shim pull wire 219 proximally. This distends the tissue in the same way that inflation of structure 216 in FIG. 23 distends the tissue. With the tissue thus distended, magnetic devices 100 can be deployed in the same way that has been described above in connection with FIG. 23. Shim structure 217 can be a basically cylindrical body with one end portion tapered and the other end portion rounded. Variations and modifications suitable for embodiments like that shown in FIG. 23 are also suitable for the FIGS. 24 and 25 embodiments. Similarly, modifications of what is shown n FIG. 4 for use with FIG. 23 are also possible for FIGS. 24 and 25 embodiments.

Figure 26:
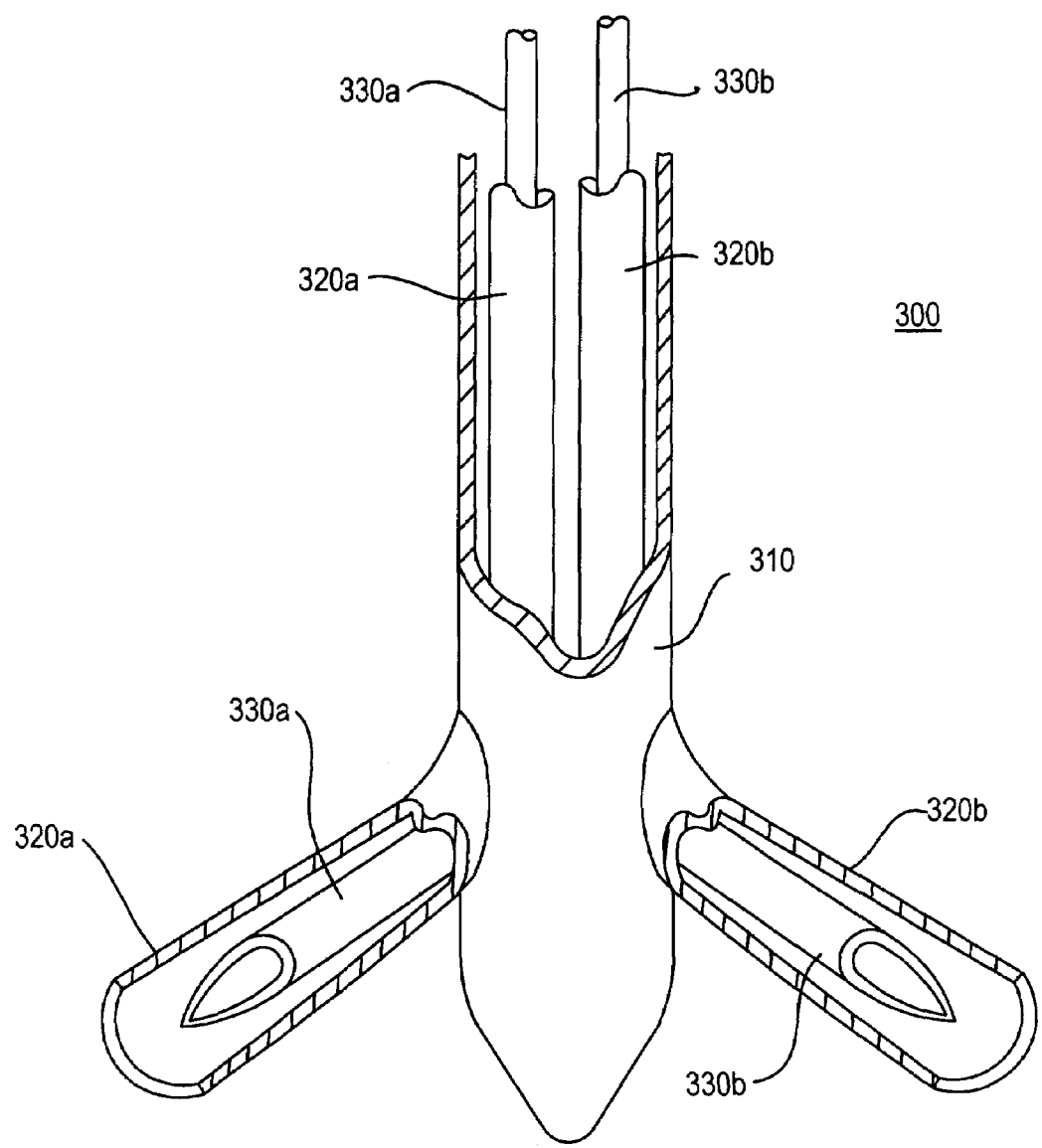
FIG. 26 is a simplified, partial, elevational view (partly in section) of an illustrative embodiment of still more apparatus in accordance with the invention.

In some embodiments of the invention it may be desirable to first mark the wall of the esophagus with marks that facilitate later observation (e.g., visualization) of the esophagus, and especially the points on the esophagus to which magnetic devices 100 are to be applied. FIG. 26 shows the distal portion of an illustrative embodiment of marking apparatus 300 in accordance with the invention. This apparatus is designed for delivery of its distal portion into a patient's esophagus via the patient's mouth.

Marking apparatus 300 includes main delivery catheter 310. One or more secondary catheter-like tubes 320a and 320b are selectively extendable from the side wall of main delivery catheter 310. Typically, main delivery catheter 310 is introduced into the patient with secondary tubes 320 retracted into the main catheter. When main catheter 310 is properly positioned in the patient, secondary tubes 320 are extended from the main catheter to somewhat distend and press against the side wall of the esophagus at the locations that are to be marked. Then a marking element 330a or 330b is extended from each secondary tube 320. For example, each marking element 330 may include a needle for injecting visible and/or radiopaque dye, an electrically conductive wire for the transmission of radio frequency energy, a structure for performing argon plasma cautery, or a lumen for transmission of vacuum (to visibly redden the tissue surface by drawing extra blood to it).

Figure 27:
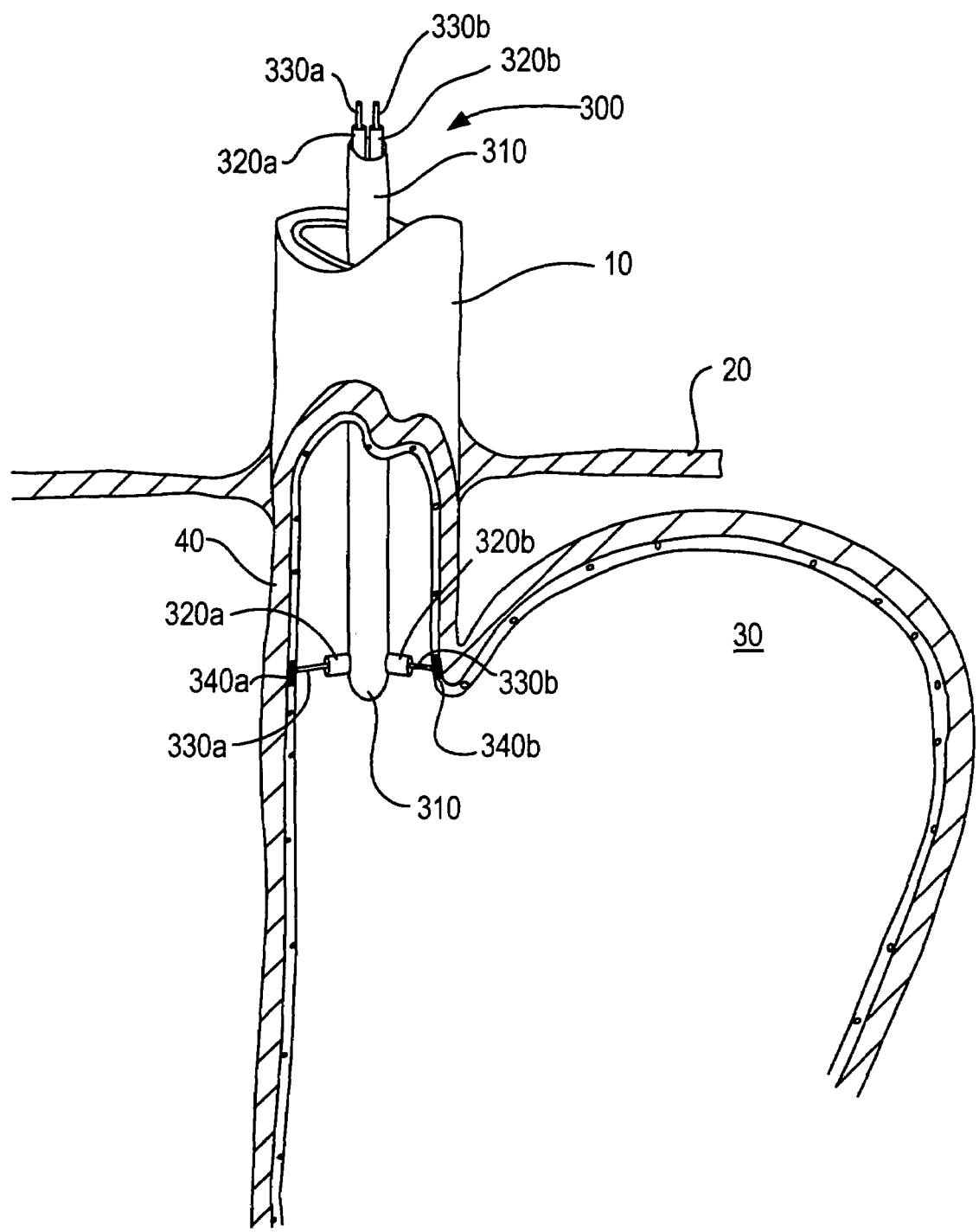
FIG. 27 is a view similar to FIG. 12 showing use of the FIG. 26 apparatus in accordance with the invention.

FIG. 27 shows the distal-most portion of esophagus marking apparatus 300 positioned at the level of the lower esophageal sphincter 40. Esophagus marking elements 330a and 330b have been extended substantially radially and marks 340a and 340b have been placed on the surface or internal to the esophageal wall.

After marks 340a and 340b have been applied, apparatus 300 can be removed from the patient by pulling it out of the patient's mouth. Marks 340a and 340b can thereafter be used to help guide proper placement of magnetic devices in the patient. Marks 340 can be observed visibly, radiologically, or in any other way that is suitable in view of the type of marks and the other apparatus employed. Any of the previously shown and described magnetic device deployment apparatuses and methods can be used with marking methods and apparatus such as have just been described. The same is true for any of the other magnetic device implanting methods and apparatuses that will be described later in this specification.

Marking apparatus 300 typically includes proximal components (not shown) that remain outside the patient at all times and that are used for controlling the depicted distal portions of the apparatus. Although these proximal components are not shown, they may be generally in the nature of the proximal componentry shown in FIG. 4, i.e., a control element for axially positioning main catheter 310 in the patient, one or more control elements for shifting secondary tubes 320 axially relative to main catheter 310, one or more control elements for shifting marking structures 330 axially relative to tubes 320, and one or more control elements for controlling marking structures 330 to actually produce marks 340.

Figure 28:
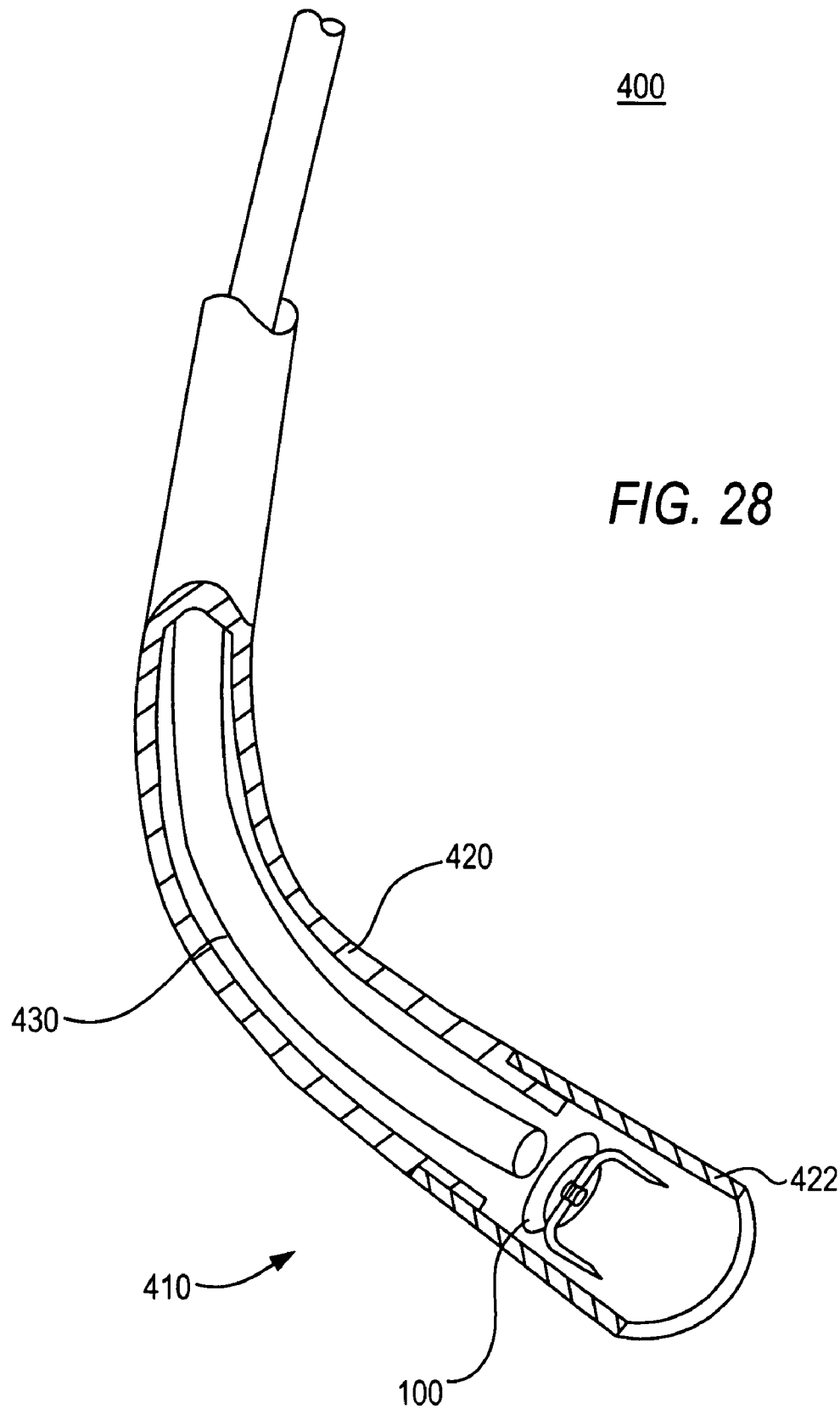
FIG. 28 is a simplified, partial, perspective view (partly in section) of still more illustrative apparatus in accordance with the invention.

FIG. 28 shows the distal portion 410 of another illustrative embodiment of apparatus 400 for implanting a magnetic device 100 in the esophagus of a patient. Apparatus 400 includes elongated, hollow, delivery catheter 420, which is insertable into the patient's esophagus via the patient's mouth. Like other delivery catheter structures described earlier in this specification, delivery catheter 420 is sufficiently flexible to pass through the mouth and down the esophagus, but it also has sufficient column strength that it can be pushed down the esophagus without folding back on itself undesirably. The extreme distal end portion of catheter 420 includes magnetic device holder 422 (e.g., a short, hollow tube for holding magnetic device 100 with the resilient prongs 110 of that device deflected). Inside of catheter 420 is a structure 430 for ejecting magnetic device 100 from holder 422 when it is desired to implant the magnetic device in the tissue of the patient. The relatively distal portion of one or more of structures 420 and 430 may include some "steerability," i.e., capability of being controllably deflected laterally or transversely relative to the main longitudinal axes of the apparatus and the patient's esophagus. Such steerability allows the distal end of structure 420/422 to be laterally deflected toward the side wall of the esophagus when the apparatus is properly positioned in the patient and it is desired to drive magnetic device 100 into the esophageal wall tissue. This lateral deflection of the apparatus may also be used to distend the esophagus and thereby help to press the free end of structure 422 more firmly against the esophageal wall.

Figure 29:
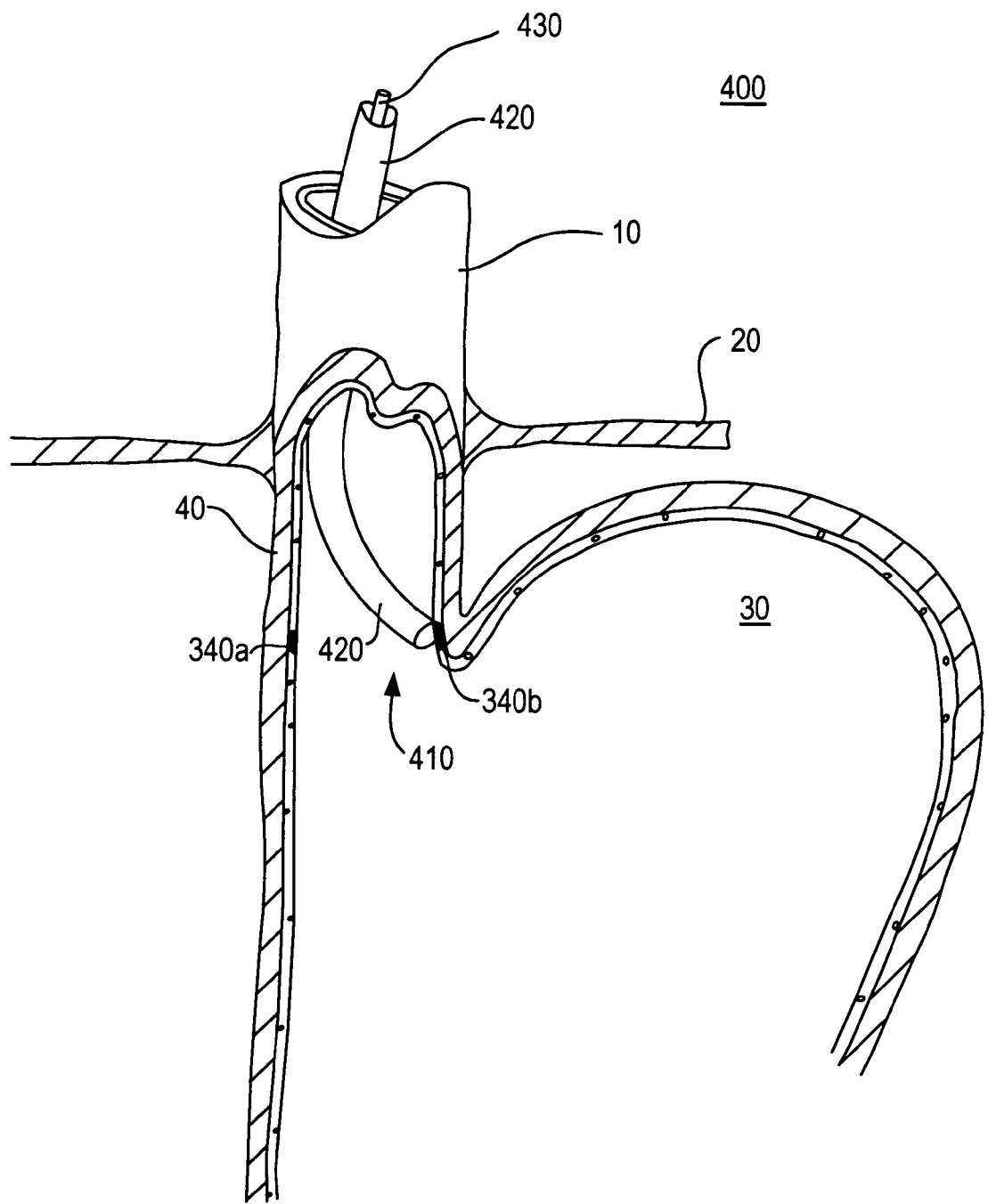
FIG. 29 is similar to FIG. 27 showing use of the FIG. 28 apparatus in accordance with the invention.

FIG. 29 shows apparatus 400 inserted in a patient's esophagus and with distal portion 410 steered laterally toward previously applied mark 340b. Note that (as suggested above) an effect of this laterally steering is to brace an intermediate portion of structure 420 against the wall of esophagus 10 opposite mark 340b so that the free end of structure 420 will be pressed against the tissue at mark 340b. When the apparatus is in a condition like that shown in FIG. 29, magnetic device ejection structure 430 can be operated to drive magnetic device 100 from structure 420/422 into the patient's esophageal wall tissue at mark 340b.

Ejection structure 430 can be (or represent) any of a wide range of components for driving magnetic device 100 from the surrounding structure 422. For example, ejection structure 430 can be a mechanical pusher. Or structure 430 can be (or represent) structure for achieving ejection of magnetic device 100 by means of pressurized fluid. As still another example, ejection can be by any of the above-described releasable spring methods or apparatus, and structure 430 can represent the required spring and/or spring release components.

After magnetic device 100 has been implanted at mark 340b, apparatus 400 can be withdrawn from the patient via the patient's mouth. Any lateral steering of apparatus 400 can be relaxed during withdrawal to facilitate such withdrawal. Reloaded apparatus 400 or a second similar apparatus can then be inserted into the patient to install a second magnetic device 100 at mark 340a.

Again, although not shown in the FIGS., apparatus 400 typically includes various control components that remain outside the patient at all times. These control components can generally be like appropriate ones of the control components shown in FIG. 4. The control components that will generally be needed will be components for controlling (1) longitudinal placement of distal portion 410 in the patient's esophagus, (2) lateral steering of distal portion 410, and (3) ejection of magnetic device 100.

Figure 30:
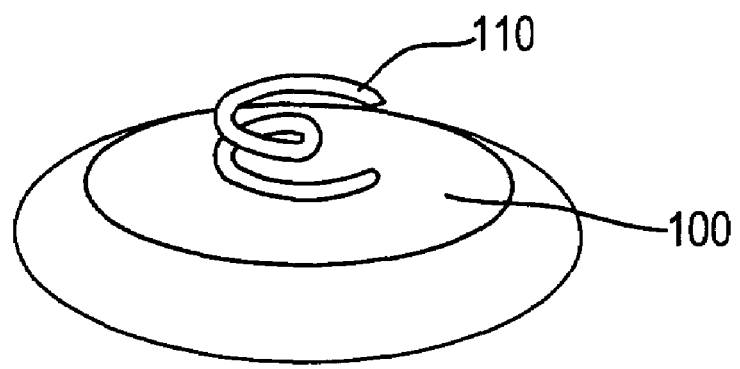
FIGS. 30-33 are views similar to FIGS. 8-10 for still more illustrative embodiments of implantable devices in accordance with the invention.
Figure 31:
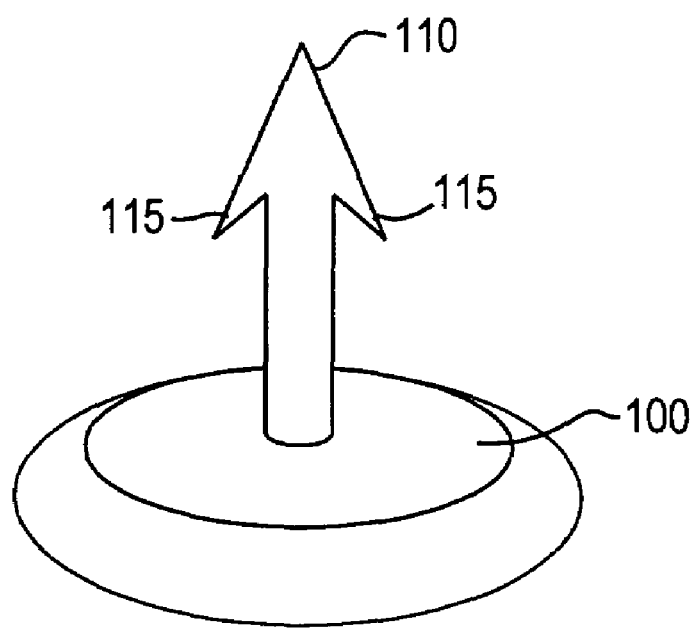
Figure 32:
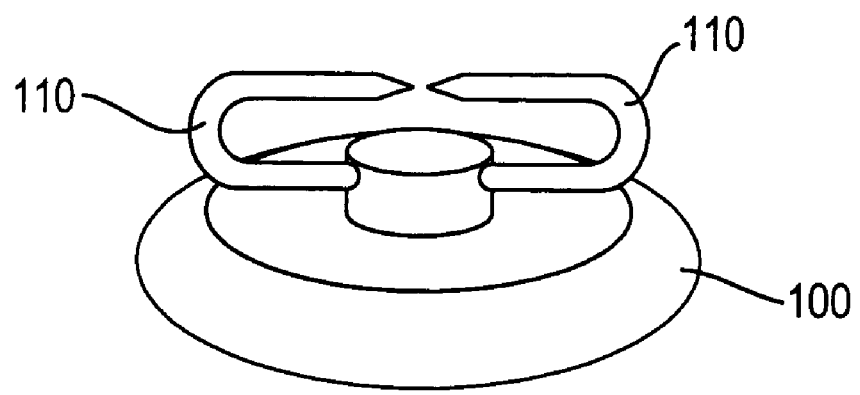

Some illustrative alternative embodiments for retention structures 110 for securing a magnetic device 100 to a patient's tissue are shown in FIGS. 30-32. In FIG. 30 retention structure 110 is configured as or like a helical spring extending from the main body of magnetic device 100. The free end of spring 110 is preferably sharpened to facilitate tissue penetration. In FIG. 31 retention structure 110 is a barbed spike extending substantially perpendicularly from the main body of magnetic device 100. The barbs 115 on spike 110 resist removal of the device from tissue into which spike 110 has been driven. In FIG. 32 retention structure 110 is a pair of wire-like prongs that first extend away from one another where they leave the main body of magnetic device 100. Toward their free ends, prongs 110 curve back toward one another. Again, the free ends of prongs 110 are preferably sharpened to facilitate tissue penetration.

Figure 33:
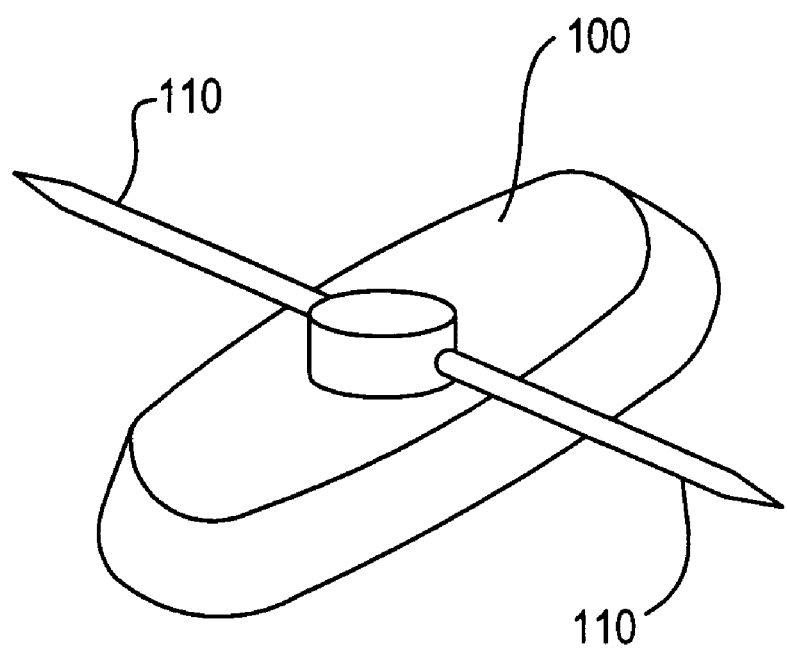

In FIG. 33 the shape of the main body of magnetic device 100 is different from the round or disk shape that has generally been shown in earlier FIGS. FIG. 33 shows the main body of device 100 as elongated, but any of many other shapes (e.g., square, rectangular, etc.) can also be used if desired. The thickness of the main body of a magnetic device 100 can also vary or be uniform.

Figure 34:
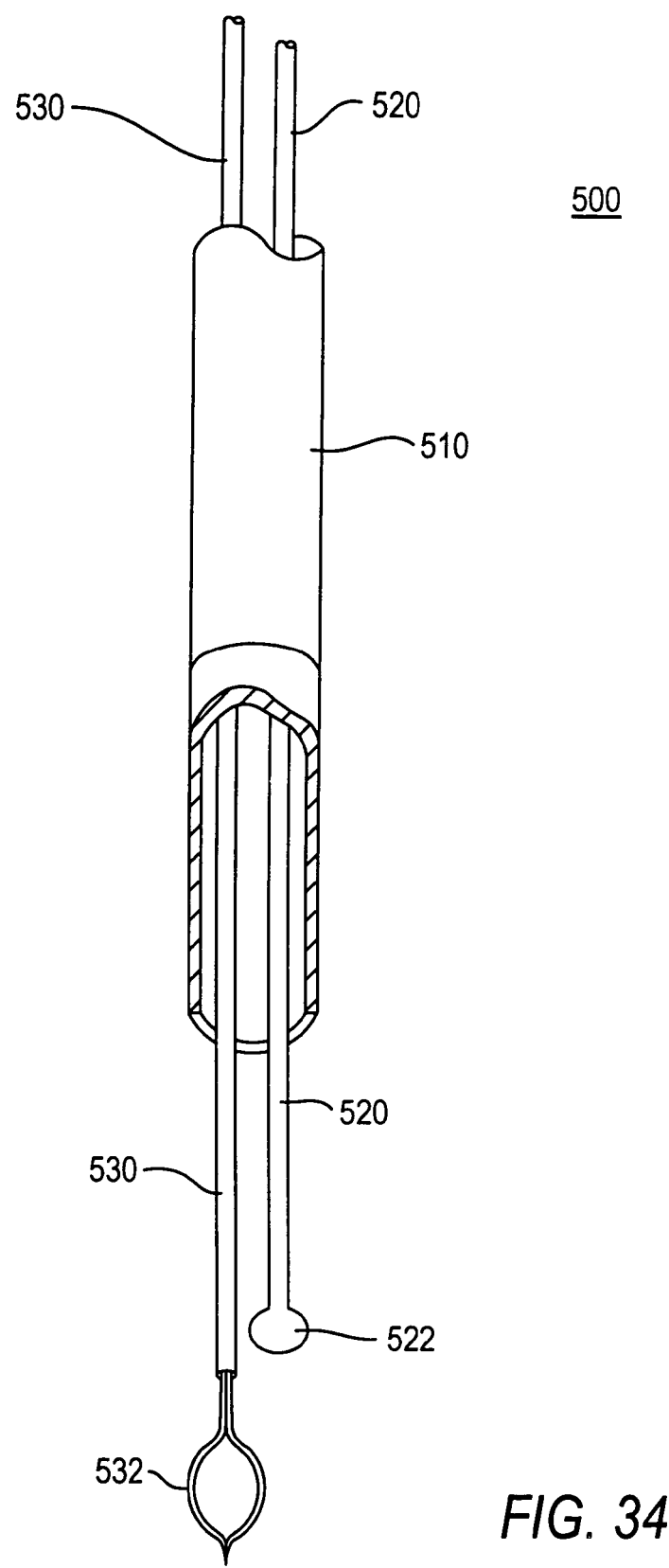
FIG. 34 is a simplified, partial, elevational view (partly in section) of an illustrative embodiment of still more apparatus in accordance with the invention.

FIG. 34 shows a distal portion of illustrative apparatus in accordance with the invention for removing magnetic devices that have been implanted in a patient, if desired. Apparatus 500 is insertable into the patient's esophagus via the patient's mouth when it is desired to use the apparatus. Apparatus 500 includes a delivery catheter 510, within which are longitudinally or axially reciprocable stylet structure 520 and snare structure 530. Snare structure 530 includes a hollow, tubular snare sheath (also referred to by reference number 530) and snare 532 longitudinally or axially reciprocable within snare sheath 530. The distal end of snare 532 is a loop of wire or wire-like material that is resiliently biased to spring open as shown in FIG. 34 when extended from the distal end of snare sheath 530. However, this open loop can be closed down by pulling it into (or partly into) the distal end of snare sheath 530.

Figure 35:
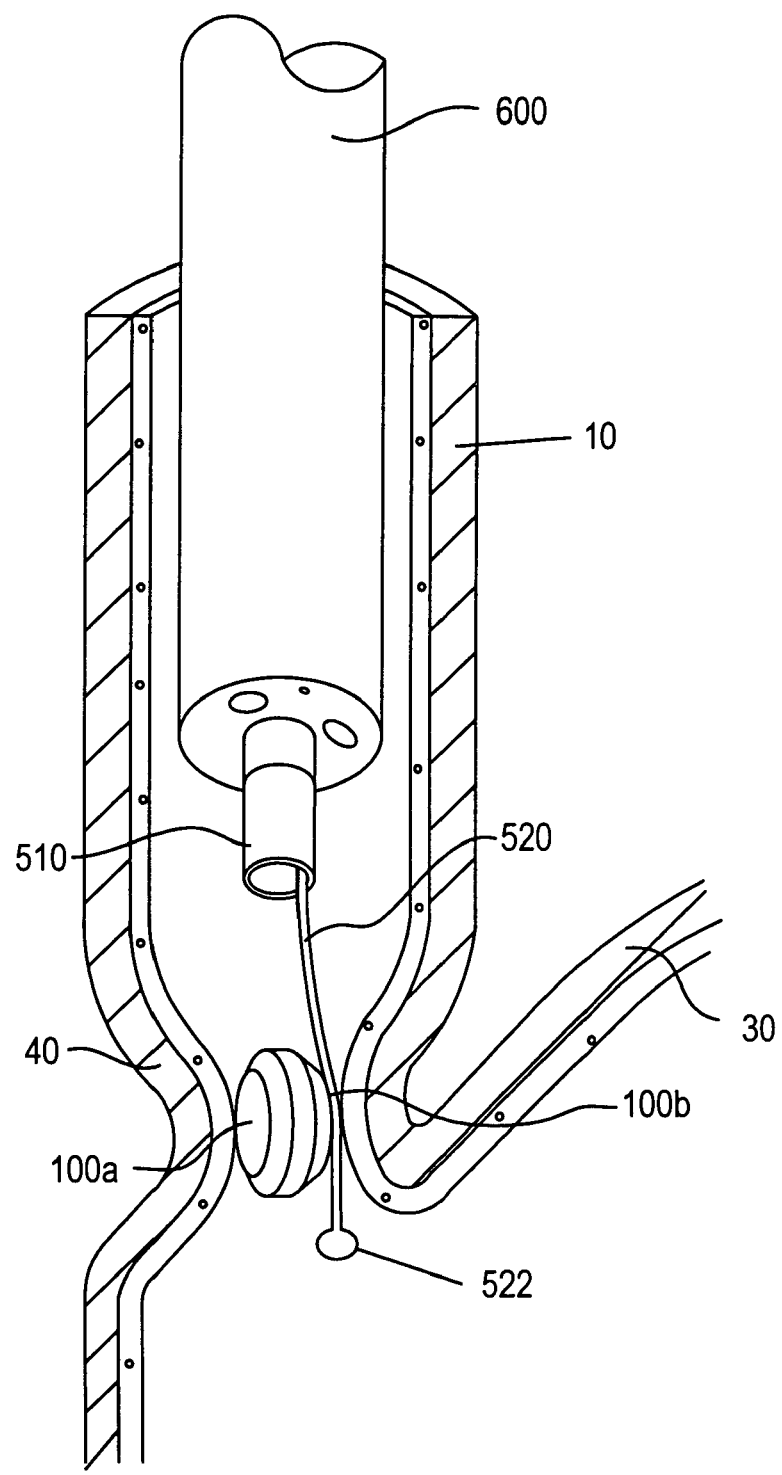
FIGS. 35-39 are views similar to FIG. 29 showing successive stages in use of the FIG. 34 apparatus in accordance with the invention.

FIG. 35 shows that apparatus 500 can be used with or can be part of endoscope apparatus 600 (which can otherwise be conventional). FIG. 35; also shows the start of use of the apparatus to remove one or both of magnetic devices 100a and 100b from a patient's esophagus 10. In FIG. 35 apparatus 500/600 has been inserted into esophagus 10 via the patient's mouth and has been pushed down to just above the lower esophageal sphincter 40. Stylet 520 has then been extended so that its enlarged distal end 522 extends below magnetic devices 100a and 100b.

Figure 36:
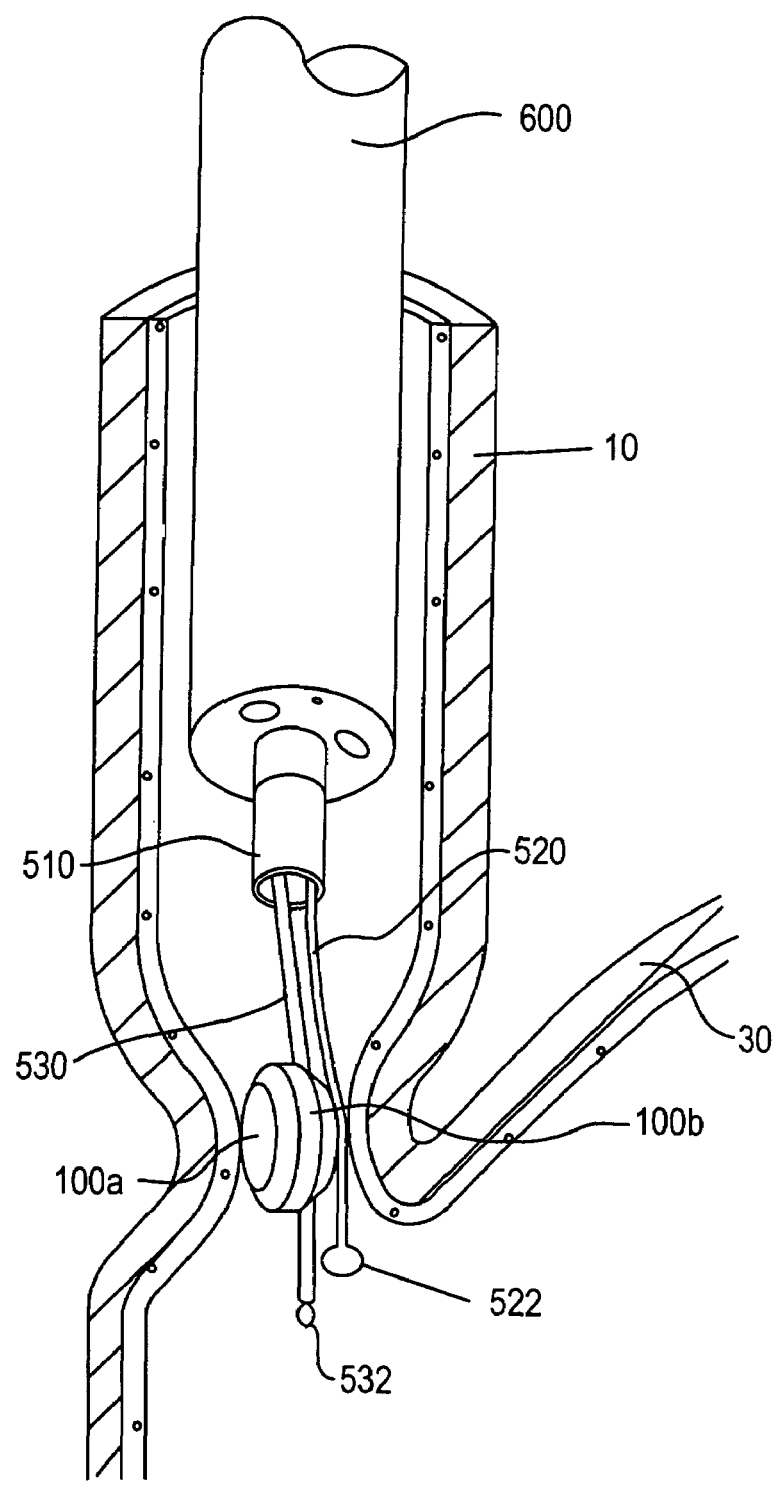

The next step in use of the apparatus is shown in FIG. 36, in which the distal end of snare structure 530 has also been extended below magnetic devices 100, passing those devices on the side opposite the side on which stylet 520 previously passed those devices.

Figure 37:
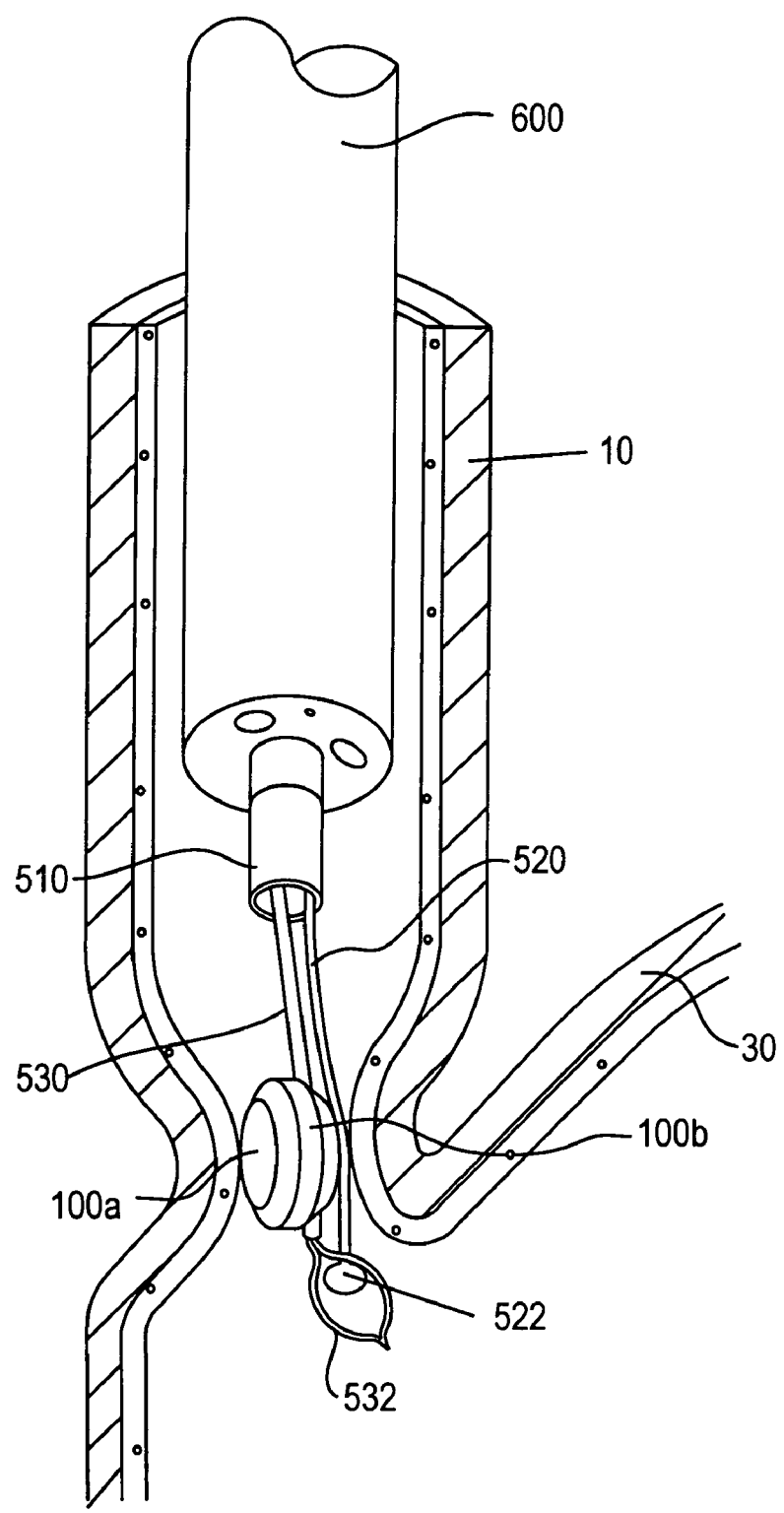

In FIG. 37 snare loop 532 is extended from the distal end of snare sheath 530 so that loop 532 can open. Stylet 520 and snare structure 530 are then manipulated until the enlarged distal end 522 of stylet 520 passes through snare loop 532.

Figure 38:
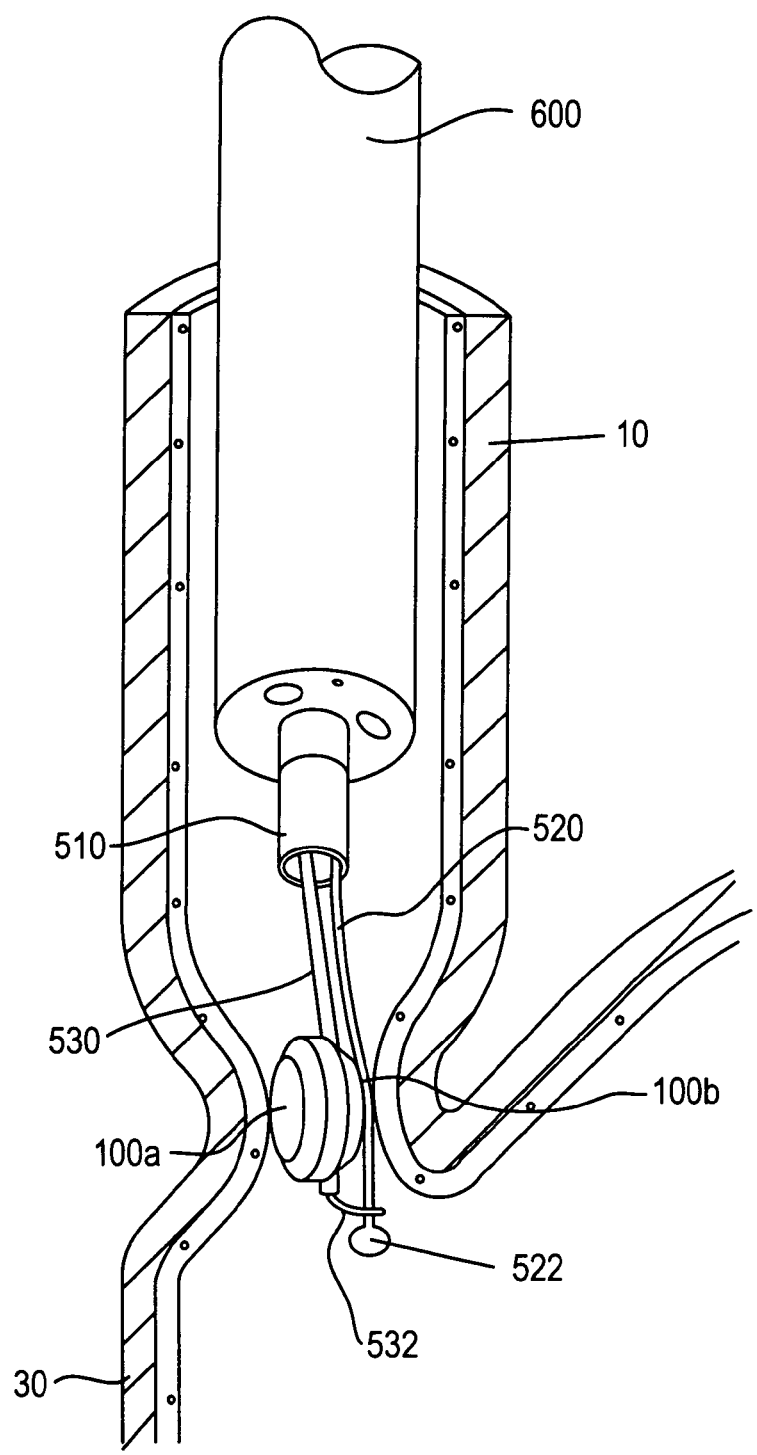

In FIG. 38 snare loop 532 is pulled back into snare sheath 530 to again reduce the size of snare loop 532 and thereby capture the distal end 522 of stylet 520. Stylet 520 and snare structure 530 now form a secure loop that extends around at least one of magnetic devices 100.

Figure 39:
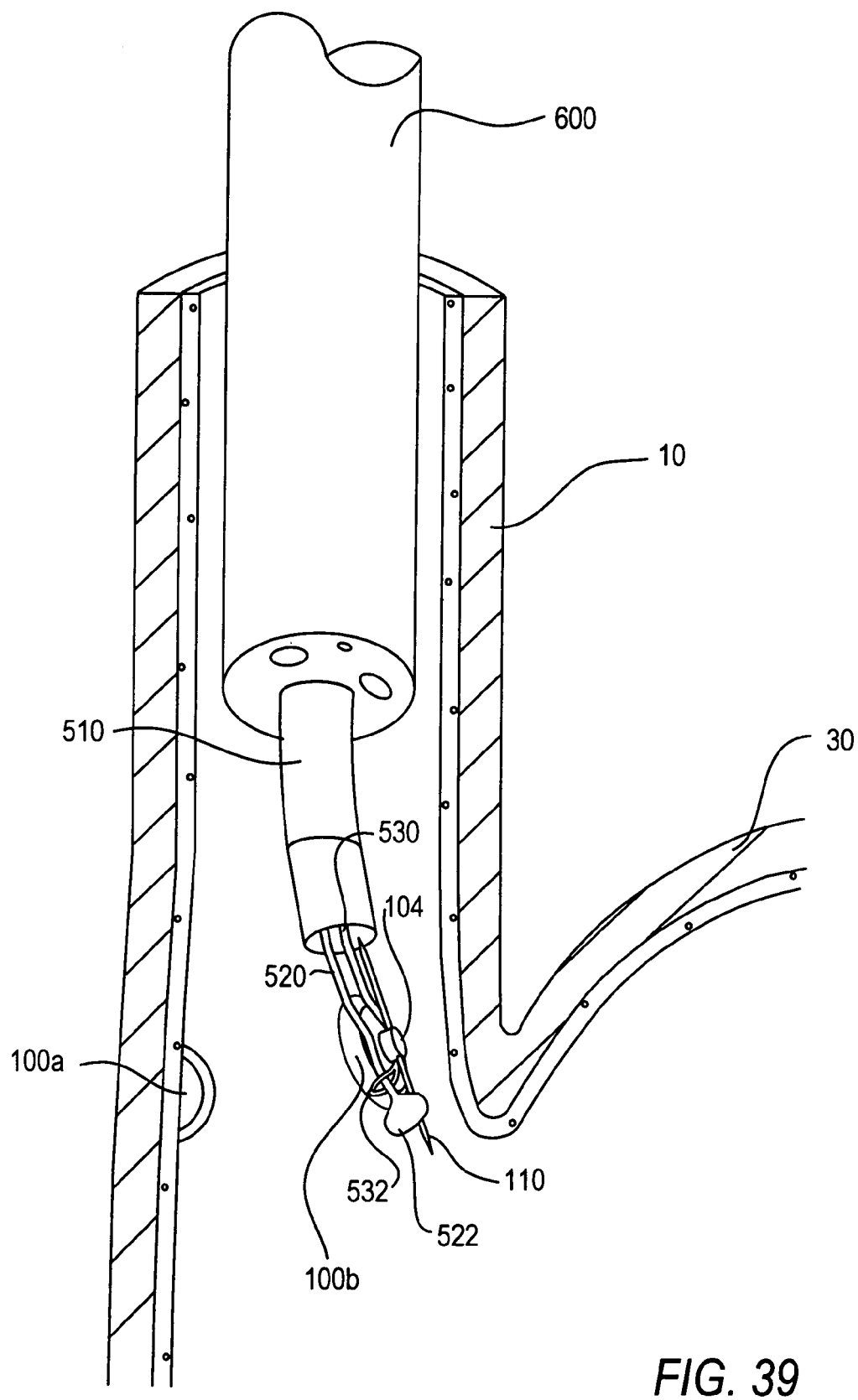

FIG. 39 shows proximal retraction of all of structure 600, 510, etc. This removes at least one of the magnetic devices (e.g. 100b) from the patient's tissue. Removal of apparatus 600, 510, etc. from the patient's mouth takes at least this one magnetic device 100 out of the patient. With at most only one device (e.g., 100a) remaining in the patient, there is no longer any magnetic closing of sphincter 40, so the treatment of that sphincter in accordance with this invention has effectively been reversed. If only one of magnetic devices 100 came out with the first use of apparatus 500/600, that apparatus can be used again to retrieve the other magnetic device if desired.

Figure 40:
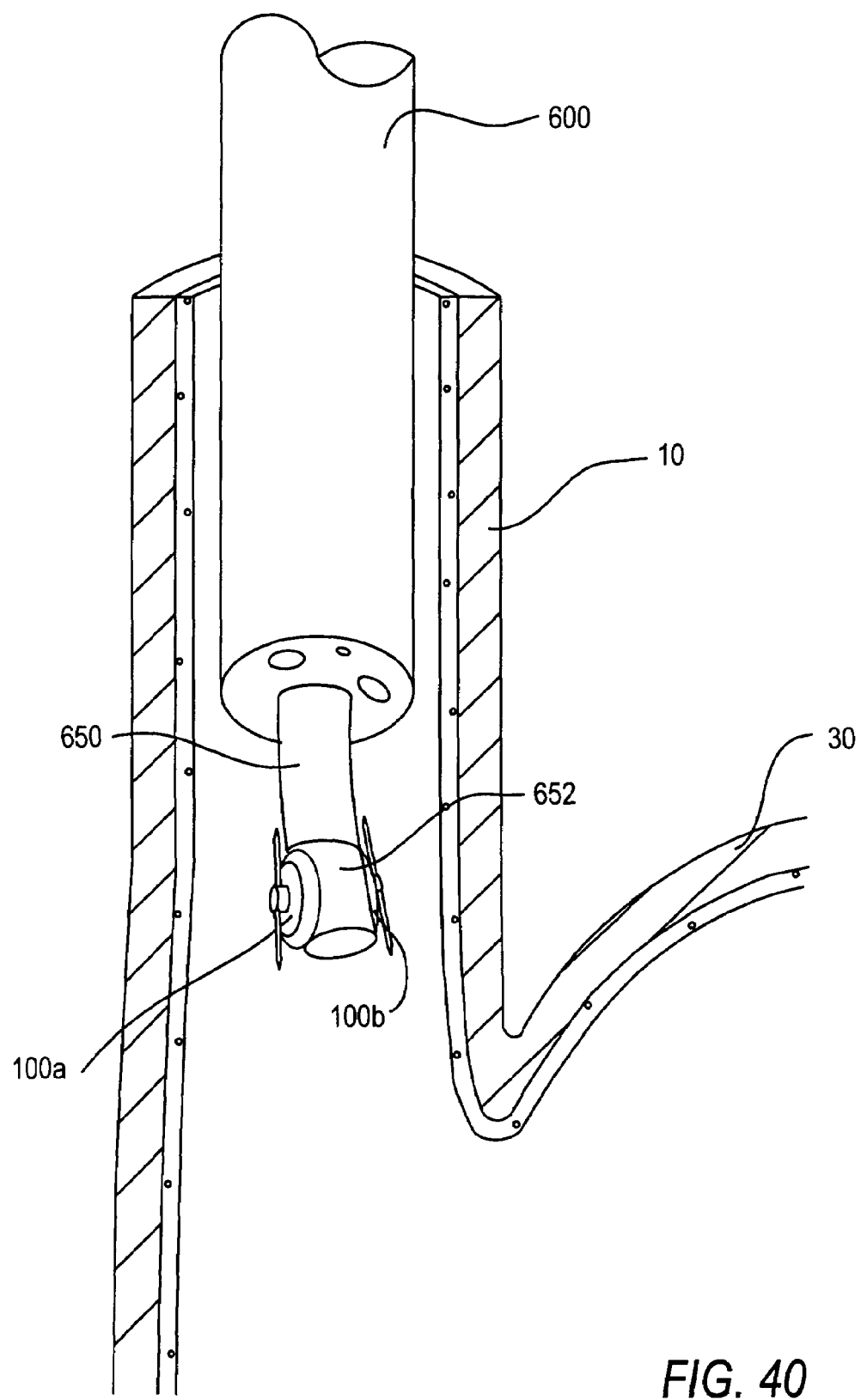
FIG. 40 is another view similar to FIG. 39 showing another illustrative embodiment of apparatus in accordance with the invention.

FIG. 40 shows another illustrative embodiment of apparatus for removing magnetic device(s) 100 from a patient's esophagus after those devices have been implanted in the esophagus. This embodiment may again make use of endoscope 600, which can facilitate delivering magnetic device removal apparatus 650 to the proper location in the patient. For example, after magnetic devices 100 have been visualized via endoscope 600, then removal apparatus 650 may be inserted through a tool lumen in the endoscope and extended beyond the distal end of the endoscope as shown in FIG. 40. Removal apparatus 650 includes a distal portion 652 which is (or which, via electromagnetism, can be selectively made to be) a magnet strong enough to attract magnetic devices 100 and pull them from the wall of the patient's esophagus as shown in FIG. 40. When magnetic devices 100 have thus been pulled out of the tissue, all of apparatus 600, 650, and 652 can be pulled out of the patient via the patient's mouth, thereby completely removing magnetic devices 100 from the patient.

Figure 41:
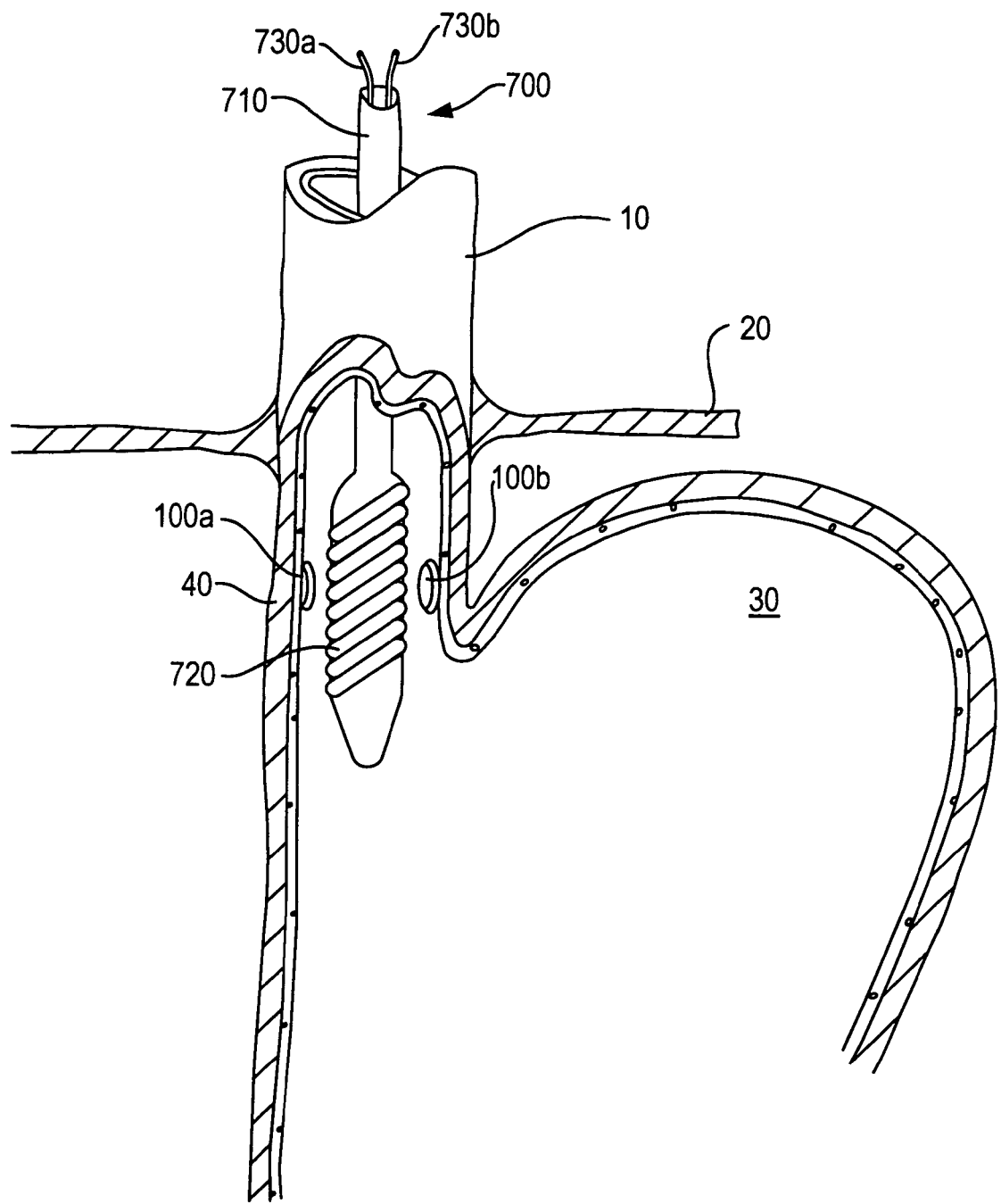
FIG. 41 is another view similar to FIG. 40 showing an illustrative embodiment of still more apparatus in accordance with the invention.

FIG. 41 shows an illustrative embodiment of apparatus 700 in accordance with the invention for changing the magnetism of one or more of magnetic devices 100 after they have been implanted in a patient. The change in magnetism referred to in the preceding sentence can be (1) magnetizing a previously unmagnetized device 100, (2) demagnetizing a previously magnetized device 100, or (3) increasing or decreasing the magnetic strength of a previously magnetized device 100. Apparatus 700 includes a catheter-like central or medial portion 710 for use in delivering a distal end portion 720 of the apparatus to the location of previously implanted magnetic devices 100. The distal end portion 720 of apparatus 700 includes an electromagnetic structure to which electrical current can be supplied via leads 730a and 730b. When the electromagnetic structure of distal portion 720 is electrically energized via leads 730, distal portion 720 produces a magnetic field suitable for producing the desired change in the magnetism of one or more of devices 100. A suitable permanent magnetic structure may be used for distal portion 720 instead of an electromagnet if desired.

As an alternative to introducing apparatus like 700 into the patient, similar results may be obtained by placing a suitable magnetic field source near the patient (but outside the patient's body) to change the magnetism of one or more of magnetic devices 100.

Various objectives may be achieved by changing the magnetism of devices 100 after they have been implanted. For example, if the patient's GERD has not improved sufficiently, the strength of magnetic devices 100 may be increased to see if that will help. Alternatively, if the closure of sphincter 40 is now too strong, the strength of magnetic devices 100 may be reduced. As still another example, demagnetizing magnetic devices 100 may be used as an alternative to physically removing them from the patient to reverse or terminate treatment in accordance with the invention.

Figure 42:
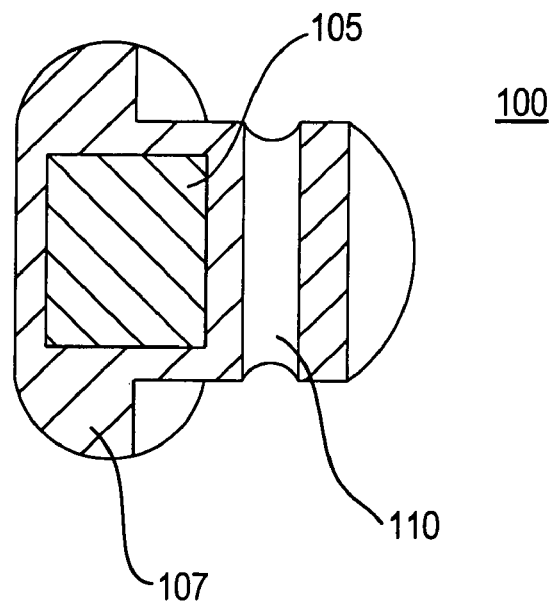
FIG. 42 is a simplified sectional view of another illustrative embodiment of a magnetic device in accordance with the invention.

FIGS. 42-49 show another illustrative construction of magnetic devices 100 in accordance with the invention, and illustrative apparatus for implanting such devices, also in accordance with the invention. As shown in FIG. 42, this illustrative embodiment of a magnetic device 100 includes a disk-shaped permanent magnet 105 embedded in an external structure shell 107. As in other embodiments, magnet 105 can be made of any material capable of producing a magnetic field. Again (as for other embodiments), the preferred materials are rare earth magnets because of their superior field strength. Especially preferred materials include Alnico (aluminum/nickel/cobalt), SmCo (samarium/cobalt), and NdFeB (neodymium/iron/boron). Also as for other embodiments, the magnetic force exerted will depend on various factors, including material, length, and width of the magnet. The required magnet strength depends on the forces needed to improve the closing function of a lower esophageal sphincter, while allowing fluids and solids to enter the stomach. Also as for other embodiments, body 105 in the FIGS. being discussed can be passively magnetic (rather than actively magnetic) in one or more of devices 100, as long as any such passively magnetic device(s) is (are) used so as to cooperate with one or more other actively magnetic devices 100.

Suitable material for external shell 107 in the FIGS. being discussed (as for other embodiments) are preferably non-porous, biocompatible, biostable, corrosion resistant, and of sufficient structural integrity to absorb in vivo loads. Such materials include, but are not limited to, known-implantable metals such as stainless steel or titanium, high-density polymers such as parylene or ultra-high molecular weight polyethylene, or materials made from non-metallic minerals such as ceramic or glass.

An aperture 110 extends through shell 107 across a diameter of device 100 to aid in securing the assembly to the esophageal wall as will be described in subsequent paragraphs.

Figure 43:
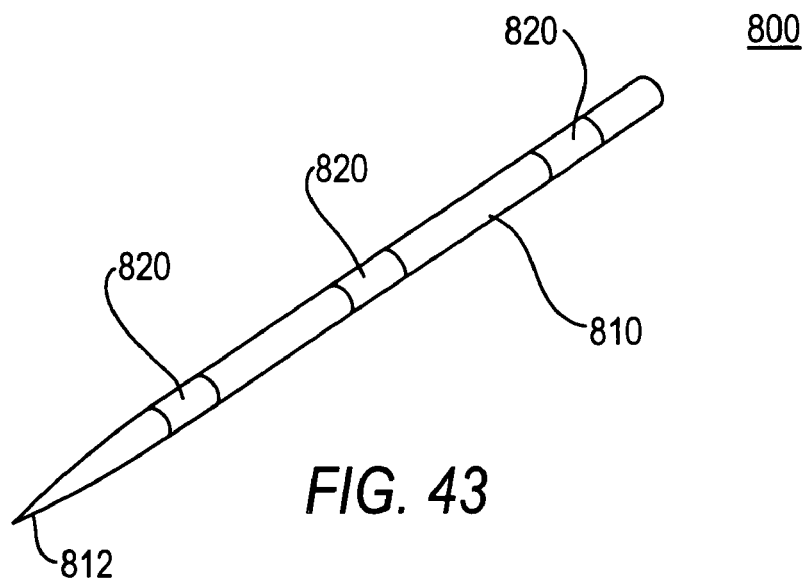
FIG. 43 is a simplified perspective view of an illustrative retention structure that can be used, for example, with magnetic devices of the type shown in FIG. 42 in accordance with the invention.

FIG. 43 shows an illustrative, wire-like stylet 800 for use in implanting magnetic devices 100 of the type shown in FIG. 42 in a patient. Although stylet 800 could be constructed differently, in the particular embodiment shown in FIG. 43 stylet 800 includes a non-ferrous longitudinal member 810 with ferrous segments 820 spaced along the length of the longitudinal member. Longitudinal member 810 is a structural component with a sharpened distal end 812 designed to penetrate the esophageal wall and traverse through the lumen 110 in each magnetic device 100 of the type shown in FIG. 42 in order to stitch the assembly in place in the patient. Ferrous segments 820 are designed to magnetically attract retention stylet 800 to each individual magnetic device 100. The magnetic force established between the magnetic device(s) 100 and ferrous segment(s) 820 helps to hold stylet 800 in place. Stylet 800 could additionally or alternatively be provided with a mechanical mechanism to lock the magnetic device(s) 100 in place.

Figure 44:
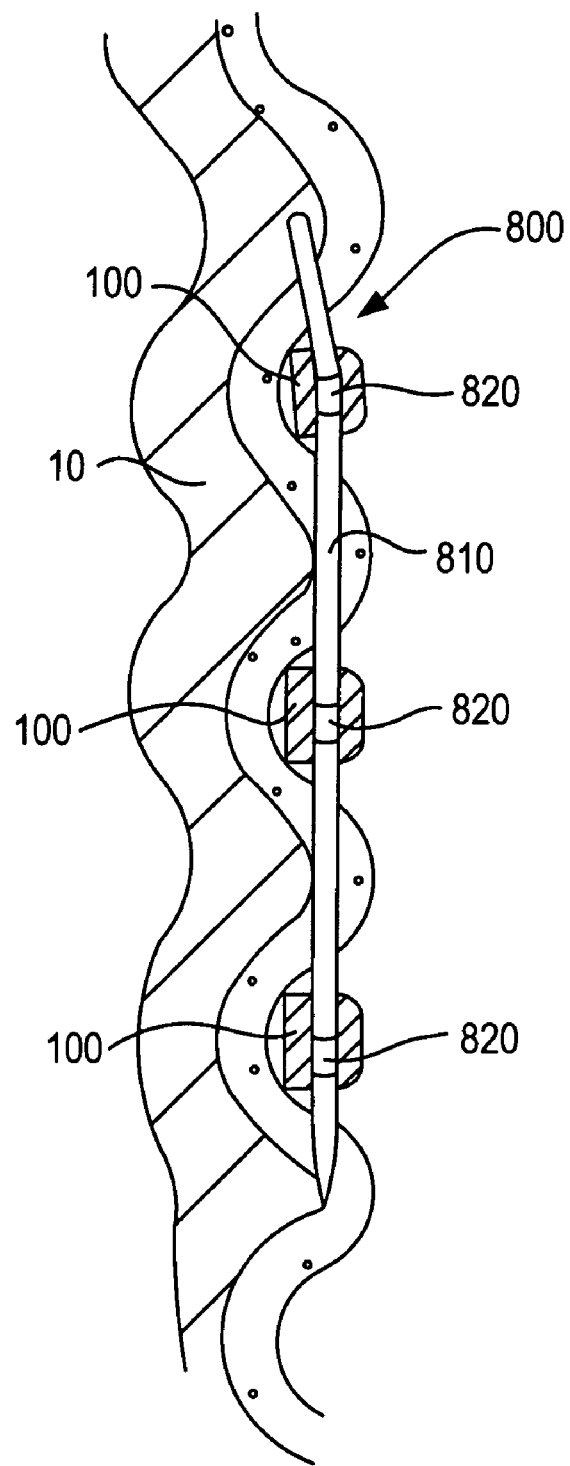
FIG. 44 is a simplified view, partly in section, illustrating use of elements like those shown in FIGS. 42 and 43 in accordance with the invention.

FIG. 44 shows several magnetic devices 100 of the type shown in FIG. 42 secured to one side of a patient's esophagus 10 by a stylet 800. Note that a ferrous segment 820 is positioned adjacent each magnetic device 100 in FIG. 44.

Figure 45:
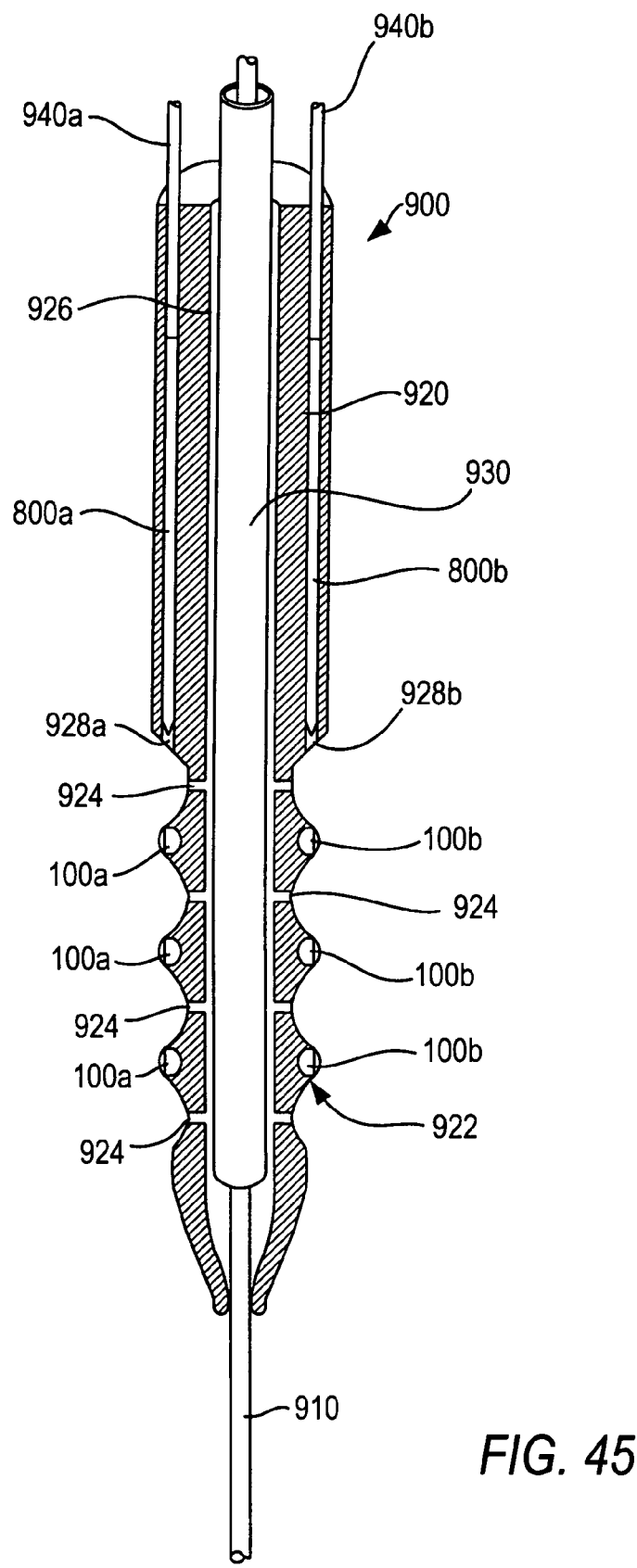
FIG. 45 is a simplified view, partly in section, showing illustrative apparatus for delivering and implanting elements like those shown in FIGS. 42 and 43 in accordance with the invention.

FIG. 45 shows the distal portion of an illustrative embodiment of a delivery system 900 for implanting magnetic devices 100 like those shown in FIGS. 42 and 44 (using stylets 800 as shown in FIGS. 43 and 44) in accordance with the invention. Apparatus 900 may be designed to removably accept an endoscope 910, shown in FIG. 45 traversing the length of the remainder of apparatus 900. Multiple magnetic devices 100 (100a on the left and 100b on the right) are positioned on each side of a longitudinal delivery structure 920 at respective peaks in serpentine exterior surfaces 922 of a relatively distal portion of structure 920. Magnetic devices 100 are held in place at these locations in structure 920 by their magnetic attraction to ferrous or magnetic tube 930 that is removably disposed inside structure 920 coaxially around endoscope 910. A substantially radial orifice 924 extends through each valley in each serpentine surface 922 and communicates with a vacuum lumen 926 that extends along the length of the apparatus inside structure 920. Magnet retention stylets 800 (800a on the left and 800b on the right) are contained in stylet advancement lumens 928 that are proximal of but axially aligned with each set of magnetic devices 100. Stylet advancement rods 940 (940a on the left and 940b on the right) are positioned proximally of retention stylets 800 for use in driving stylets 800 in the distal direction at the appropriate time.

Figure 46:
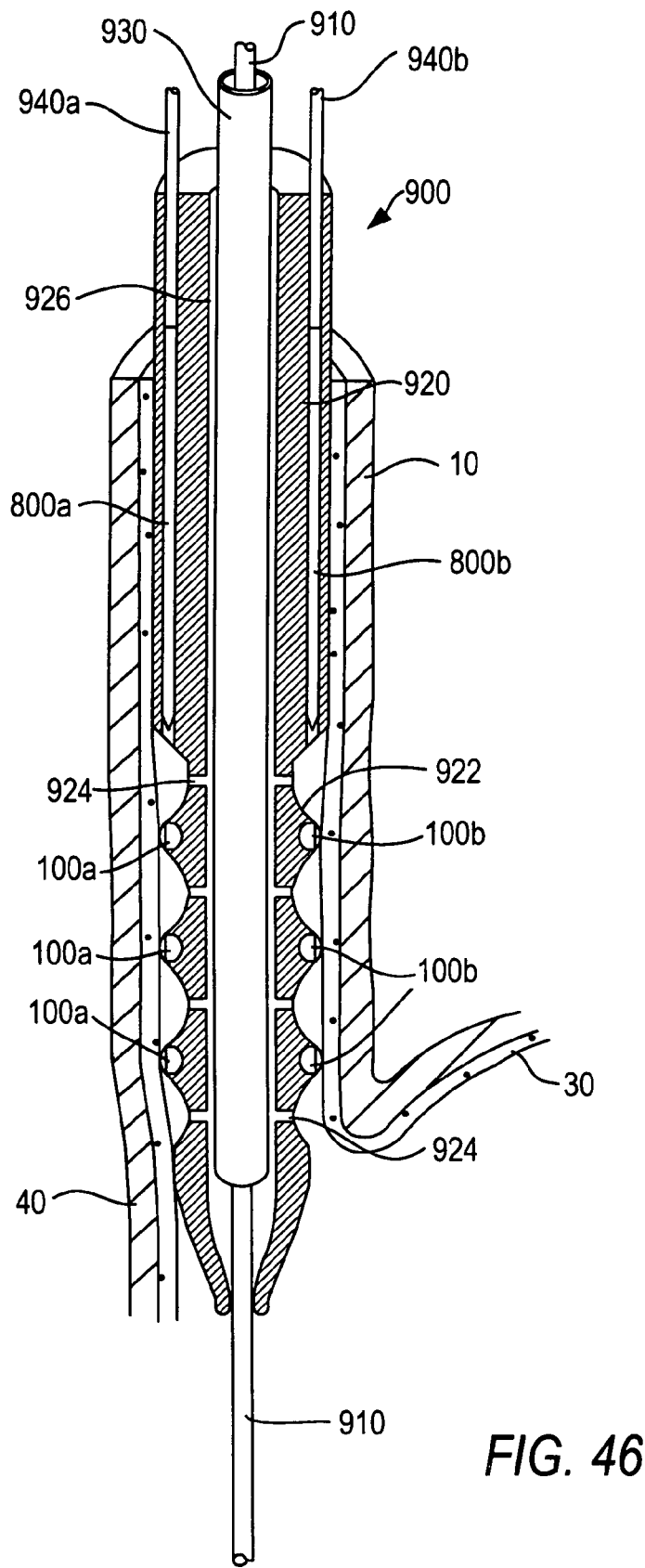
FIG. 46 is a simplified view, partly in section, showing an early stage in use of the FIG. 45 apparatus in accordance with the invention.

FIG. 46 shows the distal portion of delivery system 900 positioned in a patient's esophagus 10 with magnetic devices 100 in the vicinity of lower esophageal sphincter 40. This condition has been achieved by inserting the apparatus via the patient's mouth. As in FIG. 4 and other embodiments, control portions of apparatus 900 remain outside the patient for operation by the user (a physician or the like) of the apparatus. The outside diameter of delivery apparatus 900 is designed to be large enough relative to the inside diameter of the esophagus to create a relatively air-tight seal between the apparatus and the surrounding tissue.

Figure 47:
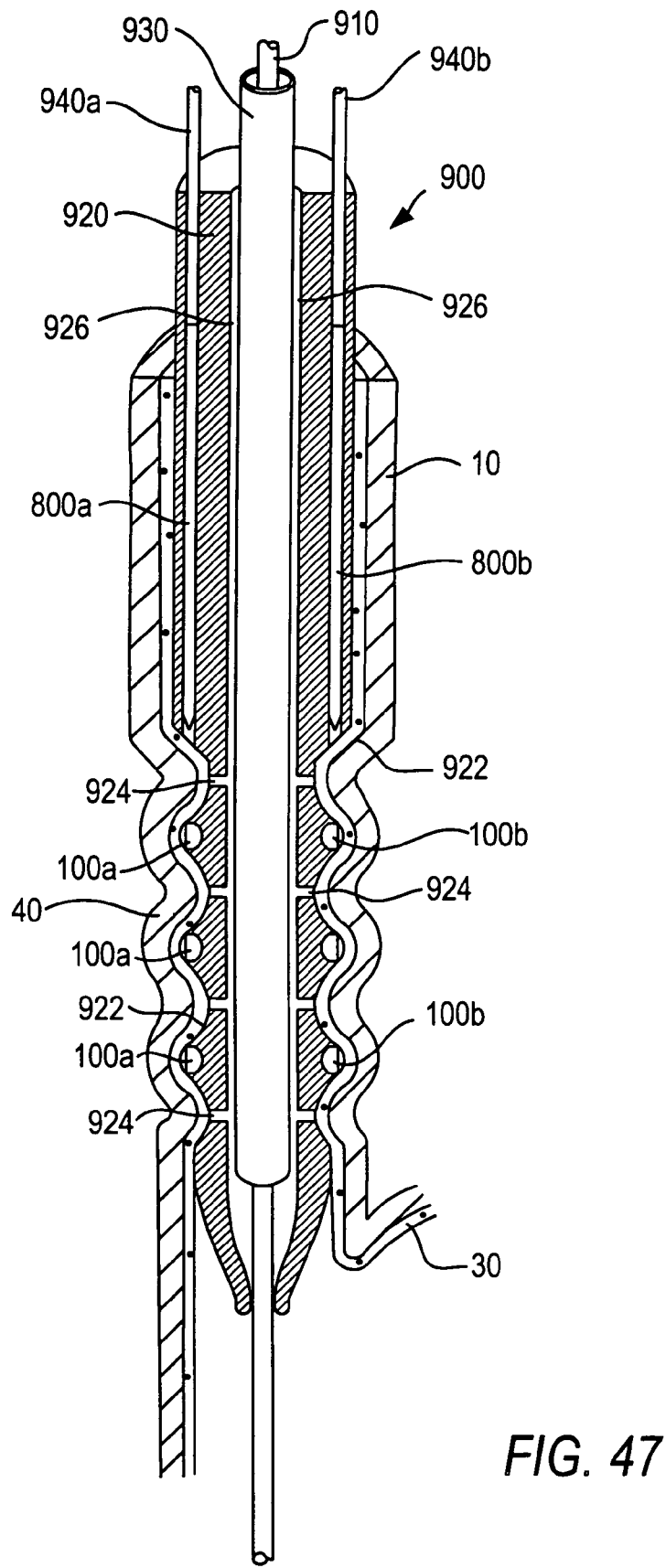
FIG. 47 is similar to FIG. 46, but shows a later stage in use of the apparatus.
Figure 48:
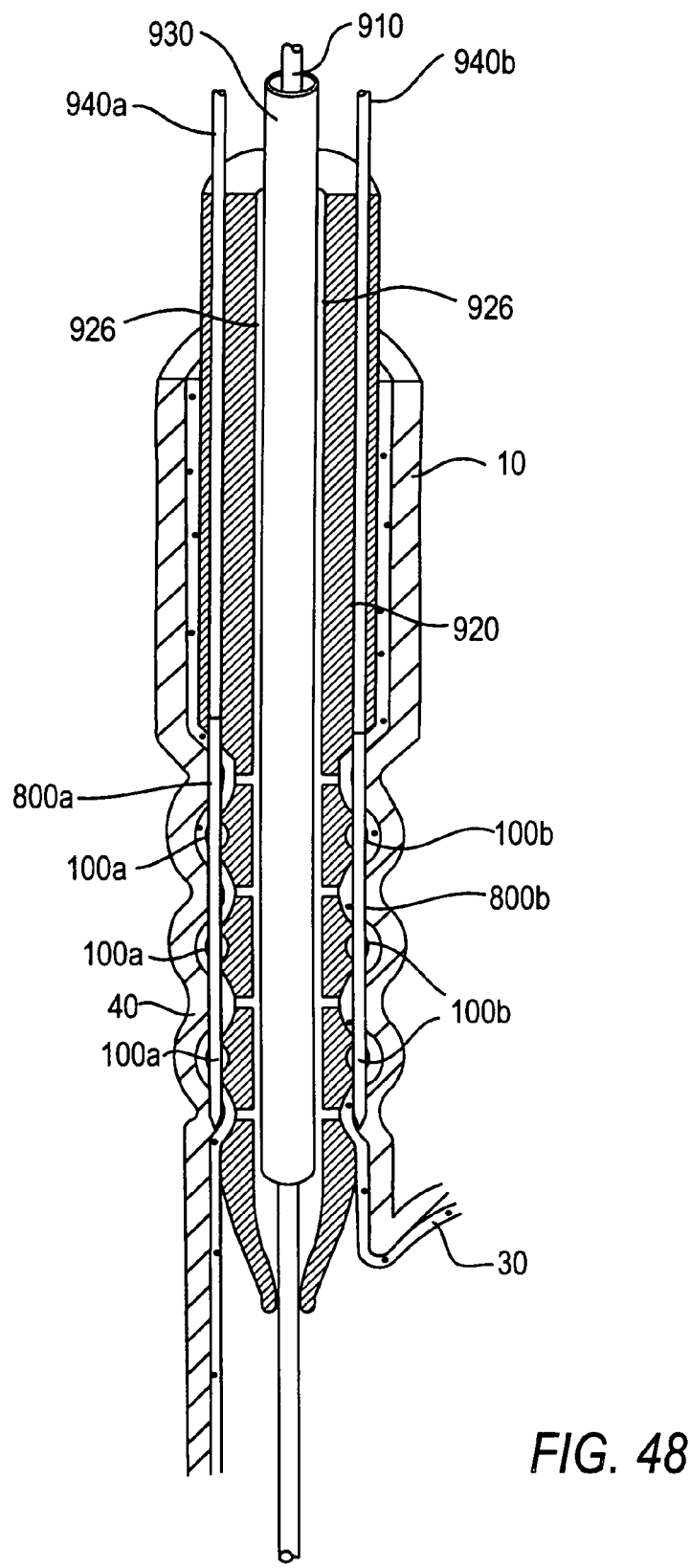
FIG. 48 is similar to FIG. 47, but shows a still later stage in use of the apparatus.

FIG. 47 shows the next step in use of the apparatus being discussed. In this step reduced gas pressure (i.e., sub-atmospheric or "vacuum" pressure) is applied to vacuum lumen 926 from a source of reduced gas pressure outside the patient. This reduced gas pressure is communicated to the wall of the patient's esophagus 10 via radial orifices 924, which causes the wall of the esophagus to closely conform (i.e., follow) the serpentine surfaces 922, of the lower portion of delivery structure 920. This places tissue of the esophagus wall directly above and below each of magnetic devices 100 and aligned with a downward projection of each of magnet retention stylets 800.

The next step (shown in FIG. 48) is to advance stylet advancement rods 940a and 940b in the distal direction. This drives magnet retention stylets 800a and 800b through the esophageal tissue and through the apertures 110 (FIG. 42) in magnetic devices 100a and 100b. Stylets 800 thus now secure magnetic devices 100 to the wall of the esophagus on opposite sides of the esophageal lumen.

Figure 49:
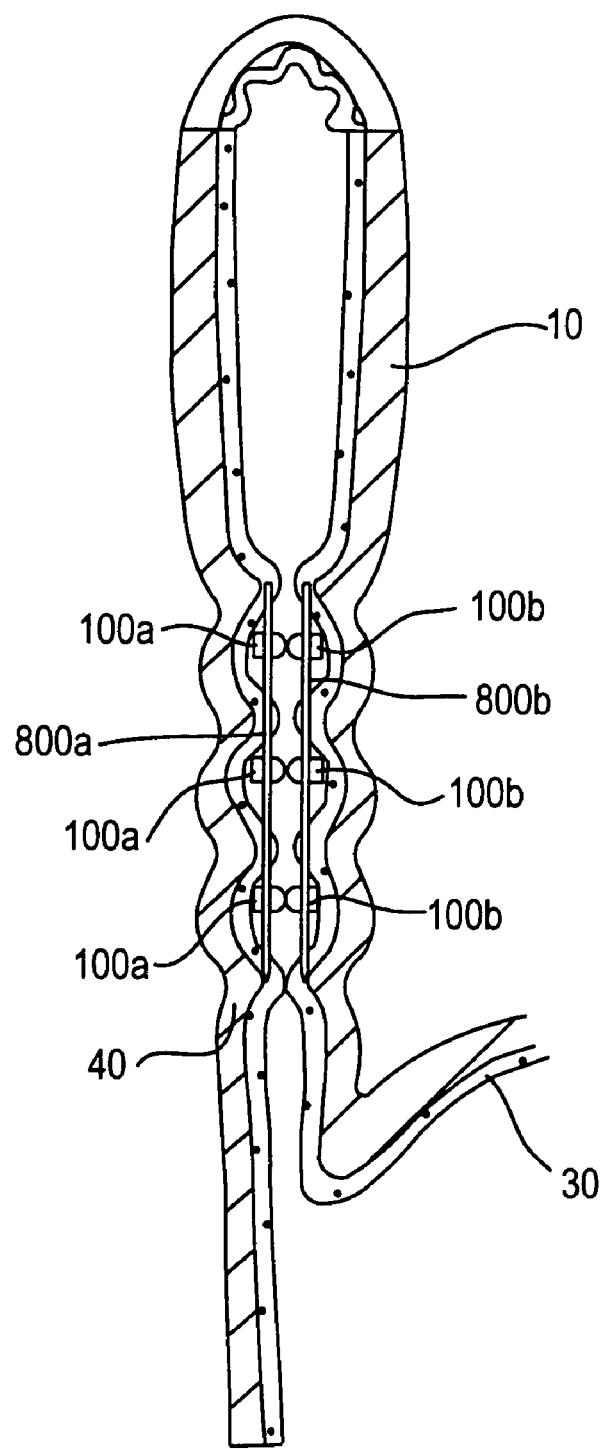
FIG. 49 is again similar to FIG. 48, but shows the end result produced by use of the apparatus (which has now been withdrawn from the patient).
Figure 50:
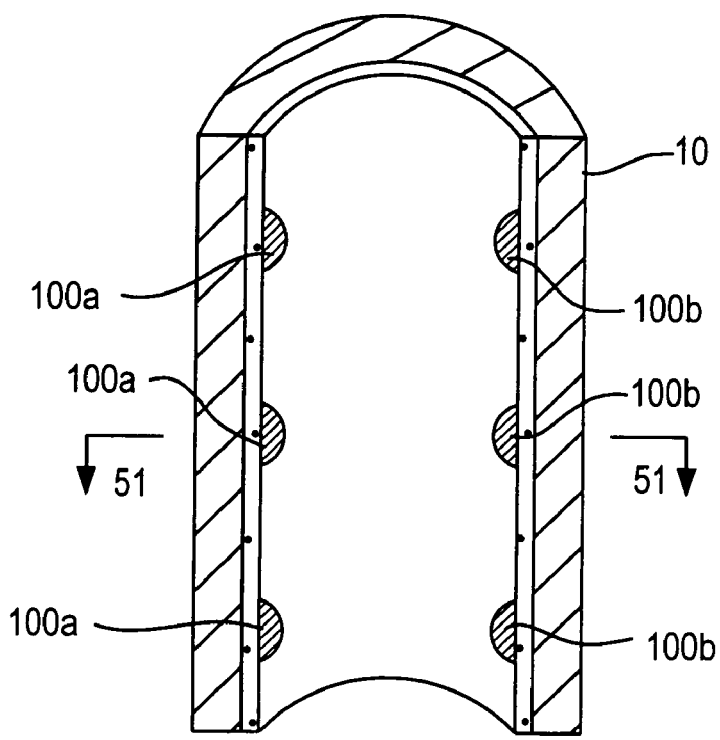
FIG. 50 is a simplified sectional view (taken generally along the line 50-50 in FIG. 51) showing an illustrative implantation of magnetic devices in a patient in accordance with the invention.

The next step (not separately depicted) is to release the vacuum applied to lumen 926 and orifices 924, and to proximally withdraw (or at least shift) ferrous or magnetic tube 930. This movement of tube 930 removes it from the vicinity of magnetic devices 100, thereby releasing devices 100 from deployment apparatus 900. Positive (above-atmospheric) gas or liquid pressure may then be applied to passageways 926 and 922 to help separate elements 100 and 800 from delivery apparatus 900. Stylet advancement rods 940 may also be proximally retracted to ensure that they do not pin any tissue to deployment apparatus 900. Deployment apparatus 900 may then be pulled proximally out of the patient's mouth, leaving behind elements 100 and 800 in the condition shown in FIG. 49. In particular, FIG. 49 shows that magnetic attraction between magnetic elements 100*a* and 100*b* on respective opposite sides of the esophageal lumen helps to close that lumen in the vicinity of lower esophageal sphincter 40. Of course, the esophageal lumen opens, at least in part, when liquids or solids are swallowed by the patient or when pressure in the patient's stomach 30 becomes significantly higher than normal.

Although FIGS. 44-49 show implanting two lines of three magnetic devices each, it will be understood that this approach can be adapted to implanting any number of magnetic devices in each line (e.g., one device, two devices, three devices (as shown), or more than three devices per line), and to implanting any number of lines of such devices (e.g., one line, two lines (as shown), three lines, four lines, or more than four lines).

Figure 51:
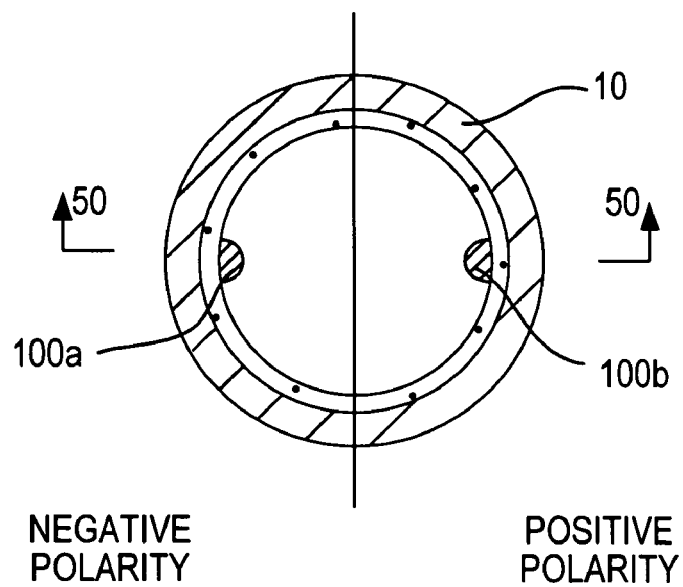
FIG. 51 is another simplified sectional view taken generally along the line 51-51 in FIG. 50.
Figure 52:
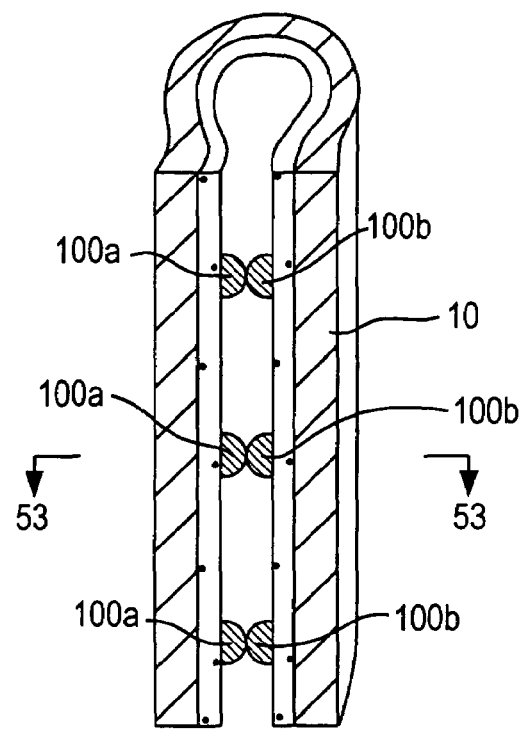
FIG. 52 is similar to FIG. 50, but shows a different operating condition of what is shown in FIG. 50.
Figure 53:
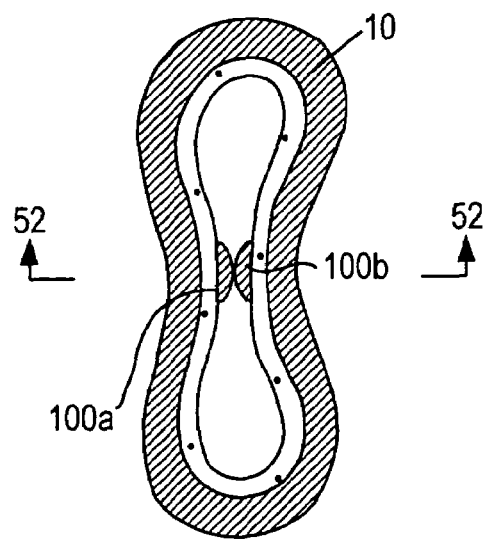
FIG. 53 is another simplified sectional view taken generally along the line 53-53 in FIG. 52.
Figure 54:
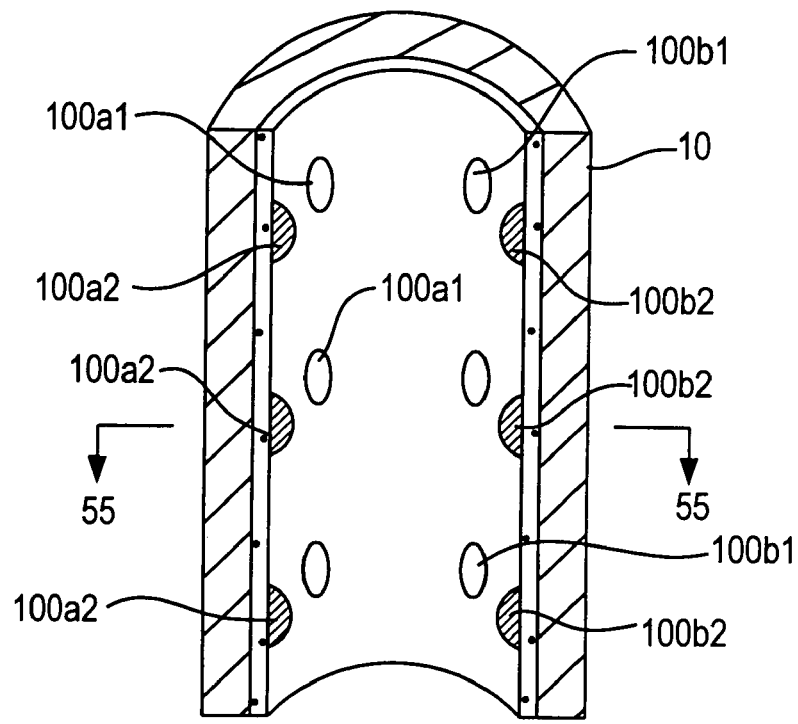
FIG. 54 is a view similar to FIG. 50, but for another illustrative implantation of magnetic devices in a patient in accordance with the invention.
Figure 55:
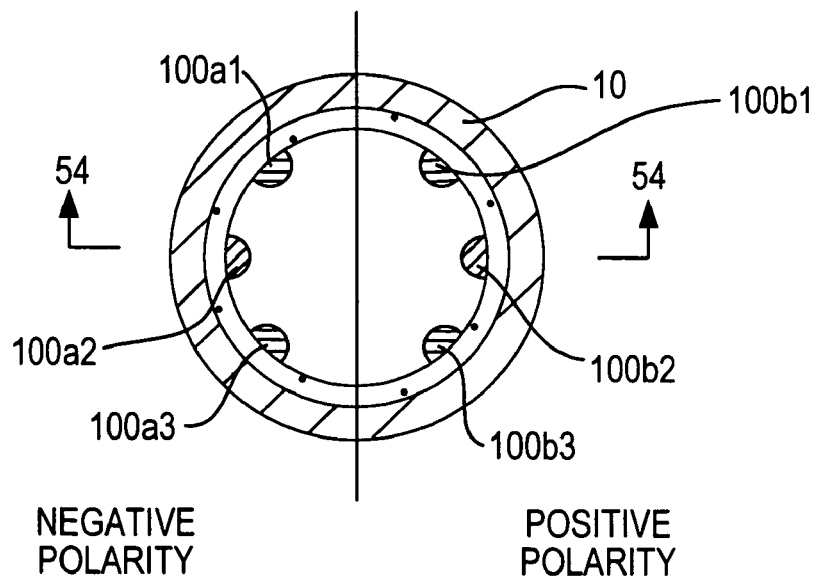
FIG. 55 is another simplified sectional view taken generally along the line 55-55 in FIG. 54.

FIGS. 50-53 show a generalized embodiment having two lines of magnetic devices 100*a* and 100*b* on respective opposite sides of esophagus 10. (In FIGS. 50 and 51, esophagus 10 is shown open; in related FIGS. 52 and 53, esophagus 10 is shown closed.) In other words, these two lines of magnetic devices 100*a* and 100*b* are positioned diametrically opposite one another (approximately 180° apart in the direction circumferentially or annularly around esophagus 10). FIG. 51 shows that magnetic devices 100*a* (on one side of esophagus 10) have magnetic polarity opposite the magnetic polarity of magnetic devices 100*b* (on the other side of esophagus 10). (The placement of "negative polarity" on the left and "positive polarity" on the right is entirely arbitrary and can be reversed if desired.) Because of their opposite magnetic polarities, magnetic devices 100*a* and 100*b* are mutually attracted to one another, thereby helping to hold the esophagus normally closed as shown in FIGS. 52 and 53.

Figure 56:
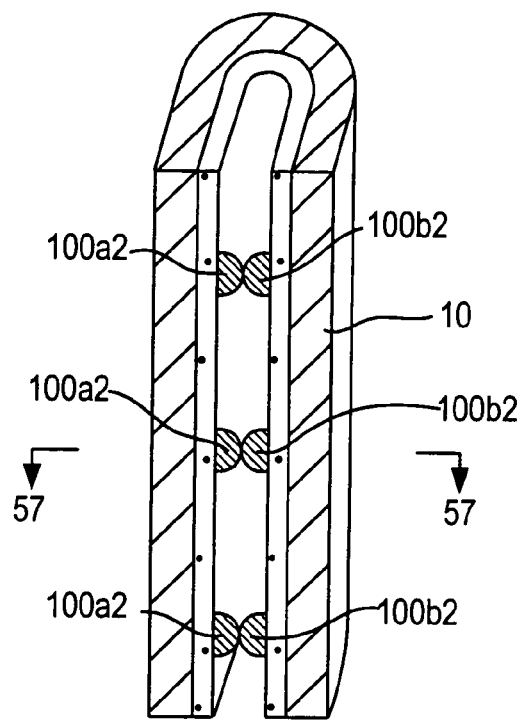
FIG. 56 is similar to FIG. 52, but for the embodiment shown in FIGS. 54 and 55.
Figure 57:
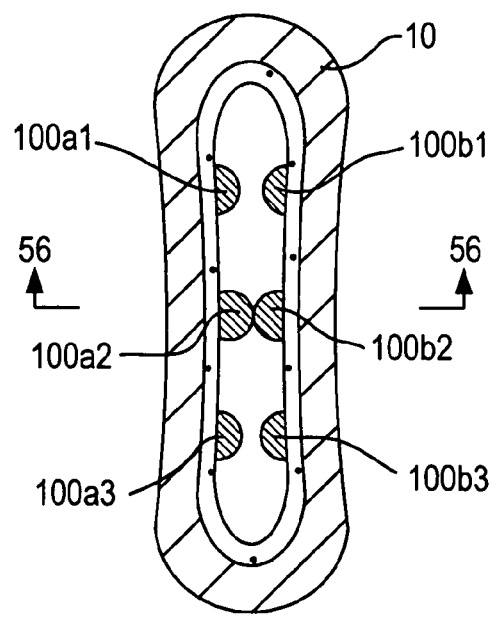
FIG. 57 is another simplified sectional view taken generally along the line 57-57 in FIG. 56.

FIGS. 54-57 show another generalized embodiment having two sets of three substantially parallel lines of magnetic devices 100*a*1-3 and 100*b*1-3 on respective opposite sides of esophagus 10. (In FIGS. 54 and 55, esophagus 10 is shown open; in related FIGS. 56 and 57, esophagus 10 is shown closed.) The three lines of magnetic devices 100*a*1-3 on one side of the esophagus have one magnetic polarity (identified as "negative polarity" in FIG. 55), while the three lines of devices 100*b*1-3 on the opposite side of the esophagus have the opposite magnetic polarity (identified as "positive polarity" in FIG. 55). (Again the choice of which side is positive and which is negative is arbitrary and can be reversed if desired.) Because of their opposite magnetic polarities, magnetic devices 100*a*1-3 and 100*b*1-3 are mutually attracted to one another, thereby helping to hold the esophagus normally closed as shown in FIGS. 56 and 57. In particular, magnetic devices 100*a*1 and 100*b*1 are mutually attracted to one another, magnetic devices 100*a*2 and 100*b*2 are mutually attracted to one another, and magnetic devices 100*a*3 and 100*b*3 are mutually attracted to one another. Because some of devices 100*a* are now spaced from one another circumferentially, and some of devices 100*b* are similarly spaced from one another circumferentially, the esophagus-closing forces exerted by the magnetic attraction of these devices is similarly distributed circumferentially. In other words, a circumferentially wider portion of one side of the esophagus is now attracted to a circumferentially wider portion of the opposite side of the esophagus (as compared, for example, to the embodiment shown in FIGS. 50-53). This greater circumferential distribution of the esophagus-closing force produced by magnetic devices 100 may be preferable in some instances.

Figure 58:
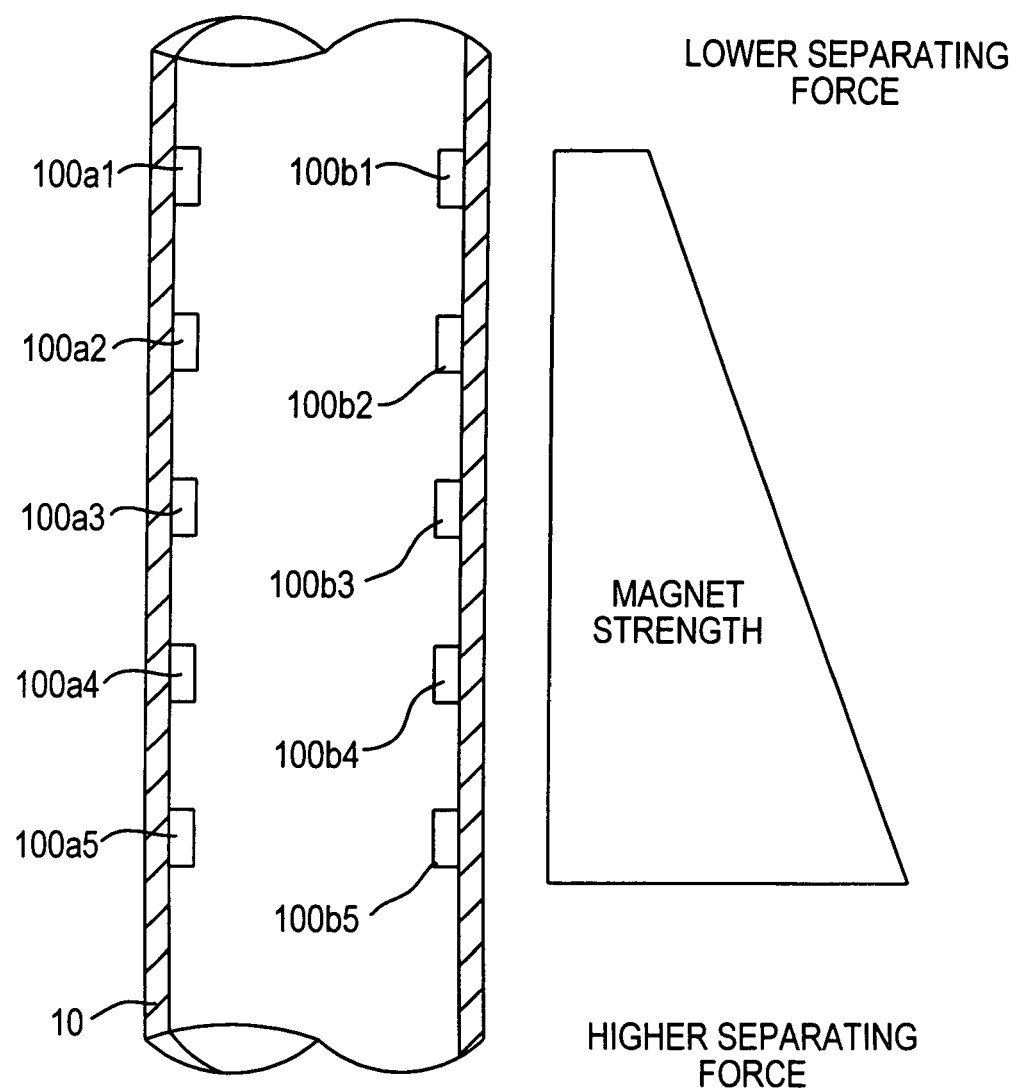
FIG. 58 is a simplified, partial, elevational view (partly schematic in nature) showing still another illustrative implantation of magnetic devices in a patient in accordance with the invention.

FIG. 58 illustrates an embodiment in which the strength of magnetic devices 100 is different at different locations in an implanted array of such devices. In the particular embodiment shown in FIG. 58 the strength of magnetic devices 100 (implanted in two parallel lines axially along respective opposite sides of esophagus 10) increases in the distal direction along the esophagus. (FIG. 58 shows the esophagus open and as though transparent to render visible the magnetic devices 100 implanted inside the esophagus.) Thus the magnetic attraction between devices 100*a*1 and 100*b*1 is weakest, the attraction between devices 100*a*2 and 100*b*2 is somewhat stronger, and so on until the strongest magnetic attraction is provided between devices 100*a*5 and 100*b*5. As a result, of this progression of magnetic force strength, FIG. 58 indicates diagrammatically that the force required to separate the various pairs of magnets and open the associated portions of the esophagus increases from top to bottom of the array. Thus "lower separating force" is required to open the portion of the esophagus near the top of the array of magnetic devices 100, and "higher separating force" is required to open the portion of the esophagus near the bottom of the array. Magnets with less attractive strength at the upper end of the array may increase the ability of the supported esophagus to open during swallowing of fluids or solids, while stronger magnets at the lower end of the array may better resist stomach acid from exiting the stomach via the lower esophageal sphincter.

Figure 59:
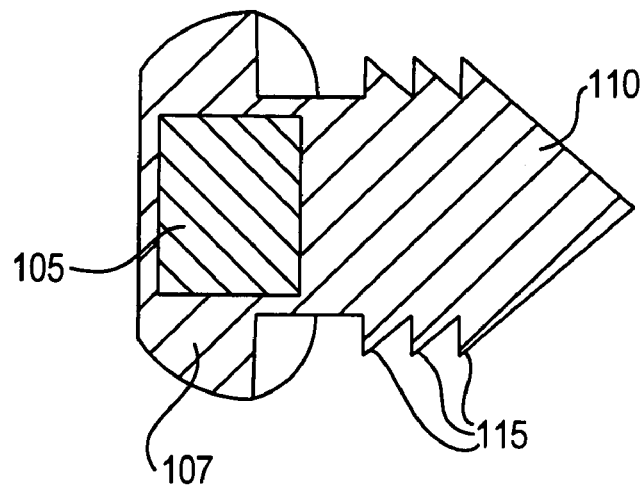
FIG. 59 is a simplified sectional view of yet another illustrative embodiment of a magnetic device in accordance with the invention.

FIG. 59 shows another example of a possible construction of a representative magnetic device 100. This embodiment can be generally similar to the embodiment shown in FIG. 31. FIG. 59 shows a magnetic device 100 having a magnetic body 105 (which can be either actively or passively magnetic) embedded in a shell 107. Retention structure 110 extends from one side of shell 107. Retention structure 110 has a sharply pointed free end or tip remote from magnetic body 105. This sharply pointed tip helps retention structure 110 penetrate tissue during implantation. Back from the pointed tip along retention structure 110 the retention structure includes a plurality of radially (or transversely) outwardly extending barbs 115 that are shaped and oriented to enter tissue relatively easily, but to resist subsequent withdrawal from the tissue. Thus each barb 115 has one side that is substantially parallel to the adjacent inclined side of the free end tip of retention structure 110 and a second side that is more steeply transverse to the longitudinal axis of retention structure 110. The more gradually inclined side of each barb 115 enters tissue relatively easily. But the more steeply sloped "back" side of each barb does not encourage tissue to slip back over the extreme outer tip of that barb in the event that withdrawal force is applied to the magnetic device. Accordingly, barbs 115 help to hold magnetic device 100 securely to tissue into which retention structure 110 has been driven.

Figure 60:
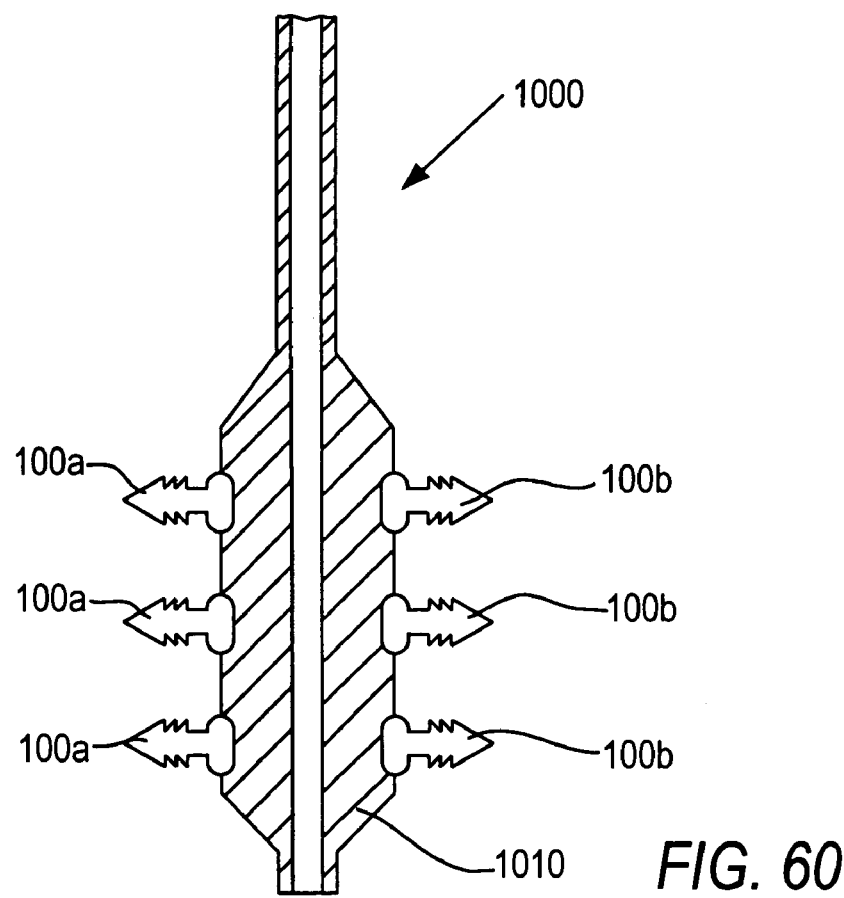
FIG. 60 is a simplified elevational view of illustrative apparatus that can be for implanting in a patient magnetic devices of the type shown in FIG. 59, for example, in accordance with the invention.

FIG. 60 shows another illustrative embodiment of apparatus 1000 for deploying magnetic devices 100 in accordance with the invention. In FIG. 60 apparatus 1000 is shown deploying magnetic devices 100 of the type shown in FIG. 59.

However, this is only illustrative, and apparatus like 1000 can be used with differently configured magnetic devices 100 if desired.

In the embodiment shown in FIG. 60, magnetic devices 100 are releasably attached to the outside of an inflatable balloon 1010 that is part of apparatus 1000. Balloon 1010 is initially deflated, and it may be introduced into the patient's esophagus (not shown) inside a delivery catheter (also not shown). Introduction may be via the patient's mouth. When the magnetic devices 100 on balloon are at the desired location in the esophagus, the delivery catheter is retracted proximally to expose balloon 1010 and devices 100. Balloon 1010 is then inflated (as shown in FIG. 60) to drive magnetic devices 100 into the esophageal tissue on opposite sides of the esophageal lumen. Balloon 1010 is then deflated, and apparatus 1000 is withdrawn from the patient via the patient's mouth.

Figure 61:
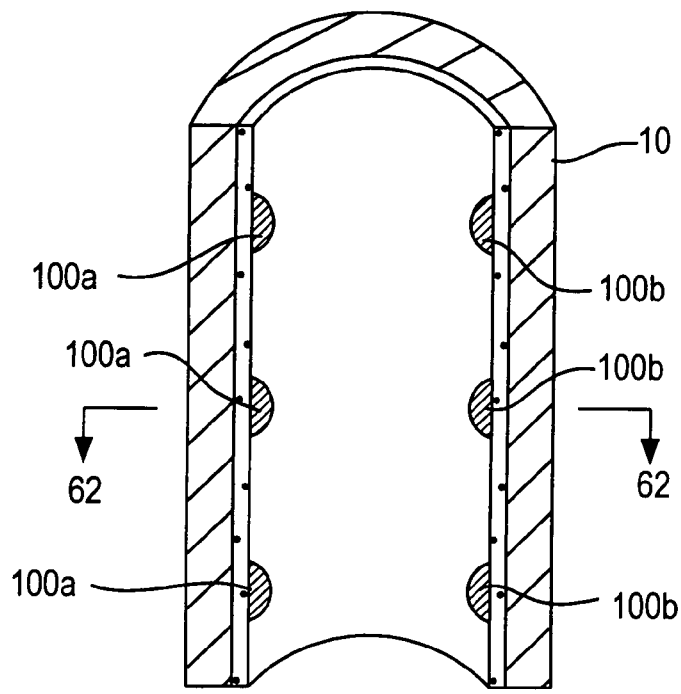
FIGS. 61-64 are similar to FIGS. 50-53, respectively, for yet another illustrative implantation of magnetic devices in a patient in accordance with the invention.
Figure 62:
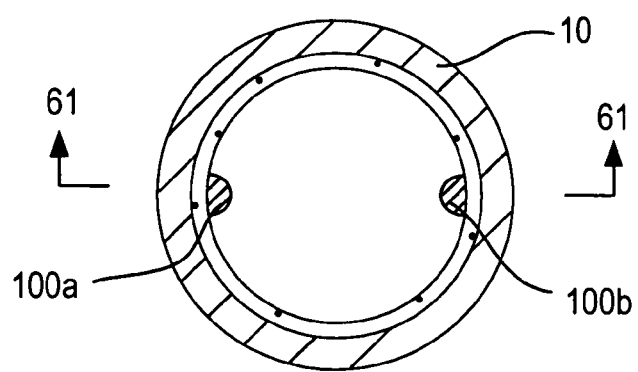
Figure 63:
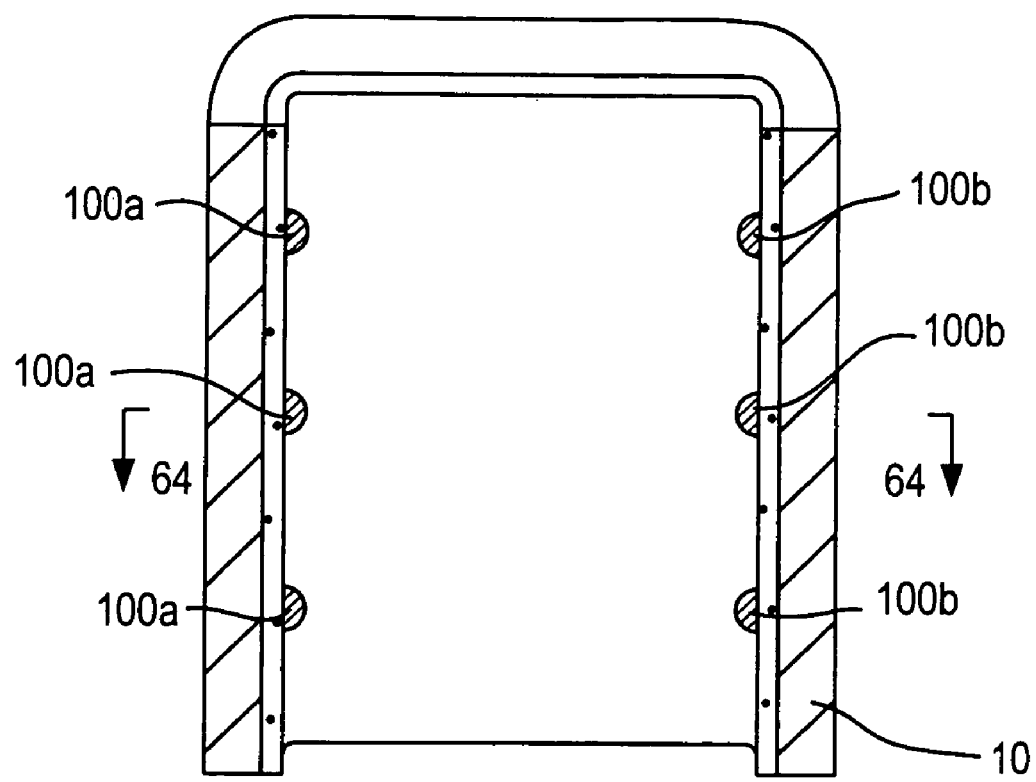
Figure 64:
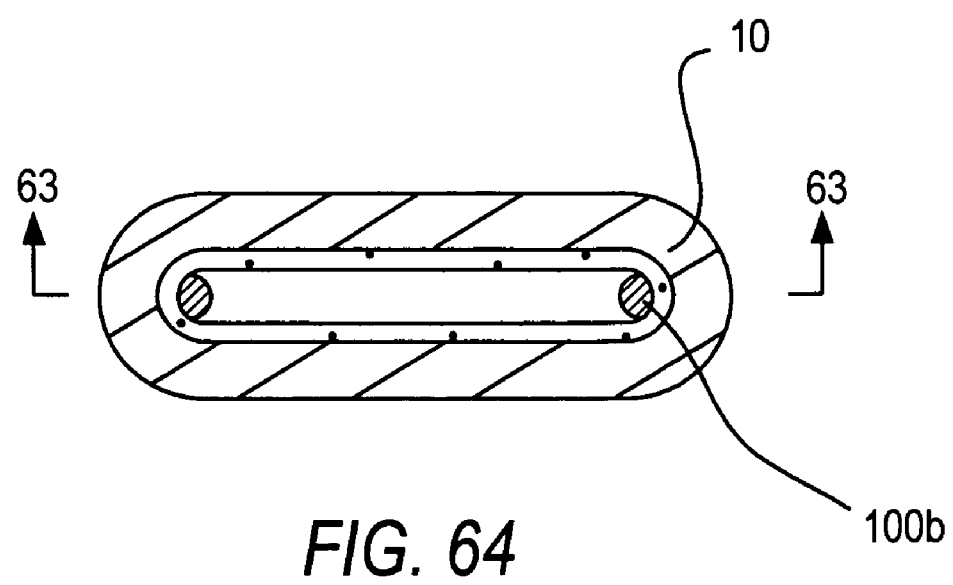

FIGS. 61-64 show a generalized illustrative embodiment in which magnetic devices 100 having the same (rather than opposite) polarity are employed. (FIGS. 61 and 62 show esophagus 10 open; FIGS. 63 and 64 show esophagus 10 closed.) "Having the same polarity" means that the magnetic poles of magnetic devices 100 that have the strongest magnetic interaction with one another are oriented so that those devices magnetically repel one another. In other words, the polarities of the poles of two magnetic devices 100 that face one another are the same so that those devices will repel one another (rather than attract one another as in previously depicted embodiments). For example, in FIGS. 61-64 all of devices 100 may have their "positive" or "north" pole facing in toward the center of the lumen of esophagus 10. Alternatively, all of devices 100 may have their "negative" or "south" pole facing in toward the center of the lumen of esophagus 10. The result of either of these magnetic orientations of devices 100 is that each of magnetic devices 100a repels the diametrically opposite magnetic device 100b. This causes the magnetic devices on opposite sides of esophagus 10 to push those portions of the esophagus apart as shown in FIGS. 63 and 64. Pushing those parts of the perimeter of the esophagus apart pulls the intervening portions of the esophagus perimeter together as is also seen in FIGS. 63 and 64 (especially FIG. 64). This helps to hold the esophagus normally closed, as is desired to combat GERD.

Figure 65:
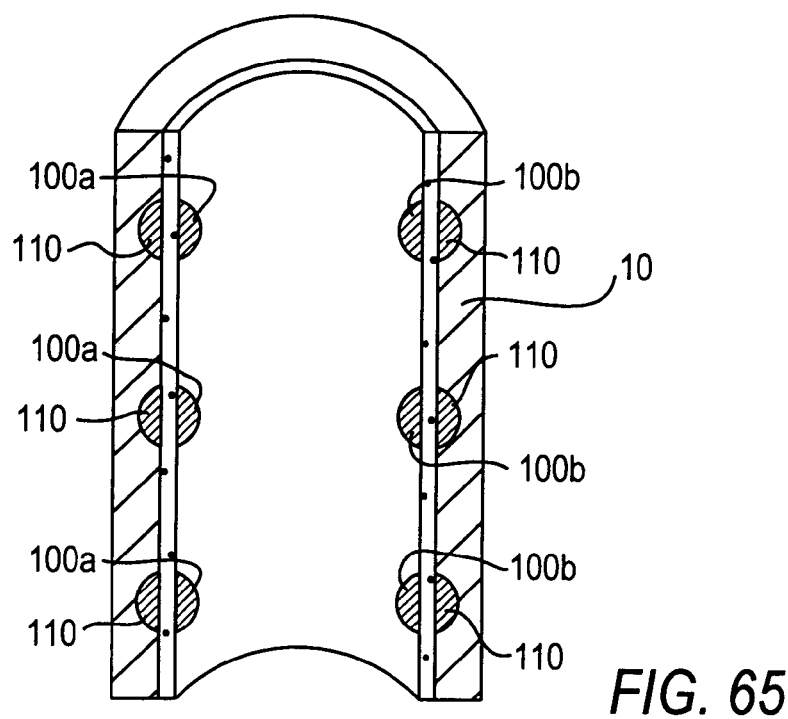
FIG. 65 is similar to FIG. 50 for still another illustrative implantation of magnetic devices in a patient in accordance with the invention.

FIG. 65 shows another illustrative embodiment in which magnetic devices 100 are held in position the inner surface of the wall of esophagus 10 by other retention magnets 110 that are embedded farther into the tissue of the esophageal wall. (FIG. 65 shows esophagus 10 open.) In other words, each magnetic device 100 is magnetically attracted to a retention magnet 110 in the wall of the esophagus. This magnetically holds each magnetic device 100 in the desired position on the inner surface of the esophageal wall. Illustrative apparatus that can be used to implant retention magnets 110 is shown in later FIGS. and described below. Once retention magnets 110 are implanted, magnetic devices 100 can be implanted adjacent to them (e.g., by apparatus of the general type shown in FIG. 60; see alternatively FIGS. 71-73)

Figure 66:
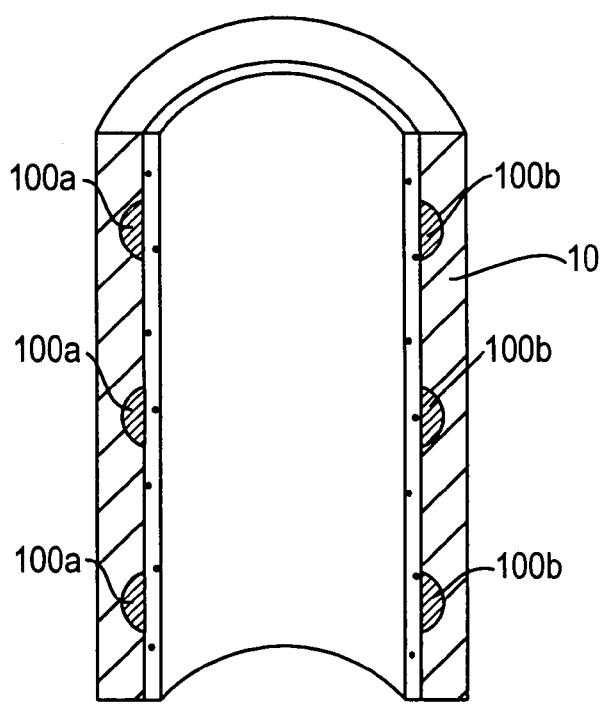
FIG. 66 is again similar to FIG. 50 for yet another illustrative implantation of magnetic devices in a patient in accordance with the invention.

FIG. 66 shows yet another illustrative embodiment in which magnetic devices 100 are embedded in the tissue of the esophagus, rather than being largely on the surface of that tissue. (Once again, FIG. 66 shows esophagus 10 open.) This embodiment is somewhat like the embodiment shown in FIG. 65, except that now the magnets embedded in the tissue are the primary magnetic devices 100, rather than additional retention magnets 110 for the primary magnets. Illustrative apparatus that can be used to implant magnetic devices 100 as shown in FIG. 66 is shown in later FIGS. and described below.

Figure 67:
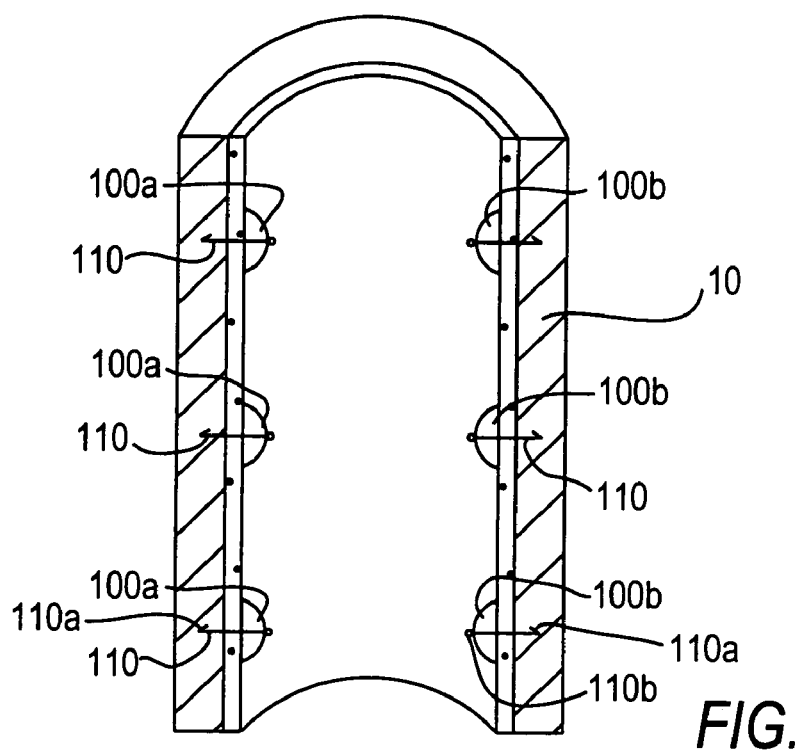
FIG. 67 is once again similar to FIG. 50 for still another illustrative implantation of magnetic devices in a patient in accordance with the invention.

FIG. 67 shows yet another illustrative embodiment of means for securing magnetic devices 100 to the wall of esophagus 10. (Esophagus 10 is again shown open in FIG. 67.) In this embodiment each magnetic device 100 is held to the esophageal wall by a pin 110 that passes through the magnetic device into the tissue wall. Each pin 110 has one or more barbs 110a on the portion that penetrates tissue. Barbs 110a resist being pulled back out of the tissue and thereby help to secure the associated magnetic device 100 to the tissue. An enlarged head 110b on each of pins 110 prevents the associated magnetic device 100 from coming off the pin. Illustrative apparatus that can be used for implanting magnetic devices 100 of the type shown in FIG. 67 is shown in FIG. 60 and described above.

Figure 68:
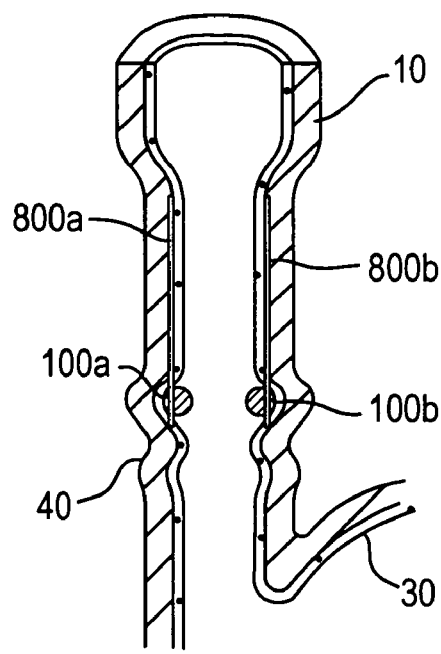
FIG. 68 is again generally similar to FIG. 50 showing yet another illustrative implantation of magnetic devices in a patient in accordance with the invention.

FIG. 68 shows an illustrative embodiment of a variation on what is shown in FIGS. 42-49 and described above. (FIG. 68 again shows esophagus 10 open.) In FIG. 68 each magnetic device 100 is held in place in esophagus 10 by an associated retention stylet 800. In this embodiment significantly more of each stylet 800 is in the tissue above the associated magnetic device 100 than is in the tissue below that device. When the patient swallows something, the progressive opening of the esophagus proceeding in the distal direction causes the relatively long upper portions of stylets 800 to first pivot apart and thereby begin separation of magnetic devices 100a and 100b from one another. This makes it relatively easy for swallowing to separate the magnets. Any attempted reflux in the opposite direction, however, does not operate relatively long lever arms of stylets 800 as has just been described for swallowing. The structure therefore resists separation of magnetic devices 100a and 100b more strongly for reflux than for swallowing, which may be beneficial to combat GERD without increasing resistance to swallowing to the same degree.

Figure 69:
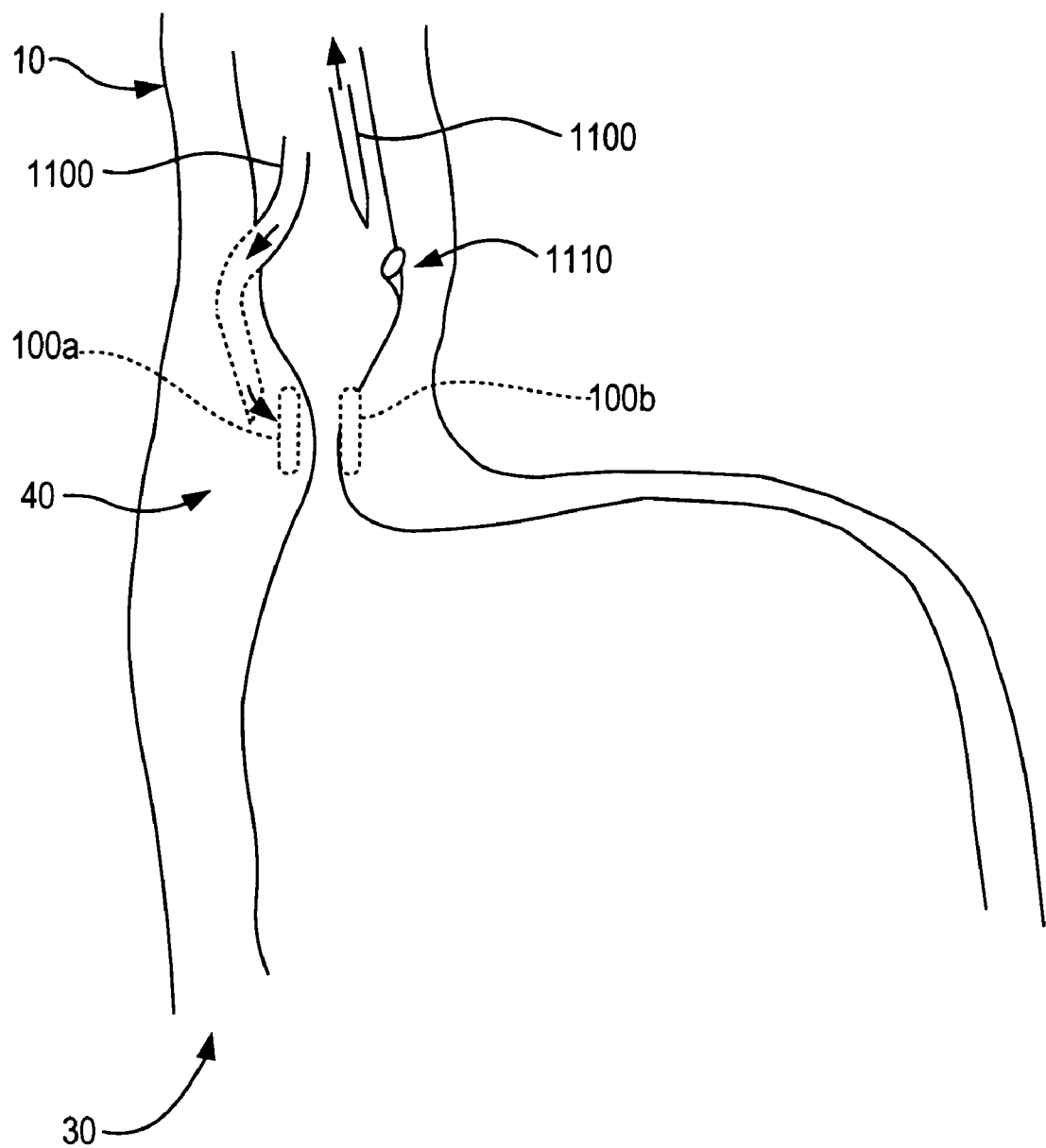
FIG. 69 is a simplified sectional view shoeing another embodiment of illustrative apparatus for implanting magnetic devices in a patient in accordance with the invention.

FIG. 69 shows illustrative apparatus for embedding magnetic devices 100 in the tissue of the wall of a patient's esophagus 10. Thus apparatus of this kind can be used to produce the implants shown in FIG. 66 or to implant retention magnets 110 as shown in FIG. 65. In the embodiment shown in FIG. 69 a pair (or more) of magnetic devices 100 are delivered intra-murally into esophagus 10. A cannula catheter 1100 is inserted trans-orally and advanced to the site of the lower esophageal sphincter 40. (FIG. 69 shows two cannula catheters 1100, but it may be preferable to use two such catheters one after the other (one on each side of the esophagus) or to use one catheter for two successive installations (one on each side of the esophagus).) The cannula 1100 then pierces and enters the wall of the esophagus. After the desired degree of penetration, a magnetic device 100 is forced out of the distal end of the cannula to embed the device in the tissue. The cannula is then withdrawn from the tissue, leaving behind the implanted magnetic device 109 (and possibly a cannula exit 1110, which soon heals). Ultimately the cannula is completely withdrawn from the patient. Magnets 100a and 100b (installed on respective opposite sides of the esophagus as has just been described) are of opposite magnetic polarity so that they magnetically attract one another (see FIG. 70, which shows the end result of the implantation shown in-progress in FIG. 69). The two magnets add bulk and tone (or pressure) to the LES. In the absence of devices 100, transient relaxation of the LES may allow that sphincter to open at low pressure, permitting reflux and the condition known as GERD. To overcome this low pressure relaxation, the magnetic force of magnets 100 is added to the closing tone pressure of the LES. The amount of this magnetic force can be tailored to an individual's clinical requirement. Because the LES is mostly closed, the mutual attraction of magnetic devices 100 will help to prevent their migration in the tissue from the locations in which they are first implanted. It will be apparent from what has been said that this invention provides the advantages of adding a bulking agent to the esophagus which does not migrate and which increases LES tone directly related to the magnetic force applied.

Figure 71:
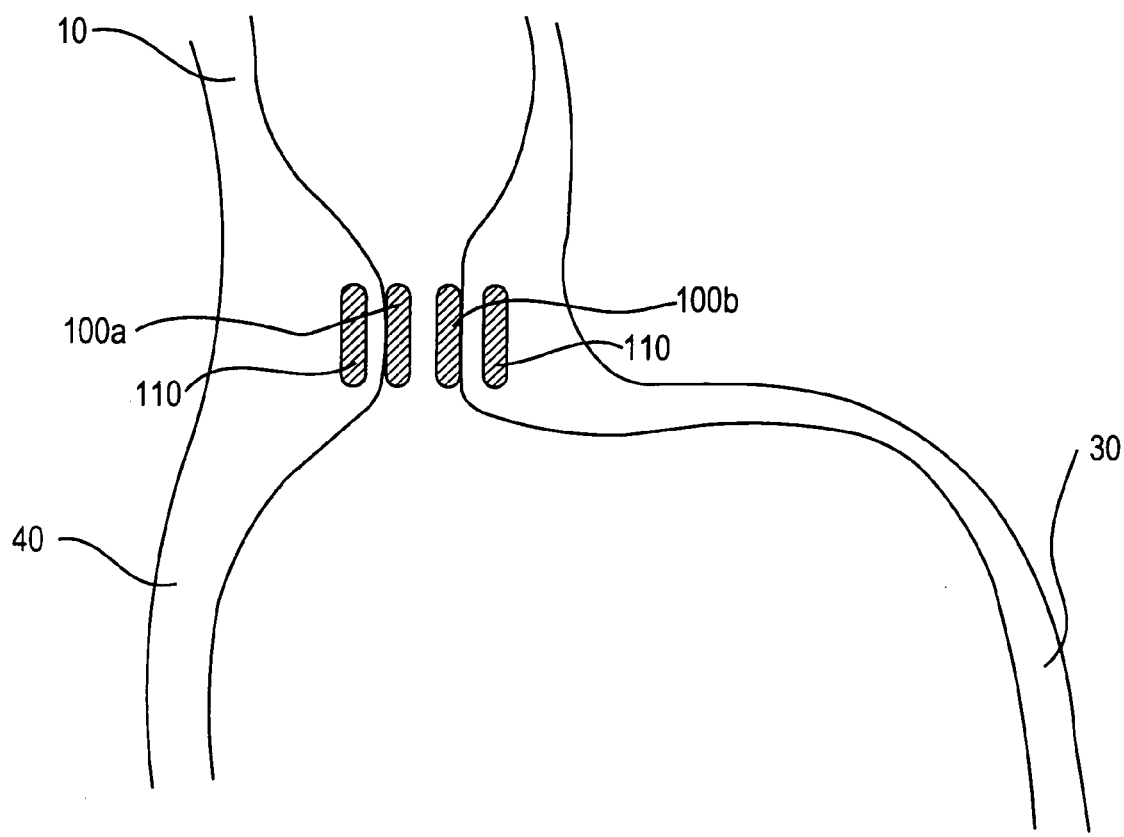
FIG. 71 is a view similar to FIG. 70, but showing another illustrative type of implantation of magnetic devices in accordance with the invention.
Figure 72:
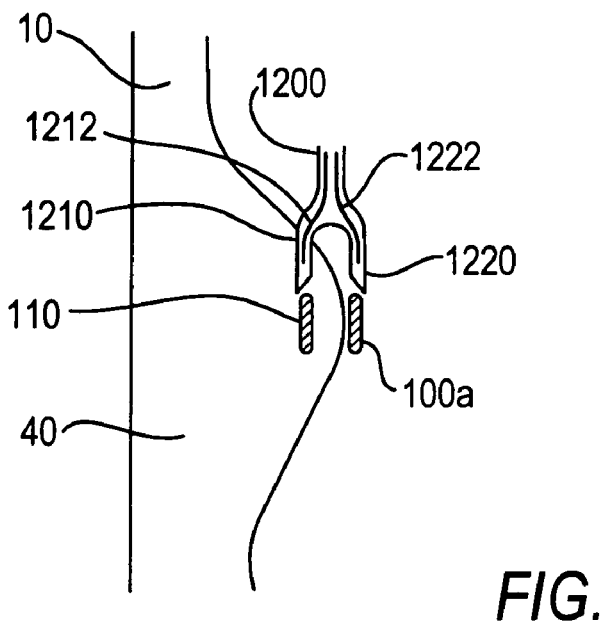
FIG. 72 is a simplified, partial, sectional view showing an illustrative embodiment of apparatus for implanting magnetic devices of, for example, the type shown in FIG. 71 in accordance with the invention.
Figure 73:
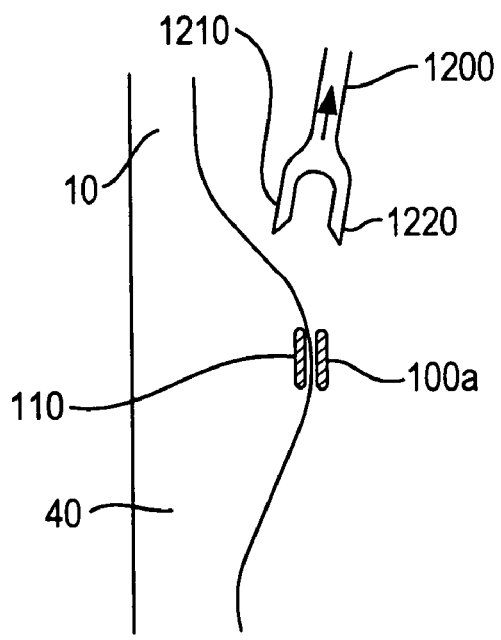
FIG. 73 is a view similar to FIG. 72 showing a later stage in use of the apparatus shown in FIG. 72 in accordance with the invention.

FIGS. 71-73 show an embodiment like that shown in FIG. 65, but with some additional details. In FIG. 71 each of magnetic devices 100a and 100b is shown held on the surface of the esophageal wall on a respective side of the esophageal lumen at or near LES 40 by an associated retention magnet 110 embedded in the tissue of the esophageal wall. On each side of the esophagus, magnets 110 and 100 are inserted either simultaneously or intramural magnet 110 first. The two magnets 100 and 110 in each such pair attract one another with at least some esophageal tissue in between. The geometry of the magnets may be selected to allow for additional mechanical securement between the magnets and also to conform to natural anatomical geometry (e.g., curved to match the curve of the esophageal wall). The matching and cooperating magnets help to prevent migration of either magnet. The intramural magnet 110 secures the associated intraluminal magnet 100. Typically the magnet pair on one side of the esophagus is implanted first, and then the magnet pair on the other side is implanted. Typical spacing between the magnet pairs is approximately 180° in the circumferential direction around the esophageal lumen. The implanted first and second pairs of magnets attract one another, providing a magnetic force to add tone pressure to the LES 40 or to modify the closing geometry to reduce or eliminate reflux.

FIGS. 72 and 73 show illustrative apparatus 1200 for implanting pairs of magnets 100 and 110 as shown in FIG. 71. A cannula catheter 1200 can be inserted into the patient's esophagus 10 via the patient's mouth. When the distal end of the catheter 1200 reaches the proper location (adjacent LES 40), one branch 1210 of the catheter is made to penetrate the tissue of the esophageal wall as shown in FIG. 72. Then a retention magnet 110 is pushed (by magnet pusher 1212) from the distal end of branch 1210 to embed that magnet in the esophageal tissue. At the same time or soon thereafter, a magnetic device 100a is pushed (by magnet pusher 1222) from the distal end of a second branch 1220 of the catheter. Magnetic device 100a is magnetically attracted to embedded retention magnet 110 and thereby held in place in the lumen of esophagus 10. Delivery apparatus 1200 can then be withdrawn from the patient as shown in FIG. 73. That apparatus can then be reloaded and reused (or another similar apparatus can be used) to implant two more magnets 100b and 110 in the same way on the opposite side of the esophageal lumen.

Figure 70:
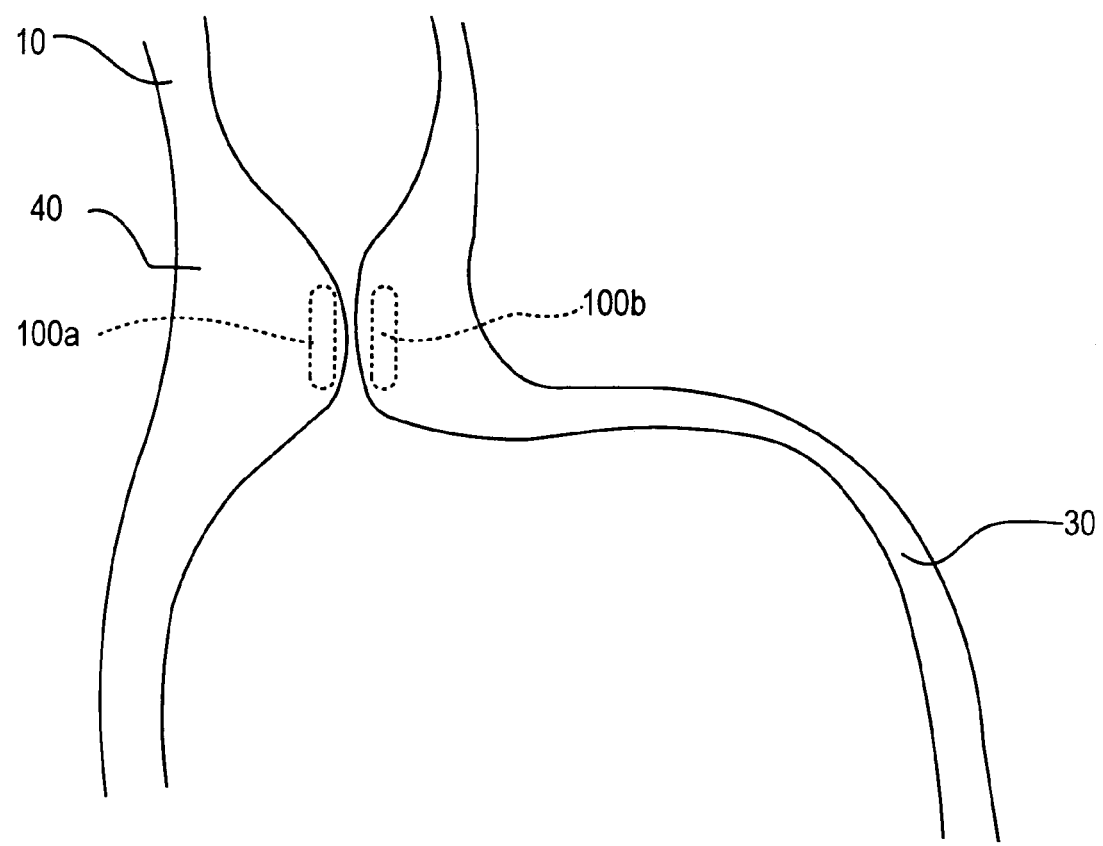
FIG. 70 is another simplified sectional view showing the end result of an implantation as shown in FIG. 69.

Any of the delivery systems shown and described herein can be aided by direct visualization, x-ray visualization, echo visualization, or the like. For example, echo visualization can be used to determine the depth at which the retention magnets like 110 in FIGS. 65 and 71-73 or the primary magnets 100 in embodiments like FIGS. 66, 69, and 70 are delivered into the wall of the esophagus.

Figure 74:
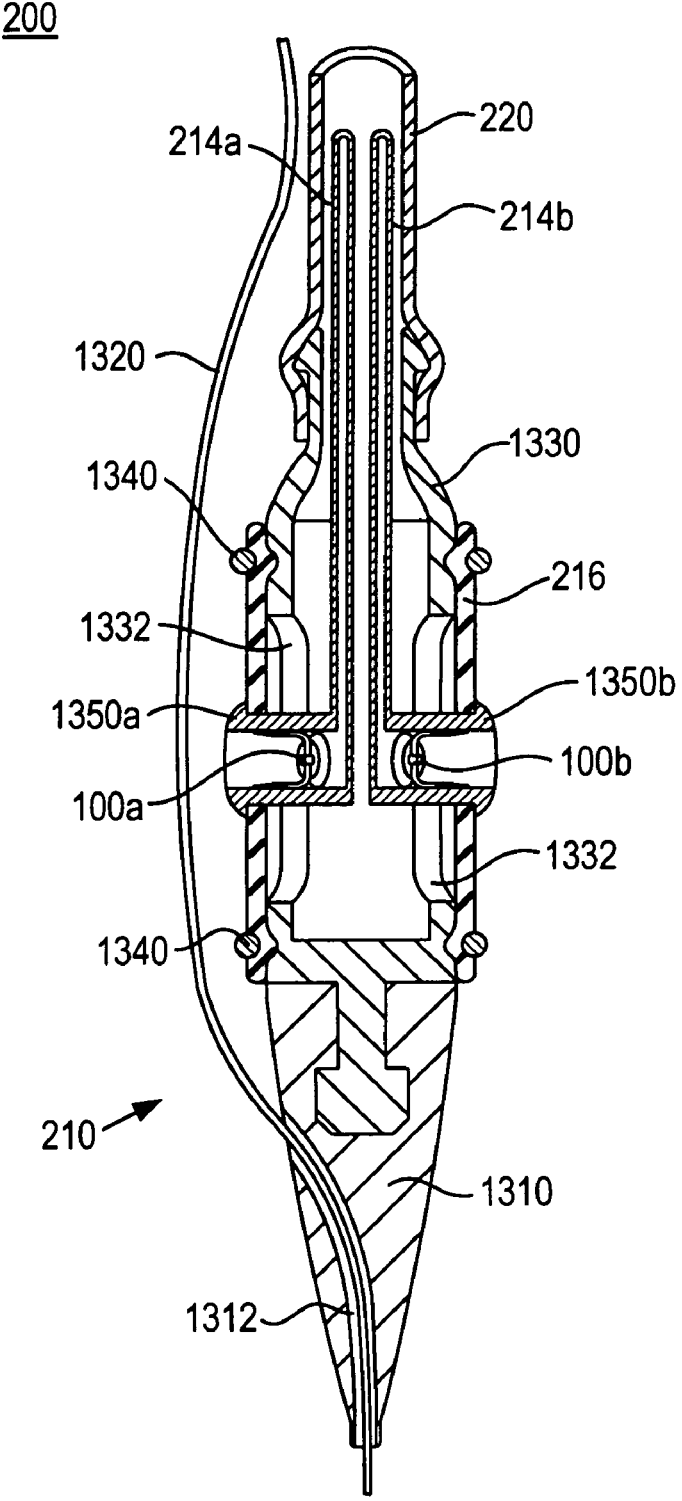
FIG. 74 is a simplified, partial, sectional view of another illustrative embodiment of apparatus in accordance with the invention.
Figure 75:
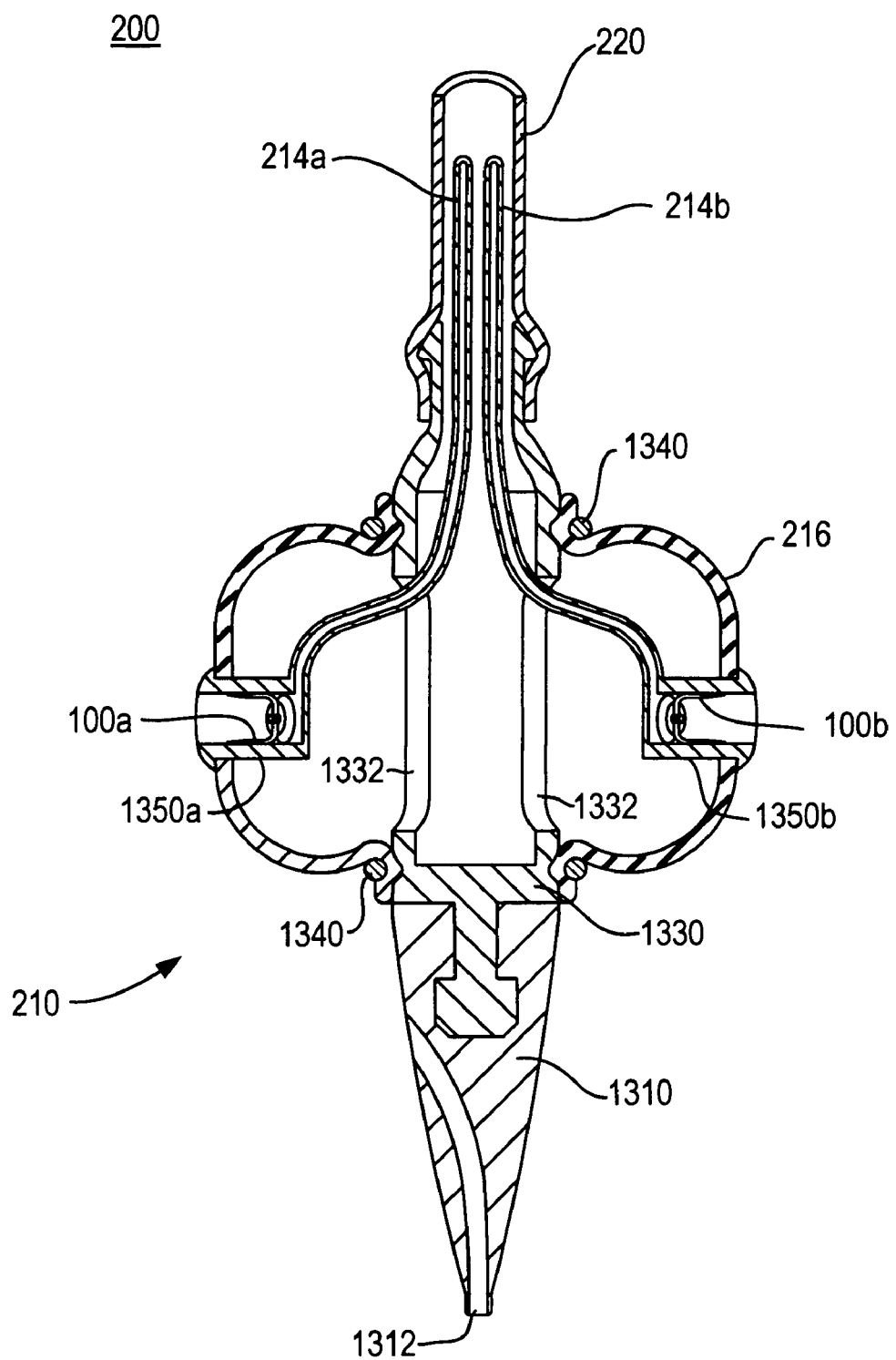
FIG. 75 shows a later stage in use of the apparatus shown in FIG. 74 in accordance with the invention.

FIGS. 74 and 75 show another illustrative embodiment of the distal portion 210 of illustrative deployment system 200. In this embodiment distal portion 210 includes a distal tip portion 1310, which is preferably relatively soft (e.g., of silicone or a polymer) to help make the delivery system atraumatic to tissue. A wire lumen 1312 is formed through tip portion 1310 so that, if desired, distal portion 210 can be fed into the patient along a guidewire 1320 that has been inserted in the patient. Use of guidewire 1320 and guidewire lumen 1312 may improve "trackability" of the apparatus into the patient. Once distal portion 210 is at the desired location in the patient, guidewire 1320 can be withdrawn from the patient, which is why guidewire 1320 is not visible in FIG. 75.

The distal portion 210 shown in FIGS. 74 and 75 includes only a single balloon structure 216, which preferably extends annularly all the way around a relatively rigid, largely hollow core member 1330. Balloon structure 216 can be formed by placing a tube of balloon material annularly around core member 1330 and then securing each end of that tube to the core member with a respective one of annular balloon restraints 1340. Each of restraints 1340 is a ring that fits sufficiently around the adjacent portion of balloon 216 and core member 1330 to seal the balloon to the core. The open proximal end of core member 1330 is annularly sealed to the distal end of the lumen of catheter 220 (e.g., by being press-fitted into the distal end of the catheter lumen. Core member 1330 has at least one opening 1332 (two are shown) from its hollow interior to the interior of balloon 216 between restraints 1340. Accordingly, balloon structure 216 can be inflated as shown in FIG. 75 by supplying pressurized fluid to the interior of core member 1330 via the lumen of catheter 220.

Balloon structure 216 carries two pockets 1350a and 1350b for magnetic devices 100a and 100b. Pockets 1350 are on diametrically opposite sides of distal portion 210, and they pass freely through above-mentioned openings 1332 in core member 1330. When balloon 216 is inflated as shown in FIG. 75, pockets 1350 and magnetic devices 100 move radially outwardly with the adjacent portion of the surface of balloon 216 (through which pockets 1350 pass with sealing connections to the balloon). As in other embodiments, inflation of balloon 216 somewhat distends the adjacent tissue of the esophagus in which distal portion 210 is located, thereby helping to stretch the esophageal tissue across the openings of pockets 1350 and preparing that tissue to receive magnetic devices 100. Magnetic devices 100 can be releasably held in pockets 1350, and also selectively released or driven from pockets 1350, using any of several of the techniques described earlier. In the particularly preferred embodiment shown in FIGS. 74 and 75, pressurized fluid is used to drive each magnetic device 100 from its pocket 1350 (similar to what is shown, for example, in FIG. 3 and described earlier in connection with that FIG.). Thus tubes 214 are provided in catheter 220 and into the interior of core member 1330 to supply pressurized fluid to each of pockets 1350 behind the magnetic device 100 in that pocket when it is desired to drive the magnetic device from its pocket. A difference from FIG. 3 is that in FIGS. 74 and 75 (as has been mentioned) pockets 1350 travel radially outwardly with the surface of balloon 216 when the balloon is inflated. Accordingly, tubes 214 must have sufficient flexibility and slack to permit their distal end portions to also travel radially outwardly with pockets 1350 as shown in FIG. 75. Tubes 214 also pass through openings 1332 in core member 1330 when their distal end portions travel radially outwardly with pockets 1350.

To conclude this discussion of the FIGS. 74 and 75 embodiment, after balloon 216 has been inflated as shown in FIG. 75; pressurized fluid is supplied to each pocket 1350 via the associated tube 214 to drive the associated magnetic device 100 from that pocket and into the esophageal tissue that is somewhat stretched over the exit from the pocket. Balloon structure 216 is then deflated to restore it to a condition like that shown in FIG. 74, and the apparatus is withdrawn from the patient, leaving only implanted magnetic devices 100 behind in the patient.

Figure 76:
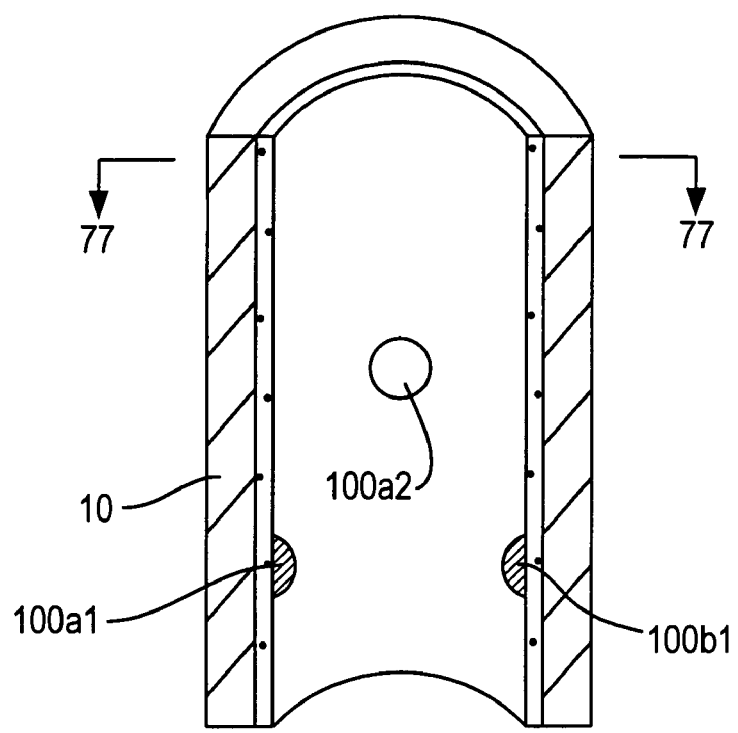
FIG. 76 is a simplified sectional view (taken generally along the line 76-76 in FIG. 77) showing another illustrative implantation of magnetic devices in a patient in accordance with the invention.
Figure 77:
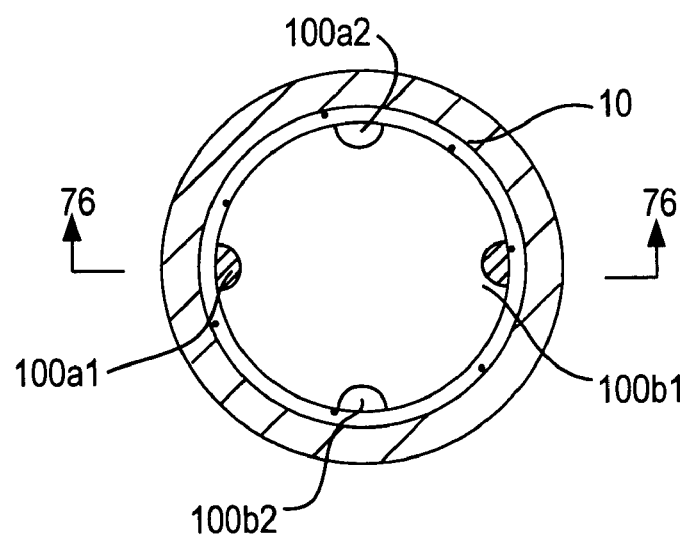
FIG. 77 is another simplified sectional view taken generally along the line 77-77 in FIG. 76.
Figure 78:
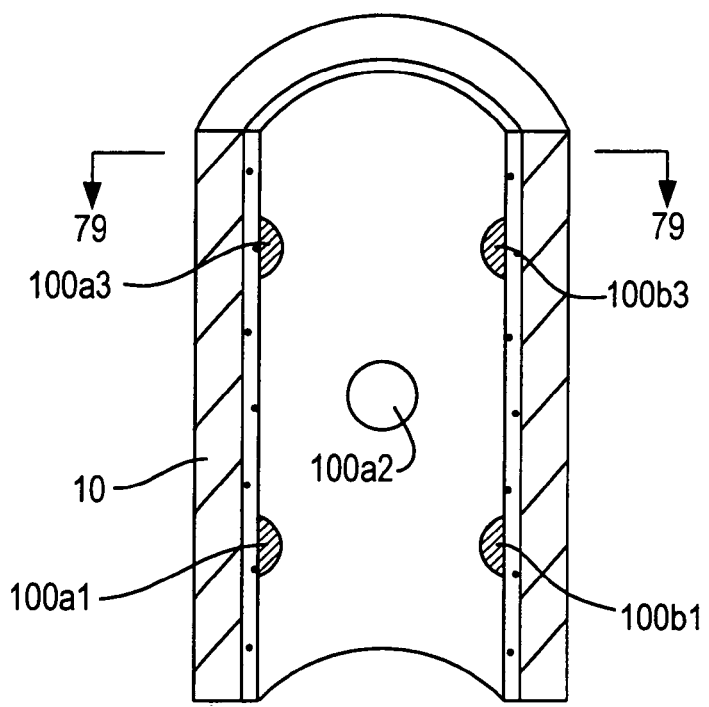
FIG. 78 is a view similar to FIG. 76, but for yet another illustrative implantation of magnetic devices in a patient in accordance with the invention.
Figure 79:
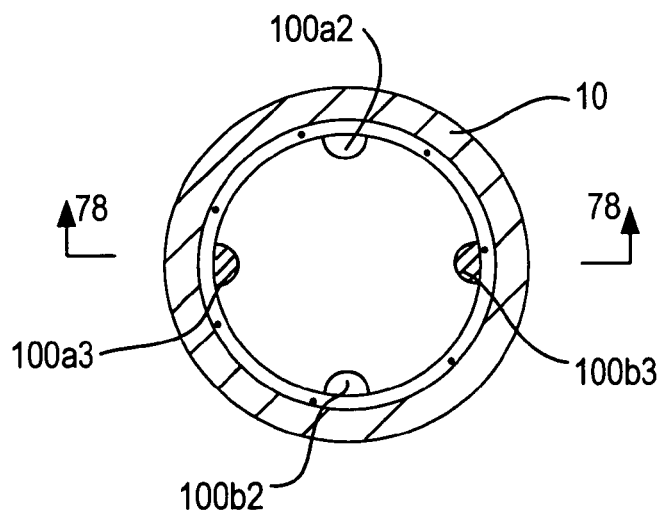
FIG. 79 is another simplified sectional view taken generally along the line 79-79 in FIG. 78.

FIGS. 76-79 show some more examples of how magnetic devices 100 may be implanted in a patient's esophagus 10 in accordance with the invention. In FIGS. 76 and 77 two pairs or sets of magnetic devices 100 are implanted at locations that are axially spaced from one another along esophagus 10. In particular, magnetic devices 100a1 and 100b1 ("set 100-1") are implanted lower in esophagus 10 than magnetic devices 100a2 and 100b2 ("set 100-2"). In addition, set 100-2 is rotated (in a direction circumferentially of esophagus 10) relative to set 100-1. In particular, set 100-2 is rotated 90° relative to set 100-1. FIGS. 78 and 79 show the addition of a third set of magnetic devices (100a3 and 100b3 ("set 100-3")) to what is shown in FIGS. 76 and 77. All three sets in FIGS. 78 and 79 are axially spaced from one another along esophagus 10. In addition, set 100-2 is rotated relative to set 100-1, but set 100-3 is not rotated relative to set 100-1.

The use of multiple sets of magnetic devices as shown, for example, in FIGS. 76-79 allows management of the esophagus 10 if it does not close symmetrically. For example, if a set of magnets is deployed with an anterior-posterior orientation, and the esophagus closes in a left-right lateral direction, the magnets will not come into contact. By placing two sets—one with an anterior-posterior orientation and one with a left-right lateral orientation (or alternatively with any similar 90° angular off-set relative to one another) —the resulting arrangement of the magnetic devices will account for any way in which the esophagus may naturally close and still ensure that at least one set of magnets comes into contact.

Figure 80:
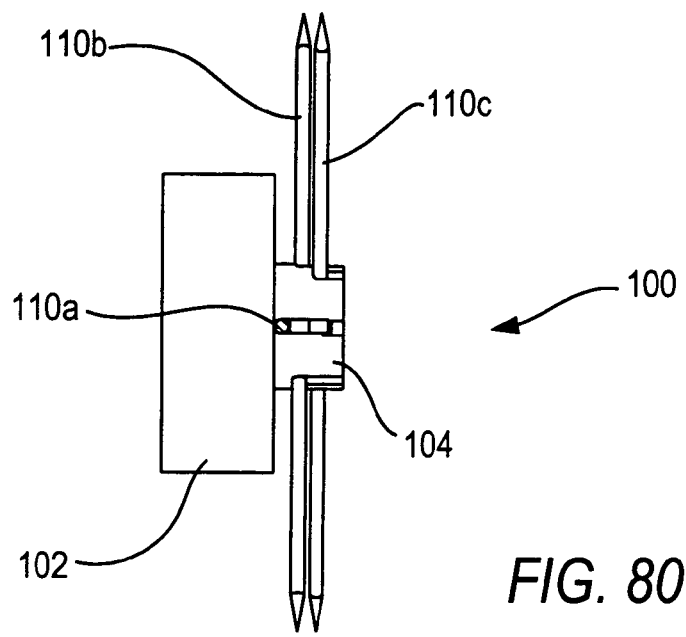
FIG. 80 is a simplified elevational view of another illustrative embodiment of an implantable magnetic device in accordance with the invention.
Figure 81:
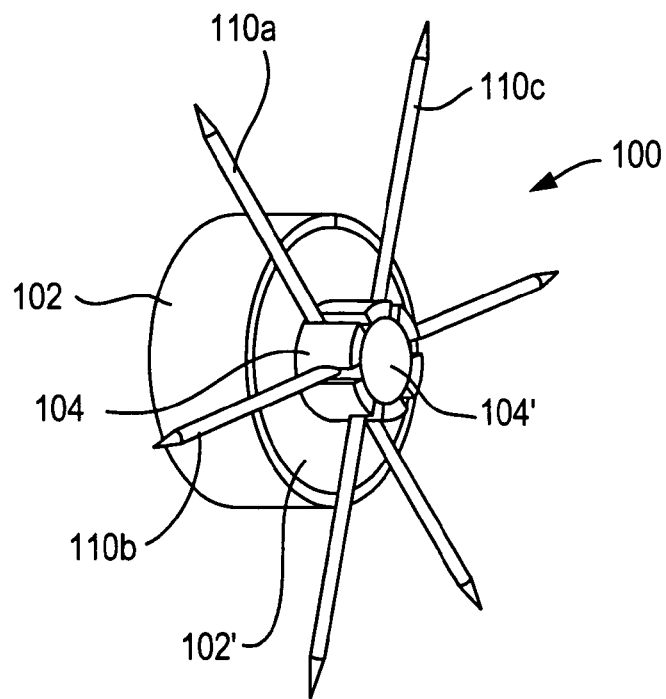
FIG. 81 is a simplified perspective view of the magnetic device shown in FIG. 80.

FIGS. 80 and 81 show yet another illustrative embodiment of a magnetic device 100 in accordance with the invention. In this embodiment the actual magnetic material (active or passive) is contained in a cup-shaped magnet case portion 102. This cup-shaped portion 102 is closed by disc-shaped case portion 102', which is secured to cup-shaped portion 102 by such means as a laser weld, brazing, a press-fit connection, solder, or the like. Wire retainer structure 104 projects out from the center of the outer major surface of member 102'. Three elastic wires 110a-c (e.g., of nitinol) with sharpened free ends extend transversely across wire retainer structure 104 with angular orientations that are equally spaced from one another around structure 104. Wires 110 may be held in structure 104 by several means (e.g., by being press fit into slots in structure 104 and/or by being pressed into structure 104 by cover or closure 104' (which again may be secured to structure 104 by laser welding, brazing, press fitting, soldering, or the like). Thus although device 100 as shown in FIGS. 80 and 81 employs only three wires 110a-c, six retention fingers for securing the implant result from this construction.

Although each of the depicted embodiments tends to employ one type of magnetic device, it will be understood that different types of magnetic devices (e.g., those from different ones of the depicted embodiments) can be used together if desired. For example, an embedded magnet (e.g., as in FIG. 66) on one side of the esophagus can be used to magnetically interact with a surface-mounted magnet (e.g., as in FIG. 67) on the other side of the esophagus. The magnetic devices used together do not all have to be of the same type or construction.

Although the invention has been illustratively discussed primarily in the context of treating GERD, the invention has many other possible applications, as will be readily apparent to those skilled in the art from this specification. Examples of its various possible applications include treatment of a wide variety of body passages, organs, or cavities in the digestive, respiratory, circulatory, reproductive, and excretory systems.

Treatment in accordance with the invention may mean increasing strength, changing shape, restricting flow, decreasing size, changing wall tension, affecting or effecting tissue movement, or the like. Some specific examples other than treatment of GERD are mentioned in the next few sentences. Magnets may be implanted in the stomach to limit its capacity for food intake by partitioning or restricting at least a portion of the stomach area from food. This results in reduced capacity for food intake and subsequent weight reduction. Conditions such as emphysema may be improved by reducing access of air intake to diseased sections of lung tissue. Magnets may be used to collapse or restrict air flow in the bronchial air lumens that lead to diseased lung sections. This effectively reduces lung capacity and directs air intake to the healthiest tissue. Other examples of use of the invention are referred to elsewhere in this specification.

It will be understood that the foregoing is only illustrative of the principles of the invention, and that various modifications can be made by those skilled in the art without departing from the scope and spirit of the invention.

What is claimed is:

1. A magnetic implant structure for use in a patient comprising:
    a plurality of magnetic devices; and
    a member for securing the plurality of magnetic devices to a surface of tissue in the patient, wherein the member is of fixed length and is configured to movably enter an aperture in each of the plurality of magnetic devices.

2. The structure defined in claim 1 wherein the member is configured to penetrate the tissue adjacent the magnetic devices.

3. The structure defined in claim 2 wherein the member is magnetic.

4. The structure defined in claim 2 wherein the member is configured to resist withdrawal from tissue it has penetrated.

5. The structure defined in claim 2 wherein the member is configured to pass through each of the magnetic devices.

6. A magnetic implant structure for use in a patient comprising:
    a magnetic device; and
    a member for securing the magnetic device to a surface of tissue in the patient, wherein the member is of fixed length and is configured to movably enter an aperture in the magnetic device, wherein the member is configured to penetrate the tissue adjacent the magnetic device, wherein the member is configured to pass through the magnetic device, and wherein the member is configured to be extended from tissue adjacent a first side of the magnetic device, through the magnetic device, and into tissue adjacent a second side of the magnetic device.

7. A prosthetic implant structure comprising:
    a longitudinal member having a fixed length; and
    first and second magnetic devices that are disposed at different points along the longitudinal member, at least one of the magnetic devices being movable relative to the longitudinal member in a direction that is lengthwise of the longitudinal member as a result of a portion of a length of the longitudinal member movably entering an aperture in the at least one of the magnetic devices.

* * * * *

UNITED STATES PATENT AND TRADEMARK OFFICE
CERTIFICATE OF CORRECTION

| | | |
|---|---|---|
| PATENT NO. | : 7,445,010 B2 | Page 1 of 1 |
| APPLICATION NO. | : 10/612496 | |
| DATED | : November 4, 2008 | |
| INVENTOR(S) | : Chad J. Kugler et al. | |

It is certified that error appears in the above-identified patent and that said Letters Patent is hereby corrected as shown below:

ON THE TITLE PAGE ITEM (54)

Change "USE OF MAGNETIC IMPLANTS TO TREAT ISSUE STRUCTURES" to --USE OF MAGNETIC IMPLANTS TO TREAT BODY TISSUE STRUCTURES--.

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

PATENT NO.         : 7,445,010 B2
APPLICATION NO.    : 10/612496
DATED              : November 4, 2008
INVENTOR(S)        : Chad J. Kugler et al.

It is certified that error appears in the above-identified patent and that said Letters Patent is hereby corrected as shown below:

ON THE TITLE PAGE ITEM (54) and Column 1, lines 1 and 2

Change "USE OF MAGNETIC IMPLANTS TO TREAT ISSUE STRUCTURES" to --USE OF MAGNETIC IMPLANTS TO TREAT BODY TISSUE STRUCTURES--.

This certificate supersedes the Certificate of Correction issued January 6, 2009.

Signed and Sealed this

Third Day of February, 2009

JOHN DOLL
*Acting Director of the United States Patent and Trademark Office*